(12) United States Patent
Okubo et al.

(10) Patent No.: US 9,941,422 B2
(45) Date of Patent: *Apr. 10, 2018

(54) ORGANIC PHOTOELECTRIC CONVERSION ELEMENT AND SOLAR CELL USING THE SAME

(71) Applicant: Konica Minolta, Inc., Tokyo (JP)

(72) Inventors: Yasushi Okubo, Tokyo (JP); Hiroaki Itoh, Tokyo (JP); Ayako Wachi, Tokyo (JP); Hiroshi Ishidai, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 536 days.

This patent is subject to a terminal disclaimer.

(21) Appl. No.: 14/390,569

(22) PCT Filed: Apr. 4, 2013

(86) PCT No.: PCT/JP2013/060369
§ 371 (c)(1),
(2) Date: Oct. 3, 2014

(87) PCT Pub. No.: WO2013/151141
PCT Pub. Date: Oct. 10, 2013

(65) Prior Publication Data
US 2015/0096610 A1    Apr. 9, 2015

(30) Foreign Application Priority Data
Apr. 4, 2012 (JP) .................................. 2012-085905

(51) Int. Cl.
*H01L 31/00* (2006.01)
*H01L 31/0224* (2006.01)
(Continued)

(52) U.S. Cl.
CPC .... *H01L 31/022425* (2013.01); *C07D 519/00* (2013.01); *C08G 61/10* (2013.01);
(Continued)

(58) Field of Classification Search
CPC .............. C07D 519/00; H01L 31/0224; H01L 31/022425; H01L 31/022466;
(Continued)

(56) References Cited

U.S. PATENT DOCUMENTS

2006/0141662 A1    6/2006  Brabec et al.
2007/0165237 A1*   7/2007  Knipp ....................... G01J 3/26
                                                 356/453
(Continued)

FOREIGN PATENT DOCUMENTS

JP    2002-083979 A    3/2002
JP    2006-508538 A    3/2006
(Continued)

OTHER PUBLICATIONS

Notification of Reasons for Refusal dated Dec. 20, 2016 from the corresponding Japanese Application No. 2014-509211; English translation of Notification of Reasons for Refusal: Total of 8 pages.
(Continued)

*Primary Examiner* — Susan D Leong
(74) *Attorney, Agent, or Firm* — Lucas & Mercanti, LLP

(57) ABSTRACT

Provided are a transparent conductive film having a simple manufacturing process and high transparency, high photoelectric conversion efficiency, and excellent durability and an organic photoelectric conversion element using this transparent conductive film.

The transparent conductive film of the present invention is formed by laminating a ground layer which contains a nitrogen-containing organic compound and a metal thin film layer which contains a metal element of Group 11 of the
(Continued)

periodic table and has a thickness of from 2 to 10 nm. In addition, the organic photoelectric conversion element of the present invention has a first electrode, a second electrode, and a photoelectric conversion layer present between the first electrode and the second electrode, and at least one of the first electrode and the second electrode of the organic photoelectric conversion element is a transparent conductive film formed by laminating the ground layer which contains the nitrogen-containing organic compound and the metal thin film layer which contains a metal element of Group 11 of the periodic table and has a thickness of from 2 to 10 nm.

16 Claims, 3 Drawing Sheets

(51) Int. Cl.
    *C07D 519/00*     (2006.01)
    *C08G 61/10*     (2006.01)
    *H01L 51/00*     (2006.01)
    *H01L 51/42*     (2006.01)
    *H01L 51/44*     (2006.01)

(52) U.S. Cl.
CPC .. *H01L 31/022466* (2013.01); *H01L 51/0021* (2013.01); *H01L 51/0035* (2013.01); *H01L 51/0039* (2013.01); *H01L 51/0067* (2013.01); *H01L 51/0072* (2013.01); *C08G 2261/312* (2013.01); *C08G 2261/3223* (2013.01); *C08G 2261/794* (2013.01); *C08G 2261/91* (2013.01); *H01L 51/0037* (2013.01); *H01L 51/0043* (2013.01); *H01L 51/0073* (2013.01); *H01L 51/42* (2013.01); *H01L 51/442* (2013.01); *Y02E 10/549* (2013.01); *Y10T 428/265* (2015.01)

(58) Field of Classification Search
CPC .............. H01L 51/0021; H01L 51/0035; H01L 51/0039; H01L 51/0067; H01L 51/0072; H01L 51/0037; H01L 51/0043; H01L 51/0073; H01L 51/42; H01L 51/442; C08G 61/10; C08G 2261/312; C08G 2261/3223; C08G 2261/794; C08G 2261/91

See application file for complete search history.

(56) References Cited

U.S. PATENT DOCUMENTS

| | | | |
|---|---|---|---|
| 2007/0172696 A1* | 7/2007 | Tong | .................... C23C 14/0676 428/689 |
| 2008/0029147 A1 | 2/2008 | Yang et al. | |
| 2011/0057920 A1 | 3/2011 | Matsuura et al. | |
| 2012/0211082 A1* | 8/2012 | Akiyama | .............. C07F 9/5325 136/263 |
| 2014/0272398 A1 | 9/2014 | Hakii et al. | |
| 2015/0221793 A1* | 8/2015 | Okubo | .............. H01L 31/02246 136/256 |

FOREIGN PATENT DOCUMENTS

| | | | | |
|---|---|---|---|---|
| JP | 2008-518446 A | 5/2008 | | |
| JP | 2009-192931 A | 8/2009 | | |
| JP | 2011-077028 A | 4/2011 | | |
| JP | 2011-124468 A | 6/2011 | | |
| JP | 2011-205075 A | 10/2011 | | |
| WO | WO2010/090123 A1 | 8/2010 | | |
| WO | WO 2011016430 A1 * | 2/2011 | ............ | C07F 9/5325 |
| WO | WO2011/093309 A1 | 8/2011 | | |
| WO | WO2013/073356 A1 | 5/2013 | | |

OTHER PUBLICATIONS

International Preliminary Report on Patentability, International Application No. PCT/JP/2013/060369, dated Oct. 7, 2014 and English translation thereof.

Qingfeng Dong, et al; All-spin-coating vacuum-free processed semi-transparent . . . ; Org. Electronics; vol. 11; 2010; pp. 1327-1331.

Office Action dated Jul. 12, 2016 from the corresponding Japanese Application; Application No. 2014-509211; English translation of Office Action; Total of 10 pages.

* cited by examiner

ORGANIC PHOTOELECTRIC CONVERSION ELEMENT AND SOLAR CELL USING THE SAME

CROSS REFERENCE TO RELATED APPLICATION

This Application is a 371 of PCT/JP2013/060369 filed on Apr. 4, 2013 which, in turn, claimed the priority of Japanese Patent Application No. JP2012-085905 filed on Apr. 4, 2012 both applications are incorporated herein by reference.

TECHNICAL FIELD

The present invention relates to an organic photoelectric conversion element and a solar cell using the same. More specifically, the present invention relates to a technology to improve the transparency, photoelectric conversion efficiency, or the like of an organic photoelectric conversion element.

BACKGROUND ART

In recent years, the reduction in the carbon dioxide emission has been ardently desired in order to deal with global warming. In addition, it is expected that the fossil fuel such as oil, coal, and natural gas is depleted in the near future and thus it is an urgent matter to secure earth-friendly energy resources to replace these. Hence, the development of power generation technology using sunlight, wind power, geothermal energy, nuclear power, or the like has been extensively conducted, and among them, the photovoltaic power generation has received particular attention in terms of high safety.

In the photovoltaic power generation, light energy is directly converted into electric power by using a photoelectric conversion element utilizing the photovoltaic effect. In general, the photoelectric conversion element has a structure consisting of a photoelectric conversion layer (light absorbing layer) sandwiched between a pair of electrodes, and light energy is converted into electrical energy in the photoelectric conversion layer. The photoelectric conversion element is formed into various types depending on the materials used in the photoelectric conversion layer or the form of the element, and a silicon-based photoelectric conversion element using single crystal Si, polycrystal Si or amorphous Si, a compound-based photoelectric conversion element using a compound semiconductor such as GaAs or CICS (a semiconductor consisting of copper (Cu), indium (In), gallium (Ga), and selenium (Se)), a dye-sensitized type photoelectric conversion element (Gratzel cell), or the like has been proposed and practically used.

Normally, solar cells using these photoelectric conversion elements are disposed on a roof or land. In recent years, however, semi-transparent type (see-through type) solar cells such as windows have attracted attention. These semi-transparent solar cells are not only simply able to generate electric power using sunlight irradiated to the window but are also able to reduce the penetration of solar heat (heat rays) into the room by solar radiation. Hence, it is expected not only the power generation effect but also the effect of air-conditioning cost reduction.

Such a solar cell which is a semi-transparent type capable of being installed to a window and also can be installed to the existing building by simply pasting is expected to be a new field to grow from now on as a building-integrated photovoltaic (BIPV) system.

Both the two electrodes constituting the solar cell (organic photoelectric conversion element) are required to be transparent in order to achieve the semi-transparent solar cell. A first electrode formed on the substrate is generally a transparent electrode composed of a metal oxide material such as ITO, but a second electrode (counter electrode) is conventionally a non-transparent electrode composed of a metallic material in many cases and thus improvement is desired.

As an example using a transparent electrode as the two electrodes constituting a photoelectric conversion element, for example, a method of using a transparent electrode composed of ITO in both the first electrode and the second electrode (Patent Literature 1), a method of using a conductive polymer in two electrodes (Non-Patent Literature 1), a method combining a conductive polymer and a metal mesh electrode (Patent Literature 2), a method of using a metal multilayer thin film (Patent Literature 3), and the like are disclosed.

CITATION LIST

Patent Literature

Patent Literature 1: Japanese Patent Application Laid-Open No. 2009-192931
Patent Literature 2: Japanese National-Phase Publication No. 2006-508538
Patent Literature 3: Japanese Patent Application Laid-Open No. 2008-518446

Non-Patent Literature

Non-Patent Literature 1: Qingfeng Dong et al., Org. Electron., 2010, 11(7), 1327-1331

SUMMARY OF INVENTION

Technical Problem

However, in the methods described in Patent Literatures 1 to 3 and Non-Patent Literature 1 above, it is difficult to simply obtain a photoelectric conversion element exhibiting excellent transparency, photoelectric conversion efficiency, and durability.

In other words, in the method of Patent Literature 1 above, a transparent electrode composed of ITO is also used in the second electrode formed on the functional organic thin film responsible for the photoelectric conversion function. The functional organic thin film having a thin lower part is easily damaged by spattering or the like at the time of forming ITO as the second electrode, and thus it is difficult to obtain an organic photoelectric conversion element excellent in photoelectric conversion efficiency and durability.

Conductivity is still insufficient in the method of using a conductive polymer described in Non-Patent Literature 1 above. According to this publication, it is difficult to obtain a cell having a high fill factor (FF) and short circuit current (Jsc) as the fill factor remains at 47% and the photoelectric conversion efficiency (PCE) remains at 1.9%.

On the other hand, in the method of Patent Literature 2, improvement in conductivity is attempted by combining a conductive polymer and a metal mesh electrode and thus conductivity and transparency are secured. However, it is necessary to form a film of a patterned thin metallic wire conductive polymer and thus the manufacturing process is complicated.

In the method of using a metal thin film described in Patent Literature 3 above, conductivity and transparency are in a trade-off relation, and thus it is difficult to achieve both high transparency and excellent photoelectric conversion efficiency.

Accordingly, an object of the present invention is to provide a transparent electrode (transparent conductive film) having a simple manufacturing process, high transparency, high photoelectric conversion efficiency, and excellent durability and an organic photoelectric conversion element (particularly, a semi-transparent type (see-through type) organic photoelectric conversion element) using the same.

Solution to Problem

The present inventors have conducted extensive studies in order to solve the above problems. As a result, it has been found out that a transparent conductive film exhibiting both high conductivity and high transparency can be simply obtained by forming a metal thin film layer on a ground layer containing a nitrogen-containing organic compound. In other words, it has been found out that it is possible to forma continuous film even in the case of forming a metal thin film layer having a significantly thin film thickness by using an organic thin film consisting of a nitrogen-containing organic compound exhibiting high coordination ability with respect to a metal as a ground layer, and thus it is possible to achieve both high conductivity and high transparency. In addition, it has been found out that it is possible to provide an organic photoelectric conversion element (particularly, a semi-transparent type (see-through type) organic photoelectric conversion element) exhibiting favorable photoelectric conversion efficiency and durability by using the transparent conductive film as an electrode.

In other words, according to an aspect of the present invention, it is provided a transparent conductive film including a ground layer which contains a nitrogen-containing organic compound and a metal thin film layer which is formed on the ground layer, contains a transition metal element of Group 11 of the periodic table, and has a thickness of from 2 to 10 nm.

Moreover, according to another aspect of the present invention, it is provided an organic photoelectric conversion element including a first electrode, a second electrode, and a photoelectric conversion layer present between the first electrode and the second electrode, in which at least one of the first electrode and the second electrode is a transparent conductive film formed by laminating a ground layer which contains a nitrogen-containing organic compound and a metal thin film layer which contains a metal element of Group 11 of the periodic table and has a thickness of from 2 to 10 nm.

Effect of the Invention

According to the present invention, it is possible to provide a transparent conductive film exhibiting improved conductivity as a transparent electrode by a simple method while maintaining high transparency as a thin film.

Moreover, it is possible to provide a semi-transparent type (see-through type) organic photoelectric conversion element capable of exerting sufficient photoelectric conversion efficiency and durability in the case of constituting an organic photoelectric conversion element using the transparent conductive film.

DESCRIPTION OF EMBODIMENTS

Figure 1:
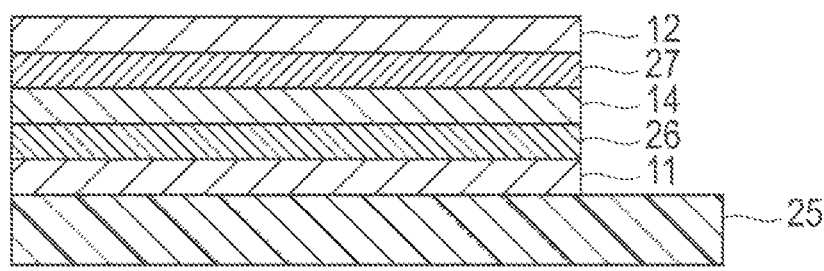
FIG. 1 is a cross-sectional schematic view schematically illustrating a forwardly layered type organic photoelectric conversion element according to an embodiment of the present invention.

An aspect of the present invention is a transparent conductive film including a ground layer which contains a nitrogen-containing organic compound and a metal thin film layer which is formed on the ground layer, contains a transition metal element of Group 11 of the periodic table, and has a thickness of from 2 to 10 nm. In addition, another aspect of the present invention is a transparent conductive film including a ground layer which contains a nitrogen-containing organic compound and a metal thin film layer which is formed on the ground layer, contains a transition metal element of Group 11 of the periodic table, and has a thickness of from 10 to 30 nm.

The transparent conductive film of the present invention has a feature in that the metal thin film layer is formed on the ground layer containing a nitrogen-containing organic compound. It is possible to form a continuous metal thin film layer having a significantly thin film thickness by using an organic thin film containing a nitrogen-containing organic compound exhibiting high coordination ability with respect to a metal as a ground layer, and as a result, a transparent conductive film exhibiting both high conductivity and high transparency can be simply obtained. Moreover, an organic photoelectric conversion element exhibiting favorable photoelectric conversion efficiency and durability can be obtained by using the transparent conductive film as an electrode. Here, the mechanism of the above effect exerted by the organic photoelectric conversion element of the present invention is not clear but presumed as follows. However, the present invention is not limited to the following presumption.

In general, a metal thin film is easily isolated in an island shape by the nucleus growth type (Volumer-Weber: VW type) film growth. In other words, a substrate commonly used for film formation exhibits weak coordination ability to the metal and thus the fine metallic particles come flying from the deposition source are able to move (diffuse) for a while even after attached to the substrate, and thus the metal fine particles collide, fuse, and adhere to each other during the time to be in a state in which isolated metal islands are arranged in a line, that is, a state in which the aggregated metal particles are present in a patchy shape. The metal film having the island structure exhibits a low transmittance and a high sheet resistance and thus cannot be used as an electrode material. On the other hand, the sheet resistance can be reduced but the transparency decreases when the film thickness is increased and thus a transparent electrode cannot be obtained. Consequently, it is difficult to obtain a continuous metal thin film having a thin film thickness by the method of the related art.

On the contrary to this, in the present invention, a uniform metal layer having a significantly thin film thickness is obtained since the metal thin film is formed by a single layer growth type (Frank-van der Merwe: FW type) film growth by the interaction of the metal atom constituting the metal thin film layer with the nitrogen-containing compound constituting the ground layer. Specifically, the kinetic energy of the metal particles attached on the ground layer is reduced by the strong coordination ability of the ground layer to the metal, the diffusion length of the metal atom on the ground layer surface is reduced, and thus the aggregation of the metal is suppressed. As a result, it is possible to form a continuous metal film without isolation having an island shape even in the case of forming into a thin film. By virtue of this, it is possible to obtain a favorable transparent conductive film exhibiting improved conductivity while maintaining the transparency (visible light transmittance) exhibited by forming into a thin film. In addition, it is possible to obtain a semi-transparent type (see-through type) organic photoelectric conversion element (organic thin film solar cell) exhibiting favorable power generation efficiency and durability by using the transparent conductive film as an electrode material. In particular, in the organic photoelectric conversion element, it is possible to prevent the damage of the photoelectric conversion layer caused by the film formation of the electrode material since the metal thin film layer (electrode layer) is formed via the ground layer containing a nitrogen-containing compound. Moreover, the organic photoelectric conversion element can achieve high power generation efficiency and durability even in the case of having a constitution in which the ground layer containing a nitrogen-containing organic compound is present between the metal thin film layer and the photoelectric conversion layer.

Meanwhile, in the present specification, the term "conductivity" means that the surface resistivity (sheet resistance) is 100 Ω/square or less, and the surface resistivity is preferably 50 Ω/square or less, more preferably 30 Ω/square or less, even more preferably 20 Ω/square or less, and particularly preferably 10 Ω/square or less. Hence, it is possible for a solar cell to have a higher fill factor (FF) as the sheet resistance of the electrode is lower. The surface resistivity can be measured using a 4-terminal 4-probe method based on JIS-K7194:1994 by, for example, the Loresta GP•MCP-T610 manufactured by Mitsubishi Chemical Corporation.

In addition, in the present specification, the "transparency (visible light transmissive)" means that the transmittance of light having a wavelength of 550 nm is 60% or more, and the transmittance is preferably 70% or more, more preferably 80% or more, even more preferably 85% or more, and particularly preferably 90% or more. The transmittance of the light having a wavelength of 550 nm can be measured using a spectrophotometer (for example, U-4000 model manufactured by Hitachi, Ltd.).

Hereinafter, embodiments of the present invention will be described with reference to the accompanying drawings. However, the technical scope of the present invention should be defined based on the description of the appended claims, but are not limited to the following embodiments. Meanwhile, the same reference numerals are given to the same elements, and overlapping description will not be presented in the description of the drawings. In addition, the dimensional ratios in the drawings are exaggerated for convenience of explanation and may be different from the actual ratios.

First, the basic constitution of the organic photoelectric conversion element to which the transparent conductive film according to the present embodiment may be applied will be described with reference to the drawings. An embodiment of the present invention is an organic photoelectric conversion element including a first electrode, a second electrode, and a photoelectric conversion layer present between the first electrode and the second electrode. In addition, the organic photoelectric conversion element is characterized in that at least one of the first electrode and the second electrode is a transparent conductive film formed by laminating a ground layer containing a nitrogen-containing organic compound and a metal thin film layer containing a metal element of Group 11 of the periodic table and having a thickness of from 2 to 10 nm or from 10 to 30 nm.

[Constitution of the Organic Photoelectric Conversion Element]

(Forwardly Layered Type Organic Photoelectric Conversion Element)

FIG. 1 is a cross-sectional schematic view schematically illustrating a forwardly layered type organic photoelectric conversion element according to an embodiment of the present invention.

The organic photoelectric conversion element 10 of FIG. 1 has a constitution in which a cathode (first electrode) 11, a hole transport layer 26, a photoelectric conversion layer 14, an electron transport layer 27, and an anode (second electrode) 12 are laminated on a substrate 25 in this order. In the present embodiment, the photoelectric conversion layer 14 is preferably constituted to contain a p-type organic semiconductor material and an n-type organic semiconductor material. Meanwhile, the substrate 25 is a member provided arbitrarily to facilitate mainly the formation of the cathode (first electrode) 11 thereon by a coating method.

At the time of operating the organic photoelectric conversion element 10 illustrated in FIG. 1, light is irradiated from the substrate 25 side. The light irradiated from the substrate 25 side passes through the cathode 11 and the hole transport layer 26 and then reaches the photoelectric conversion layer 14. When this light is incident on the photoelectric conversion layer 14, an electron in the p-type organic semiconductor material is excited from the highest occupied molecular orbital (hereinafter, referred to as "HOMO") to the lowest unoccupied molecular orbital (hereinafter, referred to as "LUMO") and thus an exciton is generated, diffuse, and reaches the interface with the n-type organic semiconductor, and then the electron at the LUMO level of the p-type organic semiconductor material moves to the LUMO level of the n-type organic semiconductor material to cause charge separation, whereby a hole is generated at the HOMO level of the p-type organic semiconductor and an electron is generated at the LUMO level of the n-type organic semiconductor. Subsequently, this electron moves to the conduction band of the n-type organic semiconductor material. Thereafter, the electron passes through the electron transport layer 27 and the anode 12 and then moves to the valence band of the p-type organic semiconductor material through the external circuit. In other words, the hole generated at the HOMO level of the p-type organic semiconductor material passes through the hole transport layer 26 and the cathode 11 and then moves to the conduction band of the n-type organic semiconductor material through the external circuit. In this manner, light current flows between the cathode 11 and the anode 12, whereby power generation is performed.

In the present invention, it is particularly preferable to use a bulk heterojunction type photoelectric conversion layer 14 (not illustrated in the drawing) in which a p-type organic semiconductor material and an n-type organic semiconductor material are uniformly mixed since it is believed that such photoelectric charge separation is promoted as the contact interface between the p-type organic semiconductor material and the n-type organic semiconductor material is larger. However, it is not limited to only such a form.

Meanwhile, the hole transport layer 26 is formed of a material having high hole mobility and has a function to efficiently transport the hole generated at the pn junction interface of the photoelectric conversion layer 14 to the cathode (transparent electrode) 11. On the other hand, the electron transport layer 27 is formed of a material having high electron mobility and has a function to efficiently transport the electron generated at the pn junction interface of the photoelectric conversion layer 14 to the anode (counter electrode) 12. The hole transport layer 26 and the electron transport layer 27 are arbitrary members provided if necessary.

Figure 2:
FIG. 2 is a cross-sectional schematic view illustrating a basic constitution of a transparent conductive film according to an embodiment of the present invention.
Figure 3:
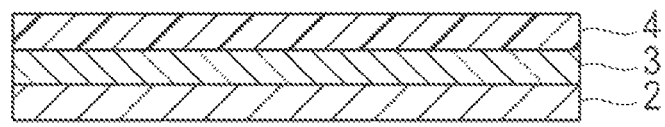
FIG. 3 is a cross-sectional schematic view illustrating a basic constitution of a transparent conductive film according to an embodiment of the present invention.

In the organic photoelectric conversion element 10 of the embodiment illustrated in FIG. 1, at least one of the first electrode and the second electrode is constituted with a transparent conductive film formed by laminating a ground layer containing a nitrogen-containing organic compound and a metal thin film layer. The basic constitution of the transparent conductive film as a transparent electrode according to an embodiment of the present invention is illustrated in FIG. 2 and FIG. 3. In an embodiment of the present invention, the first electrode 11 as a cathode is a transparent conductive film 1A having a form illustrated in FIG. 2 and the second electrode 12 as an anode is a transparent conductive film 1B having a form illustrated in FIG. 3.

As illustrated in FIG. 2, the transparent electrode 1A is formed by laminating a metal thin film layer 3 on a ground layer 2. Usually, the organic photoelectric conversion element 10 illustrated in FIG. 1 is formed by laminating the cathode (first electrode) 11, the hole transport layer 26, the photoelectric conversion layer 14, the electron transport layer 27, and the anode (second electrode) 12 on the substrate 25 in order, and thus the transparent conductive film 1A as the cathode (first electrode) 11 is formed by laminating the ground layer 2 and the metal thin film layer 3 on the substrate 25 in order. Hence, the transparent conductive film 1A is formed between the substrate 25 and the hole transport layer 26 in FIG. 1 such that the ground layer 2 is positioned on the substrate 25 side and the metal thin film layer 3 is positioned on the hole transport layer 26 side.

As illustrated in FIG. 3, the transparent conductive film 1B has a constitution in which the metal thin film layer 3 is laminated on the ground layer 2 and a protective layer 4 is further provided on the metal thin film layer 3. By providing the protective layer 4 on the metal thin film layer 3, it is possible to suppress the reflection of sunlight on the surface of the metal thin film layer and thus the quantity of light absorbed by the photoelectric conversion layer 14 increases, as a result, the photoelectric conversion efficiency can be improved. However, the protective layer 4 is an arbitrary layer provided if necessary, and it is also possible to use the transparent conductive film 1A in the form which is not provided with the protective layer 4 as illustrated in FIG. 2 as the second electrode 12 as the anode.

Usually, the organic photoelectric conversion element 10 illustrated in FIG. 1 is formed by laminating the cathode (first electrode) 11, the hole transport layer 26, the photoelectric conversion layer 14, the electron transport layer 27, and the anode (second electrode) 12 on the substrate 25 in order, and thus the transparent conductive film 1B as the anode (second electrode) 12 is formed such that the protective layer 4 is positioned on the outermost layer side of the organic photoelectric conversion element 10 and the ground layer 2 is positioned on the electron transport layer 27 side. Here, the ground layer according to the present invention is excellent in electron transport property and can function as an electron transport layer. Accordingly, in the case of using the transparent conductive film illustrated in FIG. 2 or FIG. 3 as the anode (second electrode) 12 of the forwardly layered type organic photoelectric conversion element 10 as illustrated in FIG. 1, the ground layer can exert a function as an electron transport layer and the electron transport layer 27 can be omitted, thus it is possible to form the ground layer directly on the photoelectric conversion layer 14.

Meanwhile, it is also possible to use the transparent conductive film 1B illustrated in FIG. 3 as the first electrode 11 as the cathode. However, it is not preferable to dispose the protective layer that does not contribute to the photoelectric conversion between the cathode and the photoelectric conversion layer in terms of improving the transport efficiency of the hole but it is preferable to use the transparent conductive film 1A as the first electrode 11.

In the present embodiment, both the first electrode and the second electrode are constituted with transparent conductive films (1A, 1B) having a laminate structure of the ground layer 2 and the metal thin film layer 3, but the present invention is not limited to the corresponding embodiment, and it is sufficient that at least one of the first electrode and the second electrode is a transparent conductive film. It is preferable that at least the second electrode is the transparent conductive film according to the present invention. This is because the ground layer can also serve as the electron transport layer 27 in the case of using the transparent conductive film of the present invention as the second electrode 12 since the ground layer containing a nitrogen-containing organic compound has a property as an electron transport layer.

In addition, in a case in which only one of the first electrode and the second electrode is the transparent conductive film, the other electrode which is not the transparent conductive film is not necessarily transparent and may be constituted with an electrode material which is not transparent or an electrode material which is transparent. However, it is preferable to constitute the cathode 11 with a transparent electrode material (the transparent conductive film above or another electrode material (for example, ITO)) so that the irradiated light efficiently reaches the photoelectric conversion layer 14 since the light is irradiated from the substrate 25 side at the time of operating the organic photoelectric conversion element 10. In addition, the substrate 25 is not necessarily transparent but may be an opaque metal foil or the like in a case in which the second electrode (anode) is transparent. The organic photoelectric conversion element 10 is a semi-transparent type (see-through type) organic thin film solar cell in a case in which all of the substrate 25, the cathode (first electrode) 11, and the anode (second electrode) 12 are a transparent material.

(Reversely Layered Type Organic Photoelectric Conversion Element)

Figure 4:
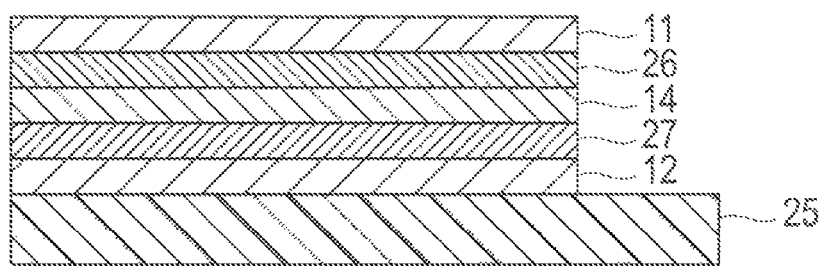
FIG. 4 is a cross-sectional schematic view schematically illustrating a reversely layered type organic photoelectric conversion element according to another embodiment of the present invention.

FIG. 4 is a cross-sectional schematic view schematically illustrating a reversely layered type organic photoelectric conversion element according to another embodiment of the present invention. An organic photoelectric conversion element 20 of FIG. 4 is different in that the cathode 11 and the anode 12 are disposed at the opposite positions and the hole transport layer 26 and the electron transport layer 27 are disposed at the opposite positions as compared to the organic photoelectric conversion element 10 of FIG. 1. In other words, the reversely layered type organic photoelectric conversion element is characterized in that the first electrode is the anode 12, the second electrode is the cathode (counter electrode) 11, and the hole transport layer 26 is included between the second electrode and the photoelectric conversion layer 14. The organic photoelectric conversion element 20 of FIG. 4 has a constitution in which the anode 12, the electron transport layer 27, the photoelectric conversion layer 14, the hole transport layer 26, and the cathode (counter electrode) 11 are laminated on the substrate 25 in this order. By having such a constitution, the electron generated at the pn junction interface of the photoelectric conversion layer 14 is transported to the anode 12 through the electron transport layer 27 and the hole is transported to the cathode (counter electrode) 11 through the hole transport layer 26.

In the present embodiment, at least of the first electrode (anode) 12 and the second electrode (cathode) 11 is the above transparent conductive film 1A or 1B. As a preferred embodiment, the transparent conductive film 1A which is not provided with a protective layer is used as the first electrode (anode) 12 in terms of improving the transport efficiency of the electron. In addition, it is preferable that the transparent conductive film 1B which is provided with the protective layer 4 is used as the second electrode (cathode) 11 from the viewpoint of suppressing the reflection of sunlight on the surface of the metal thin film layer, increasing the quantity of light absorbed by the photoelectric conversion layer 14, and thus improving the photoelectric conversion efficiency. In the present embodiment as well, both the first electrode (anode) 12 and the second electrode (cathode) 11 may be the above transparent conductive film 1A or 1B or only either of them may be the above transparent conductive film 1A or 1B. It is preferable that the first electrode is the transparent conductive film according to the present invention. This is because the ground layer can also serve as the electron transport layer 27 in the case of using the transparent conductive film of the present invention as the first electrode 12 since the ground layer containing a nitrogen-containing organic compound has a property as an electron transport layer. However, the second electrode may be the transparent conductive film according to the present invention. The other electrode which is not the transparent conductive film is not necessarily transparent in a case in which only one of the first electrode and the second electrode is the transparent conductive film. However, it is preferable to constitute the first electrode (anode) 12 with a transparent electrode material so that the irradiated light efficiently reaches the photoelectric conversion layer 14 since the light is irradiated from the substrate 25 side at the time of operating the organic photoelectric conversion element 10. In addition, the substrate 25 is not necessarily transparent but may be an opaque metal foil or the like in a case in which the second electrode (cathode) is transparent. The organic photoelectric conversion element 20 is a semi-transparent type (see-through type) organic thin film solar cell in a case in which all of the substrate 25, the anode (first electrode) 11, and the cathode (second electrode) 12 are a transparent material.

Figure 5:
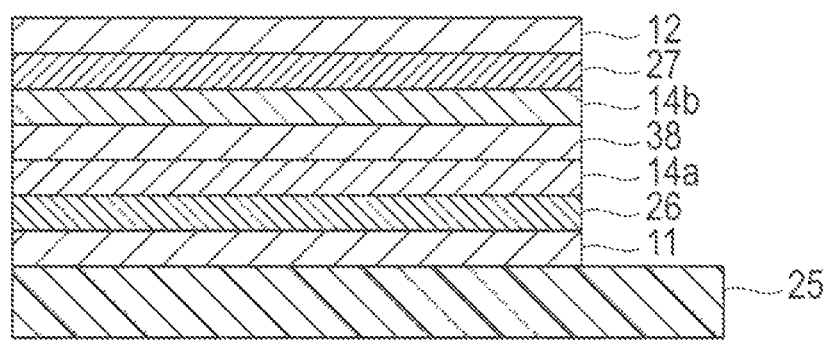
FIG. 5 is a cross-sectional schematic view schematically illustrating an organic photoelectric conversion element equipped with a tandem type photoelectric conversion layer according to another embodiment of the present invention.

FIG. 5 is a cross-sectional schematic view schematically illustrating an organic photoelectric conversion element equipped with a forwardly layered tandem type (multi-junction type) photoelectric conversion layer according to another embodiment of the present invention. An organic photoelectric conversion element 30 of FIG. 5 is different in that a laminate body of a first photoelectric conversion layer 14a, a second photoelectric conversion layer 14b, and a charge recombination layer 38 interposed between these two photoelectric conversion layers is disposed instead of the photoelectric conversion layer 14 as compared to the organic photoelectric conversion element 10 of FIG. 1. In the tandem type organic photoelectric conversion element 30 illustrated in FIG. 5, it is possible to efficiently convert light in a wider wavelength region into electricity by using photoelectric conversion materials (a p-type organic semiconductor and an n-type organic semiconductor) having different absorption wavelengths in the first photoelectric conversion layer 14a and the second photoelectric conversion layer 14b, respectively.

Meanwhile, a reversely layered tandem type (multi-junction type) photoelectric conversion element is obtained when the cathode 11 and the anode 12 are disposed at opposite positions, the hole transport layer 26 and the electron transport layer 27 are disposed at opposite positions, and first photoelectric conversion layer 14a and a second photoelectric conversion layer 14b are disposed at opposite positions in the organic photoelectric conversion element 30 illustrated in FIG. 5.

In the tandem type organic photoelectric conversion element 30, the transparent conductive film of the present embodiment can be used in any of the first electrode (cathode) 11, the second electrode (anode) 12, and further the charge recombination layer 38. In other words, at least one of these is the above transparent conductive film 1A or 1B. In the tandem type organic photoelectric conversion element described above as well, the substrate 25 is not necessarily transparent but may be an opaque metal foil or the like in a case in which the second electrode is transparent. The tandem type organic photoelectric conversion element 30 is a semi-transparent type (see-through type) organic thin film solar cell in a case in which all of the substrate 25, the first electrode 11, and the second electrode 12 are a transparent material.

Among the embodiments described above, the organic photoelectric conversion element of the present invention is preferably the forwardly layered type organic photoelectric conversion element illustrated in FIG. 1 or the forwardly layered tandem type organic photoelectric conversion element illustrated in FIG. 5. This is because the ground layer can also serve as the electron transport layer 27 in the case of using the transparent conductive film of the present invention as the second electrode 12 in the forwardly layered type organic photoelectric conversion element since the ground layer which constitutes the transparent conductive film and contains a nitrogen-containing organic compound has a property as an electron transport layer.

Hereinafter, each constitution of the organic photoelectric conversion element according to the present invention will be described in detail.

[Electrode]

The organic photoelectric conversion element of the present embodiment essentially includes a cathode and an anode. The transparent conductive film of the present invention may be used as either one of the cathode and the anode, that is, the other electrode may be formed using an electrode material known in the related art.

The case of a forwardly layered type organic photoelectric conversion element which is a preferred embodiment of the present invention will be described below, but in the case of a reversely layered type organic photoelectric conversion element, everything is the same as those of the forwardly layered type organic photoelectric conversion element except that the constitution of electrodes is reversed.

(Transparent Conductive Film)

At least one of the first electrode and the second electrode is a transparent conductive film formed by laminating a ground layer and a metal thin film layer. The present invention is characterized in that a transparent conductive film 1 has a ground layer 2 which contains a nitrogen-containing organic compound and a metal thin film layer 3 which is formed on the ground layer 2, contains a transition metal element of Group 11 of the periodic table, and has a thickness of from 2 to 10 nm or from 10 to 30 nm as illustrated in FIG. 2 or FIG. 3.

(Ground Layer)

The ground layer 2 is constituted to contain a nitrogen-containing organic compound. The ground layer 2 functions as the ground at the time of forming the metal thin film layer 3, and has an effect of reducing the diffusion length of a metal atom as an electrode material and thus suppressing the aggregation of the metal. The metal thin film layer 3 can be formed in a thin and continuous manner by forming the metal thin film layer 3 on the ground layer 2, as a result, it is possible to obtain a transparent conductive film (transparent electrode) exhibiting secure conductivity while maintaining the light transmittance even at a thin film thickness. Moreover, the ground layer 2 that is constituted to contain a nitrogen-containing compound can achieve high power generation efficiency and durability even present between the photoelectric conversion layer 14 and the metal thin film layer 3 that is responsible for conductivity.

The nitrogen-containing organic compound is not particularly limited as long as it is an organic compound having a nitrogen atom-containing group in the molecule. A nitrogen atom-containing group exhibits strong interaction with a metal atom and thus confines the metal atom at the time of forming the metal thin film layer so as to allow the single layer growth type (FW type) film growth.

Moreover, such a nitrogen-containing organic compound is excellent in electron transport property. Hence, a ground layer containing a nitrogen-containing organic compound can function as an electron transport layer in a case in which the ground layer is positioned between an anode and a photoelectric conversion layer, and in such a case, excellent photoelectric conversion efficiency can be exerted even though an electron transport layer is not provided.

The nitrogen-containing organic compound may be a low molecular weight compound or a polymer compound but preferably has a structure facilitating the interaction with a metal atom at the time of forming a metal thin film layer. For example, the nitrogen-containing organic compound preferably contains a compound represented by the following Formula (1), or a polymer compound having a partial structure represented by the following Formula (2) or a polymer compound having a partial structure represented by the following Formula (3).

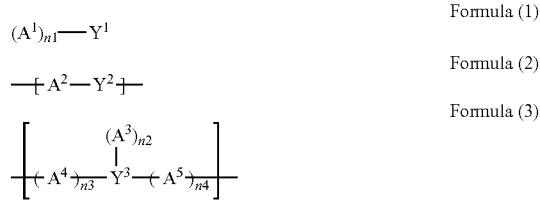

In Formula (1) above, $A^1$ represents a monovalent nitrogen atom-containing group. n1 represents an integer of 2 or more, preferably an integer of 2 to 4 in terms of sufficient interactivity with a metal atom of Group 11 (a nitrogen-containing group is not buried in the molecule by the steric hindrance but can substantially exert an effect on the interaction with a metal atom), and even more preferably 2 or 3 in terms of easiness of synthesis. The plural $A^1$'s may be the same as or different from each other. $Y^1$ represents an n1-valent organic group or a single bond (—). Meanwhile, n1 is 2 in a case in which $Y^1$ is a single bond (—), and the compound represented by Formula (1) has the structure of $A^1$-$A^1$. At this time, the two $A^1$'s may be the same as or different from each other. In addition, the compound represented by Formula (1) contains 5 or more nitrogen atoms to be effective in the present invention and it is presumed that this effect is attributed to the excellent interaction with the metal thin film. The compound represented by Formula (1) contains more preferably from 5 to 20 nitrogen atoms and even more preferably from 5 to 10 nitrogen atoms.

In Formula (2) above, $A^2$ represents a divalent nitrogen atom-containing group, and $Y^2$ represents a divalent organic group or a single bond (—).

In Formula (3) above, $A^3$ represents a monovalent nitrogen atom-containing group. In addition, n2 represents an integer of 1 or more. n2 is preferably an integer of 1 to 3 in terms of sufficient interactivity with a metal atom of Group 11 and even more preferably 1 or 2 in terms of easiness of synthesis. The plural $A^3$'s may be the same as or different from each other in a case in which n2 is 2 or more. In addition, $A^3$'s may be the same as or different from each other in a case in which plural $A^3$'s are contained in the polymer compound.

In Formula (3) above, $A^4$ and $A^5$ represent a divalent nitrogen atom-containing group. $A^4$ and $A^5$ may be the same as or different from each other. n3 and n4 each independently represent an integer of 0 or 1.

In Formula (3) above, $Y^3$ represents an (n2+2)-valent organic group.

A preferred embodiment is a compound having a nitrogen atom-containing group not in the central portion of the nitrogen-containing organic compound but in the peripheral portion thereof and a compound represented by Formula (1) or a polymer compound having a partial structure represented by Formula (3). In such a structure, a nitrogen atom-containing group is present on the surface at a high density at the time of forming the ground layer 2 and thus the interaction (accessibility) thereof with a metal atom increases.

Another preferred embodiment is an embodiment in which the nitrogen-containing organic compound is a polymer compound, that is, a polymer compound having a partial structure represented by Formula (2) or (3). The ground layer containing a nitrogen-containing organic compound is usually formed by a coating method. This is because the uniformity of film quality is high in the case of a polymer compound and an organic photoelectric conversion element excellent in photoelectric conversion efficiency and durability is obtained.

The polymer compound having a partial structure represented by Formula (2) or (3) above as the nitrogen-containing organic compound may be a homopolymer composed of only a single constitutional unit derived from Formula (2) or (3) above or a copolymer composed of only two or more constitutional units derived from Formula (2) and/or (3) above. In addition, the polymer compound may be a copolymer formed by further having another structural unit which does not have a nitrogen-containing substituent (hereinafter, also simply referred to as "another structural unit") in addition to the structural units represented by Formula (2) or (3) above. In a case in which the nitrogen-containing organic compound has another structural unit, the content of another structural unit is not particularly limited as long as the content is at the degree at which the effect by the nitrogen-containing organic compound according to the invention is not impaired, and the content of a monomer derived from another structural unit is preferably from 10 to 75% by mole and more preferably from 20 to 50% by mole in the monomers derived from all structural units.

The terminal of the polymer compound having a partial structure represented by Formula (2) or (3) above as the nitrogen-containing organic compound is not particularly limited and is appropriately determined depending on the kind of the raw material (monomer) used but is usually a hydrogen atom.

In Formula (1) or (3) above, the monovalent nitrogen atom-containing group represented by $A^1$ or $A^3$ is not particularly limited as long as it is an organic group containing a nitrogen atom. Examples thereof may include an amino group, a dithiocarbamate group, a thioamide group, a cyano group (—CN), an isonitrile group (—$N^+$≡$C^-$), an isocyanate group (—N═C═O), a thioisocyanate group (—N═C═S), or a group containing a substituted or unsubstituted nitrogen-containing aromatic ring.

Examples of the nitrogen-containing aromatic ring may include an aziridine ring, an azirine ring, an azetidine ring, an azete ring, an azolidine ring, an azole(pyrrole) ring, an azinane ring, a pyridine ring, an azepane ring, an azepine ring, an imidazole ring, a pyrazole ring, a triazole ring, an oxazole ring, an oxadiazole ring, a triazole ring, an imidazoline ring, a pyrazine ring, a morpholine ring, a thiazine ring, an indole ring, an isoindole ring, a benzimidazole ring, a purine ring, a quinoline ring, an isoquinoline ring, a quinoxaline ring, a cinnoline ring, a pteridine ring, an acridine ring, a carbazole ring, a carboline ring, a diazacarbazole ring (also referred to as monoazacarboline, and indicating a ring constitution in which one of the carbon atoms constituting the carboline is substituted with a nitrogen atom), a phenanthridine ring, an acridine ring, a phenanthroline ring, a phenazine ring, a benzo-C-cinnoline ring, a porphyrin ring, a chlorin ring, and a corrin ring. As the group containing a nitrogen-containing aromatic ring, a plurality of these nitrogen-containing aromatic rings may be used in combination. At this time, the plurality of nitrogen-containing aromatic rings may be directly bonded or via a divalent linking group. In addition, a plurality of nitrogen-containing aromatic rings may form a condensed ring.

Here, in a case in which the nitrogen-containing aromatic ring has a substituent, the substituent is not particularly limited. Examples thereof may include an alkyl group (for example, a methyl group, an ethyl group, a propyl group, an isopropyl group, a n-butyl group, a sec-butyl group, a tert-butyl group, a pentyl group, a hexyl group, an octyl group, a dodecyl group, a tridecyl group, a tetradecyl group, a pentadecyl group, or the like), a cycloalkyl group (for example, a cyclopentyl group, a cyclohexyl group, or the like), an alkenyl group (for example, a vinyl group, an allyl group, a 1-propenyl group, a 2-butenyl group, a 1,3-butadienyl group, a 2-pentenyl group, an isopropenyl group, or the like), an alkynyl group (for example, an ethynyl group, a propargyl group, or the like), an aromatic hydrocarbon group (also referred to as an aromatic hydrocarbon ring group, an aromatic carbocyclic group, an aryl group, or the like, and for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, a biphenyl group, or the like), an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolinyl group, a diazacarbazolyl group (indicating a group in which one of the arbitrary carbon atoms constituting the carboline ring of the carbolinyl group is substituted with a nitrogen atom), a phthalazinyl group, or the like), a heterocyclic group (for example, a pyrrolidyl group, an imidazolidyl group, a morpholyl group, an oxazolidyl group, or the like), an alkoxy group (for example, a methoxy group, an ethoxy group, a propyloxy group, a pentyloxy group, a hexyloxy group, an octyloxy group, a dodecyloxy group, or the like), a cycloalkoxy group (for example, a cyclopentyloxy group, a cyclohexyloxy group, or the like), an aryloxy group (for example, a phenoxy group, a naphthyloxy group, or the like), an alkylthio group (for example, a methylthio group, an ethylthio group, a propylthio group, a pentylthio group, a hexylthio group, an octylthio group, a dodecylthio group, or the like), a cycloalkylthio group (for example, a cyclopentylthio group, a cyclohexylthio group, or the like), an arylthio group (for example, a phenylthio group, a naphthylthio group, or the like), an alkoxycarbonyl group (for example, a methyloxycarbonyl group, an ethyloxycarbonyl group, a butyloxycarbonyl group, an octyloxycarbonyl group, a dodecyloxycarbonyl group, or the like), an aryloxycarbonyl group (for example, a phenyloxycarbonyl group, a naphthyloxycarbonyl group, or the like), a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, a 2-pyridylaminosulfonyl group, or the like), an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, a pyridylcarbonyl group, or the like), an acyloxy group (for example, an acetyloxy group, an ethylcarbonyloxy group, a butylcarbonyloxy group, an octylcarbonyloxy group, a dodecylcarbonyloxy group, a phenylcarbonyloxy group, or the like), an amide group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, a naphthylcarbonylamino group, or the like), a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, a 2-pyridylaminocarbonyl group, or the like), a ureido group (for example, a methylureido group, an ethylureido group, a pentylureido group, a cyclohexylureido group, an octylureido group, a dodecylureido group, a phenylureido group, a naphthylureido group, a 2-pyridylaminoureido group, or the like), a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, a 2-pyridylsulfinyl group, or the like), an alkylsulfonyl group (for example, a methylsulfonyl group, an ethylsulfonyl group, a butylsulfonyl group, a cyclohexylsulfonyl group, a 2-ethylhexylsulfonyl group, a dodecylsulfonyl group, or the like), an arylsulfonyl group or a heteroarylsulfonyl group (for example, a phenylsulfonyl group, a naphthylsulfonyl group, a 2-pyridylsulfonyl group, or the like), an amino group (for example, an amino group, an ethylamino group, a dimethylamino group, a butylamino group, a cyclopentylamino group, a 2-ethylhexylamino group, a dodecylamino group, an anilino group, a naphthylamino group, a 2-pyridylamino group, or the like), a halogen atom (for example, a fluorine atom, a chlorine atom, a bromine atom, or the like), a fluorinated hydrocarbon group (for example, a fluoromethyl group, a trifluoromethyl group, a pentafluoroethyl group, a pentafluorophenyl group, or the like), a cyano group, a nitro group, a hydroxyl group, a mercapto group, a silyl group (for example, a trimethylsilyl group, a triisopropylsilyl group, a triphenylsilyl group, a phenyldiethylsilyl group, or the like), a phosphono group, and the like, and a polymerizable group (for example, an acryloyl group, a methacryloyl group, an epoxy group, an oxetane group, an isocyanate group, an alkoxysilane group, or the like). Meanwhile, in the above, a substituent cannot be substituted with the same substituent. In other words, a substituted alkyl group (alkylene group), cannot be substituted with an alkyl group. Among these, a substituent is preferably an alkyl group (for example, a methyl group, an ethyl group, a propyl group, or the like) and an amino group, and more preferably a methyl group, an amino group, and a dimethylamino group. These substituents may be further substituted with the substituents described above. In addition, a plurality of these substituents may be bonded to one another to form a ring.

In addition, one or more of the hydrogen atoms in the nitrogen-containing aromatic ring may be substituted with an amino group, a dithiocarbamate group, a thioamide group, a cyano group, an isonitrile group, an isocyanate group, or a thioisocyanate group. Moreover, an amino group, a dithiocarbamate group, a thioamide group, a cyano group, an isonitrile group, an isocyanate group, or a thioisocyanate group and the nitrogen-containing aromatic ring may be bonded via a divalent linking group.

The divalent linking group is not particularly limited and examples thereof may include a substituted or unsubstituted alkylene group having from 1 to 20 carbon atoms, a substituted or unsubstituted cycloalkylene group having from 3 to 20 carbon atoms, a substituted or unsubstituted arylene group having from 6 to 30 carbon atoms, a substituted or unsubstituted heteroarylene group having from 1 to 30 carbon atoms, a substituted or unsubstituted alkyleneoxy group having from 1 to 20 carbon atoms, and an imino group.

Here, the unsubstituted alkylene group having from 1 to 20 carbon atoms is not particularly limited and is a linear or branched alkylene group having from 1 to 20 carbon atoms. Examples thereof may include a methylene group, an ethylene group, a trimethylene group, a tetramethylene group, a propylene group, an ethylethylene group, a pentamethylene group, a hexamethylene group, a heptamethylene group, and an octamethylene group. Among these, a linear or branched alkylene group having from 1 to 15 carbon atoms is preferable and a linear or branched alkylene group having from 1 to 12 carbon atoms is more preferable.

The unsubstituted cycloalkylene group having from 3 to 20 carbon atoms is not particularly limited and examples thereof may include a cyclopentylene group, a cyclohexylene group, and a cycloheptylene group.

The arylene group having from 6 to 30 carbon atoms is not particularly limited and examples thereof may include an o-phenylene group, a m-phenylene group, a p-phenylene group, a fluorenediyl group, a naphthalenediyl group, an anthracenediyl group, a naphthacenediyl group, a pyrenediyl group, a naphthyl naphthalenediyl group, a biphenyldiyl group (for example, a [1,1'-biphenyl]-4,4'-diyl group, a 3,3'-biphenyldiyl group, a 3,6-biphenyldiyl group, or the like), a terphenyldiyl group, a quaterphenyldiyl group, a quinquephenyldiyl group, a sexiphenyldiyl group, a septiphenyldiyl group, an octylphenyldiyl group, a nobiphenyldiyl group, and a deciphenyldiyl group.

The unsubstituted heteroarylene group having from 1 to 30 carbon atoms is not particularly limited and examples thereof may include a divalent group derived from the group consisting of a heterocycle not containing a nitrogen atom such as furan, thiophene, benzofuran, dibenzofuran, benzothiophene, dibenzothiophene, benzodithiophene, dithienopyrrole, silafluorene, dithienosilacyclopentadiene, dithienocyclopentadiene, chromone, and indandione; and a heteroaromatic ring containing a nitrogen atom (nitrogen-containing aromatic ring) such as pyridine, pyrimidine, pyrazine, triazine, carbazole, carboline, diazacarbazole, pyrrole, quinoline, isoquinoline, quinolone, isoquinolone, piperidine, coumarin, benzimidazole, benzimidazolone, benzoxazole, benzoisoxazole, benzoxazolone, benzothiazole, benzothiazolethione, benzothiazolone, benzoisothiazolone, indole, carbazole, pyrazole, imidazole, oxazole, isoxazole, thiazole, isothiazole, indazole, pyridazine, cinnoline, quinazoline, quinazolone, quinoxaline, quinoxalone, phthalazine, acridine, acridone, benzoxazinedione, benzoxazinones, naphthalidine, naphtholactam, quinazolinediones, quinoxalinedione, phthalazinedione, pyridone, phthalazone, phthalamidine, naphthalimidine, and dioxopyrimidine.

The unsubstituted alkyleneoxy group having from 1 to 20 carbon atoms refers to "—O-alkylene-" or "-alkylene-O—", and the alkylene group in this case is an alkylene group having from 1 to 20 carbon atoms. Here, the alkylene group having from 1 to 20 carbon atoms is not particularly limited and examples thereof may include the same alkylene groups as those described above. A linear or branched alkylene group having from 1 to 15 carbon atoms is preferable and a linear or branched alkylene group having from 1 to 12 carbon atoms is more preferable. More specific examples thereof may include a divalent group obtained by removing one hydrogen atom from an alkyloxy group such as a methoxy group, an ethoxy group, a propyloxy group, an isopropyloxy group, a butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexyl group, a perfluorooctyl group, a methoxymethyloxy group, or a 2-methoxyethyloxy group.

Here, in a case in which an alkylene group having from 1 to 20 carbon atoms, a cycloalkylene group having from 3 to 20 carbon atoms, an arylene group having from 6 to 30 carbon atoms, a heteroarylene group having from 1 to 30 carbon atoms, or an alkyleneoxy group having from 1 to 20 carbon atoms has a substituent, the substituent is the same as the substituent in the nitrogen-containing aromatic ring described above. Meanwhile, the substituent and the divalent linking group described above cannot be the same. For example, the alkylene group cannot be substituted with an alkyl group.

As the divalent linking group, a substituted or unsubstituted arylene group having from 6 to 18 carbon atoms or heteroarylene group having from 6 to 18 carbon atoms or an imino group, and a substituted or unsubstituted phenylene group, a pyridylene group, or an imino group, or a substituted or unsubstituted divalent group derived from a structure represented by the following Formula (4) is more preferable.

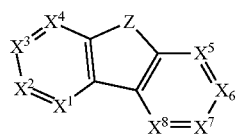

Formula (4)

In Formula (4) above, Z represents —$CR^1R^2$—, —$NR^3$—, —O—, —S—, or —$SiR^4R^5$—.

In Formula (4) above, $X^1$ to $X^8$ each independently represent —$CR^6$= or —N=.

In addition, $R^1$ to $R^6$ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms.

Here, the unsubstituted alkyl group having from 1 to 20 carbon atoms is not particularly limited and is a linear or branched alkyl group having from 1 to 20 carbon atoms, Examples thereof may include a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 1,2-dimethylpropyl group, a n-hexyl group, an isohexyl group, a 1,3-dimethylbutyl group, a 1-isopropylpropyl group, a 1,2-dimethylbutyl group, a n-heptyl group, a 1,4-dimethylpentyl group, a 3-ethylpentyl group, a 2-methyl-1-isopropylpropyl group, a 1-ethyl-3-methylbutyl group, a n-octyl group, a 2-ethylhexyl group, a 3-methyl-1-isopropylbutyl group, a 2-methyl-1-isopropyl group, a 1-t-butyl-2-methylpropyl group, a n-nonyl group, a 3,5,5-trimethylhexyl group, a n-decyl group, an isodecyl group, a n-undecyl group, a 1-methyldecyl group, a n-dodecyl group, a n-hexadecyl group, and a 2-hexyldecyl group. Among these, an alkyl group having from 1 to 12 carbon atoms is preferable and an alkyl group having from 1 to 8 carbon atoms is more preferable from the viewpoint of improving the solubility.

The unsubstituted cycloalkyl group having from 3 to 20 carbon atoms is not particularly limited and examples thereof may include a cyclopropyl group, a cyclopentyl group, a cyclohexyl group, a norbornyl group, and an adamantyl group. Among these, a cycloalkyl group having from 4 to 8 carbon atoms is preferable from the viewpoint of improving the solubility.

The unsubstituted aryl group having from 6 to 30 carbon atoms is not particularly limited and examples thereof may include a non-condensed hydrocarbon group such as a phenyl group, a biphenyl group, and a terphenyl group; and a condensed polycyclic hydrocarbon group such as a pentalenyl group, an indenyl group, a naphthyl group, an azulenyl group, a heptalenyl group, a biphenylenyl group, a fluorenyl group, an acenaphthylenyl group, a pleiadenyl group, an acenaphthenyl group, a phenalenyl group, a phenanthryl group, an anthryl group, a fluoranthenyl group, an acephenantolylenyl group, an aceanthrylenyl group, a triphenylenyl group, a pyrenyl group, a chrysenyl group, or a naphthacenyl group. Among these, a monocyclic aryl group is preferable from the viewpoint of improving the solubility.

The unsubstituted heteroaryl group having from 1 to 30 carbon atoms above is not particularly limited and examples thereof may include a group derived from a heterocycle not containing a nitrogen atom such as a furanyl group (furyl group), a thiophenyl group (thienyl group), a silafluorenyl group, a benzofuranyl group, a dibenzofuranyl group, a benzothiophenyl group, a dibenzothiophenyl group, a dithienopyrrolyl group, benzodithiophenyl group, a dithienosilacyclopentadienyl group, a dithienocyclopentadienyl group, a chromonyl group, or an indadironyl group; or a group derived from a heteroaromatic ring containing a nitrogen atom (a nitrogen-containing aromatic ring) such as a pyridyl group, a pyrimidyl group, a pyrazinyl group, a triazinyl group, a pyrrolyl group, a quinolyl group, a piperidyl group, a coumarinyl group, a benzimidazolyl group, a benzoxazolyl group, a benzothiazolyl group, an indolyl group, a carbazolyl group, a pyrazolyl group, an imidazolyl group, an oxazolyl group, an isoxazolyl group, a thiazolyl group, an isothiazolyl group, an indazolyl group, a benzothiazolyl group, a pyridazinyl group, a cinnolyl group, a quinazolyl group, a quinazolonyl group, a quinoxalyl group, a quinoxalonyl group, a quinazolinedionyl group, a quinoxalinedionyl group, a phthalazinyl group, a phthalazinedionyl group, aphthalazonyl group, aphthalamidyl group, a quinolonyl group, an isoquinolonyl group, an isoquinolinyl group, a benzimidazolonyl group, a benzoxazolonyl group, a benzisoxazolyl group, a benzothiazolonyl group, a benzothiazothionyl group, a benzisothiazolyl group, a naphthalimidyl group, a dioxopyrimidinyl group, an acridinyl group, an acridonyl group, a benzoxazinedionyl group, a benzoxazinonyl group, a pyridonyl group, a naphthyridinyl group, or a naphtholactamyl group. Among these, a monocyclic heteroaryl group is preferable from the viewpoint of improving the solubility.

The unsubstituted alkyloxy group (alkoxy group) having from 1 to 20 carbon atoms is not particularly limited and, for example, a group obtained by bonding an oxygen atom to the scaffold of the alkyl groups exemplified above is mentioned. Specific examples thereof may include a methoxy group, an ethoxy group, a propyloxy group, an isopropyloxy group, a butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethoxy group, a pentafluoroethoxy group, a perfluorobutoxy group, a perfluorohexy group, a perfluoroocty group, a methoxymethyloxy group, and a 2-methoxyethyloxy group. Among these, an alkyloxy group having a branched structure is preferable from the viewpoint of improving the solubility.

In addition, in a case in which the alkyl group having from 1 to 20 carbon atoms, the cycloalkyl group having from 3 to 20 carbon atoms, the aryl group having from 6 to 30 carbon atoms, the heteroaryl group having from 1 to 30 carbon atoms or the alkyloxy group having from 1 to 20 carbon atoms has a substituent, the substituent is the same as the substituent in the nitrogen-containing aromatic ring described above. Meanwhile, in the above, a substituent cannot be substituted with the same substituent. For example, a substituted alkyl group (alkylene group) cannot be substituted with an alkyl group.

The condensed ring structure represented by Formula (4) exhibits high carrier transport property and thus the carrier can be sufficiently transported even in a case in which the ground layer above is in contact with the photoelectric conversion layer or the electron transport layer of the organic photoelectric conversion element, as a result, a decrease in power generation efficiency can be suppressed. Specific examples of the condensed ring structure represented by Formula (4) may include the groups represented by C-1 to C-8 as presented below and the groups represented by N-12 to N-36 to be described below.

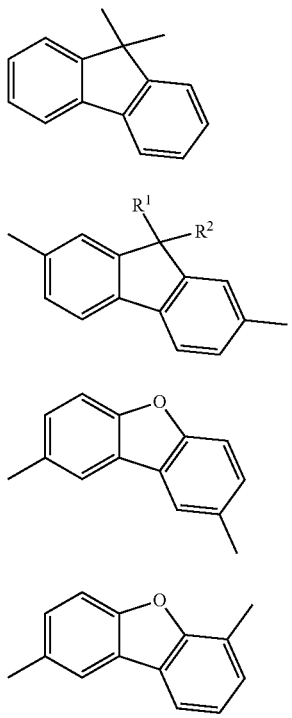

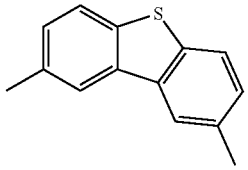

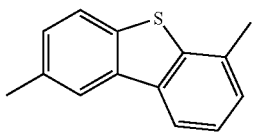

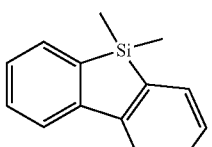

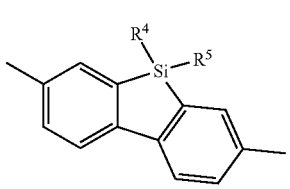

In Formulas above, $R^1$ and $R^2$ and $R^4$ and $R^5$ have the same definition as those in Formula (4).

Among the structures above, those having a fluorene backbone (C-1 and C-2), a carbazole backbone (N-12 to N-15), or an azacarbazole backbone (N-16 to N-34), which exhibits high electron transport property, are more preferable.

Among them, the monovalent nitrogen atom-containing group represented by $A^1$ or $A^3$ preferably contains a basic group, which exhibits high ligating property to a metal element of Group 11. Specific examples thereof may include (a) a group containing a pyridine ring or a pyrimidine ring; (b) an amino group; and (c) a dithiocarbamate group or a thioamide group.

(a) Group Containing Pyridine Ring or Pyrimidine Ring

A pyridine ring or a pyrimidine ring is a heteroaromatic ring of π electron deficient system in which the unpaired electrons are not incorporated into the π-conjugated system, and thus a group containing these exhibits high ligating property to a metal element of Group 11. Specific examples thereof may include those derived from a pyridine ring, a pyrimidine ring, or a condensed ring containing these. In this case, $A^1$ or $A^3$ may be a monovalent group obtained by removing one hydrogen atom from a pyridine ring, a pyrimidine ring, or a condensed ring containing these. Examples thereof may include the groups represented by the following N-1 to N-11.

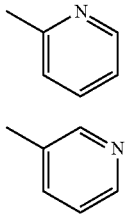

N-3
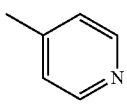

N-4
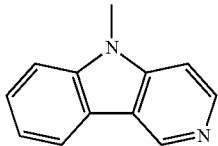

N-5
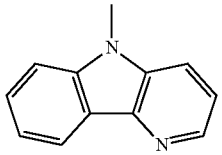

N-6
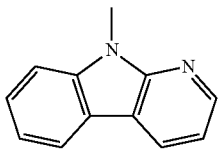

N-7
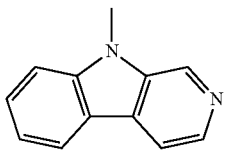

N-8
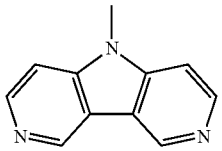

N-9
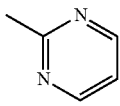

N-10
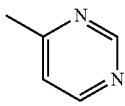

N-11
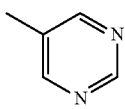

Alternatively, $A^1$ or $A^3$ may be a monovalent group obtained by bonding two or more of a pyridine ring, a pyrimidine ring, and a condensed ring containing these to each other directly or via the divalent linking group described above, or a monovalent group obtained by bonding one or more of a pyridine ring, a pyrimidine ring, and a condensed ring containing these to one or more of nitrogen-containing aromatic rings other than these directly or via the divalent linking group described above. $A^1$ or $A^3$ preferably contains a group (a pyridine ring-containing group) derived from a ring (a pyridine ring-containing ring) containing a pyridine ring. In other words, the groups represented by N-1 to N-8 above are preferable.

In a preferred embodiment, $A^1$ or $A^3$ is a structure having the monovalent pyridine ring-containing group above at the terminal portion of the nitrogen-containing aromatic ring having a condensed ring structure such as a carbazole backbone or an azacarbazole backbone, which exhibits high electron transport property. Such a condensed ring structure exhibits high carrier transport property and thus the carrier can be sufficiently transported even in a case in which the ground layer is in contact with the power generation layer or the electron transport layer of the organic photoelectric conversion element, as a result, a decrease in power generation efficiency can be suppressed. A divalent or trivalent linking group derived from the nitrogen-containing aromatic ring having a condensed ring structure such as a carbazole backbone or an azacarbazole backbone, which exhibits high electron transport property, are presented below. In the present embodiment, one bonding site of the following divalent groups (N-12 to N-36) or two bonding sites of the following trivalent groups (N-37 and N-38) are bonded to the monovalent group represented by N-1 to N-7 above directly or via the divalent linking group described above.

N-12
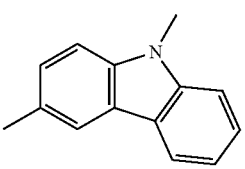

N-13
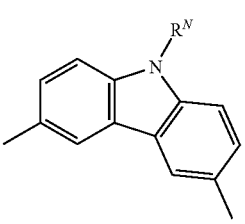

N-14
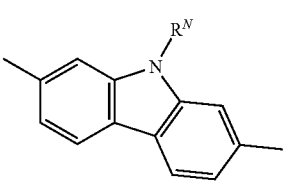

N-15
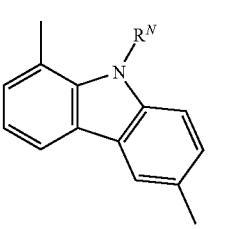

N-16
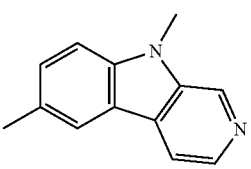

-continued
N-17 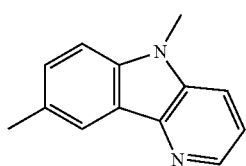
N-18 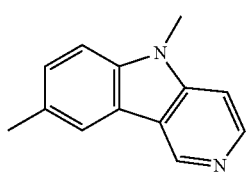
N-19 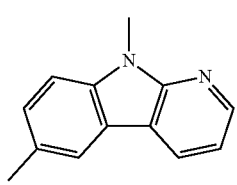
N-20 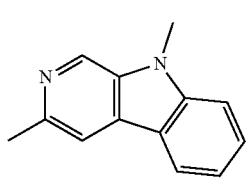
N-21 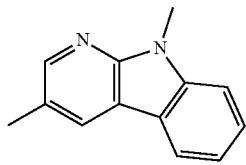
N-22 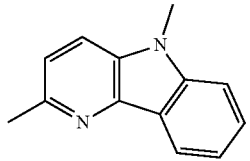
N-23 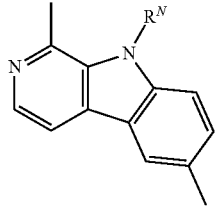
N-24 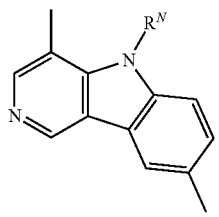
-continued
N-25 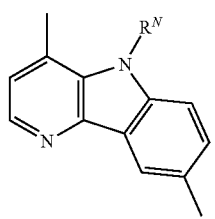
N-26 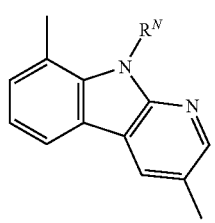
N-27 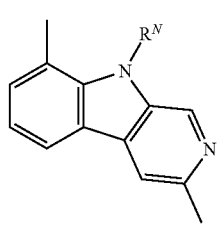
N-28 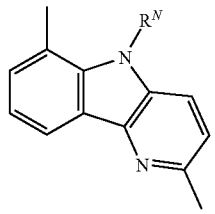
N-29 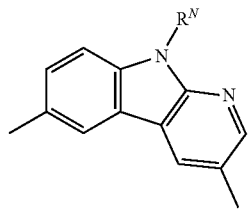
N-30 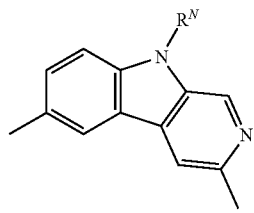
N-31 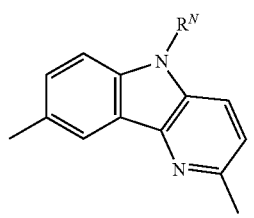

-continued

N-32
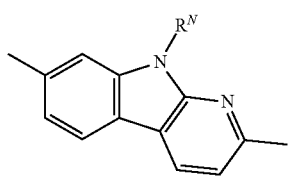

N-33
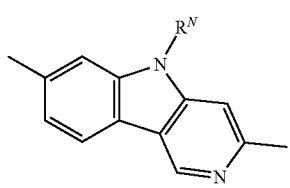

N-34
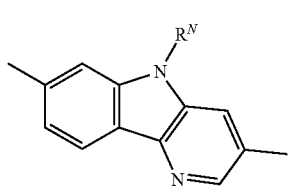

N-35
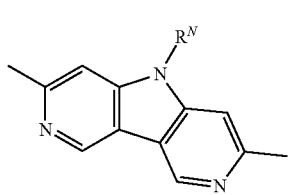

N-36
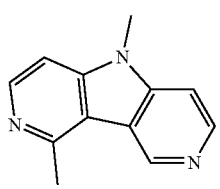

N-37
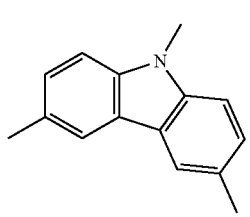

N-38
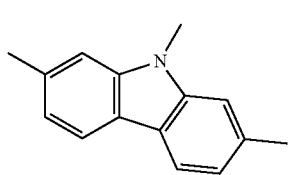

In Formulas above, $R^N$ is not particularly limited, and examples thereof may include a hydrogen atom or the groups exemplified as the substituents in the nitrogen-containing aromatic ring.

Among them, a group having a pyridyl group (N-1 to N-3) at the peripheral portion of the compound (terminal portion of the compound, that is, the terminal portion of $A^1$ or the terminal portion of $A^3$) is preferable in terms of improving the ligating property to a metal element of Group 11. The pyridyl group has three isomers of a 2-pyridyl group (N-1), a 3-pyridyl group (N-2), and a 4-pyridyl group (N-3) depending on the position of the nitrogen atom, any isomer thereof can be preferably used, and the 2-pyridyl group (N-1) exhibits particularly high orientation to an element of Group 11 of the periodic table. Consequently, a group having the 2-pyridyl group (N-2) at the terminal portion of the compound (the terminal portion of $A^1$ or the terminal portion of $A^3$) is more preferable. In this case, a favorable transparent conductive film tends to be provided. A group having a pyridyl group at the terminal portion of the nitrogen-containing aromatic ring having a condensed ring structure such as a carbazole backbone or an azacarbazole backbone, which exhibits high electron transport property, is particularly preferable.

Particularly in the case of the compound represented by Formula (1), $A^1$ preferably has the structures represented by the following formulas N-39 to N-45.

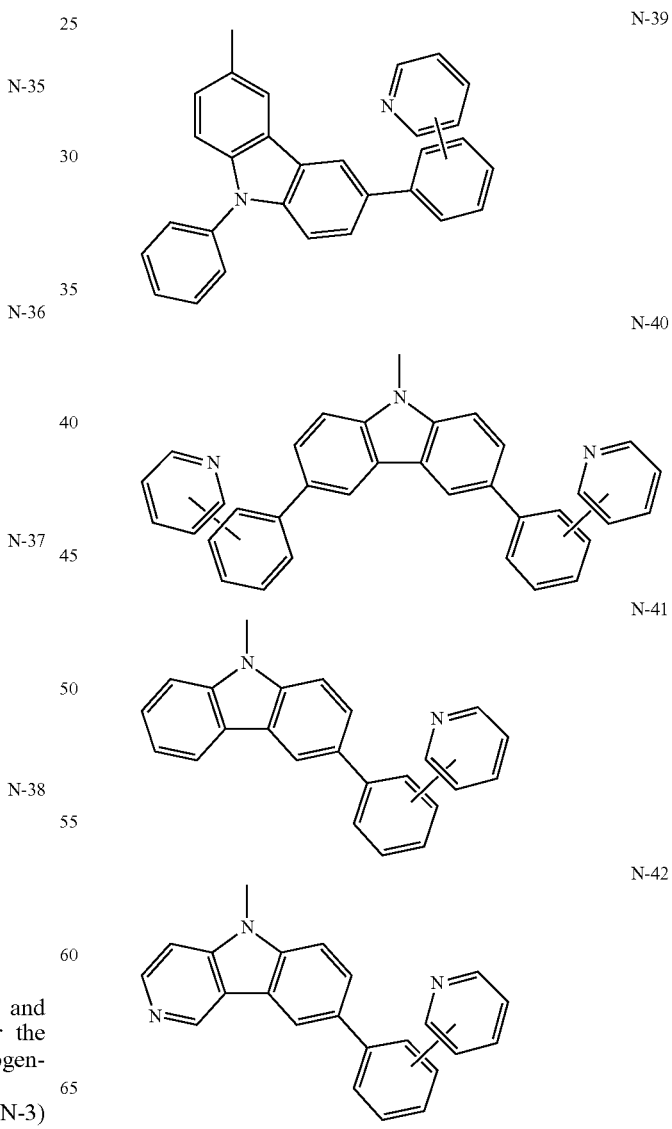

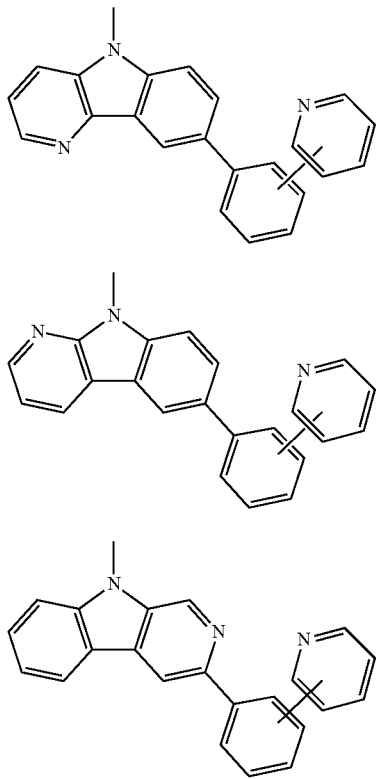

N-43

N-44

N-45

In addition, in another preferred embodiment, a form is also a preferred embodiment in which $A^1$ or $A^3$ is a group obtained by substituting one or more of the hydrogen atoms of the pyridine ring-containing ring group with an amino group or a dithiocarbamate group which will be described below or an alkyl group which is substituted with an amino group or a dithiocarbamate group and has from 1 to 4 carbon atoms (a methyl group, an ethyl group, a propyl group, an isopropyl group, a n-butyl group, a sec-butyl group, or a tert-butyl group) (for example, exemplified compounds of No. 55 and No. 56 to be described below).

(b) Amino Group

The amino group is preferably an amino group that does not have an electron-withdrawing group at an adjacent site. Such an amino group exhibits high ligating property to a metal element of Group 11. The amino group may be any one of a primary amino group, a secondary amino group, a tertiary amino group, and a quaternary amino group (an ammonium group). However, a primary amino group, a secondary amino group, and a tertiary amino group are preferable since these are neutral and thus exhibit favorable ligating property to a metal atom. Moreover, a tertiary amino group is preferable from the viewpoint of the solubility and coating property. In addition to this, a tertiary amino group does not have a NH group exhibiting high polarity and thus a polar solvent such as water hardly remains in the film, as a result, the durability of the transparent conductive film or the organic photoelectric conversion element to be obtained tends to be improved. Meanwhile, the fact that the amino group is a quaternary amino group (ammonium group) means that the amino group is in the form of a salt, for example, as presented in the following compound 50. In other words, the nitrogen-containing organic compound according to the present invention includes a case in which the amino group as a nitrogen atom-containing group is in the form of a salt. Here, examples of an anion which forms a salt with a quaternary amino group (ammonium group) is not particularly limited and may include a halogen atom (a fluorine atom, a chlorine atom, or a bromine atom), a sulfate ion, a nitrate ion, a tetrafluoroborate ion, and a hexafluorophosphate ion. Among these, a halogen atom is preferable, and among them a bromine atom is preferable.

$R^A$ to $R^C$ in the secondary amino group (—NHR$^A$), the tertiary amino group (—NR$^A$R$^B$), and the quaternary amino group (—N$^+$R$^A$R$^B$R$^C$) represent a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted heteroaryl group having from 1 to 30 carbon atoms. Here, $R^A$ and $R^B$ in the tertiary amino group and $R^A$, $R^B$, and $R^C$ in the quaternary amino group may be the same as or different from each other. In addition, each of each $R^A$ to $R^C$ may be the same as or different from each other in a case in which the nitrogen-containing organic compound has a plurality of amino groups.

Here, the alkyl group having from 1 to 20 carbon atoms, the cycloalkyl group having from 3 to 20 carbon atoms, the aryl group having from 6 to 30 carbon atoms, and the heteroaryl group having from 1 to 30 carbon atoms are the same as those in Formula (4) described above.

Among these, $R^A$, $R^B$, and $R^C$ are preferably sterically as small as possible from the viewpoint of the ligating property to a metal atom. Specifically, $R^A$, $R^B$, and $R^C$ are preferably a substituted or unsubstituted alkyl group having from 1 to 12 carbon atoms, a substituted or unsubstituted cycloalkyl group having from 3 to 12 carbon atoms, a substituted or unsubstituted aryl group having from 6 to 12 carbon atoms, or a substituted or unsubstituted heteroaryl group having from 4 to 12 carbon atoms, and more preferably a substituted or unsubstituted alkyl group having from 1 to 8 carbon atoms or a substituted or unsubstituted heteroaryl group having from 4 to 6 carbon atoms. $R^A$, $R^B$, and $R^C$ are even more preferably a substituted or unsubstituted alkyl group having from 1 to 4 carbon atoms (particularly preferably a methyl group, an ethyl group, a propyl group, or a tert-butyl group) or a group derived from a substituted or unsubstituted nitrogen-containing aromatic ring having from 4 to 6 carbon atoms (particularly preferably a pyridyl group).

In addition, a form is also preferable in which at least one of $R^A$, $R^B$, and $R^C$ is an alkyl group, a cycloalkyl group, an aryl group, or a heteroaryl group which is substituted with an amino group. This is because the coordinative interaction to a metal atom can be enhanced in a case in which an amino group is present at a high density. Moreover, in such a case, it is also preferable in that favorable solubility and coating property can be obtained and the durability of the organic photoelectric conversion element to be obtained can be improved. It is effective to perform coating of the compound under nitrogen without moisture and oxygen in order to obtain high durability, but there is a problem that a fish eye is likely to be formed when performing coating under nitrogen. It is possible to suppress the formation of fish eye even when performing coating under nitrogen by increasing the number (density) of amino group. Moreover, the nitrogen-containing organic compound containing these amino groups dissolves in an organic solvent exhibiting high polarity such as an alcohol or a fluorinated alcohol, and thus the ground layer can be easily formed by coating the nitrogen-containing organic compound above directly on the photoelectric conversion layer which does not dissolve in a highly polar solvent.

For example, at least one of $R^A$, $R^B$, and $R^C$ is preferably a group represented by the following Formula. The amino group can be uniformly and densely present on the surface of the ground layer in the case of using a nitrogen-containing organic compound having such an amino group branched in two or more generations, and thus it is possible to enhance the coordinative interaction thereof to a metal atom.

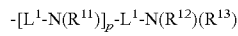

In Formula above, $L^1$ represents a divalent linking group selected from a substituted or unsubstituted alkylene group having from 1 to 20 carbon atoms, a substituted or unsubstituted cycloalkylene group having from 3 to 20 carbon atoms, a substituted or unsubstituted arylene group having from 6 to 30 carbon atoms, a substituted or unsubstituted heteroarylene group having from 1 to 30 carbon atoms, and a substituted or unsubstituted alkyleneoxy group having from 1 to 20 carbon atoms. The alkylene group, the cycloalkylene group, the arylene group, the heteroarylene group, and the alkyleneoxy group have the same definition as those in the divalent linking group described above. Among them, $L^1$ is preferably a substituted or unsubstituted alkylene group having from 1 to 8 carbon atoms and more preferably a methylene group, an ethylene group, a trimethylene group, or a tetramethylene group. The plurality of $L^1$s may be the same as or different from each other in a case in which p is 1 or more.

In addition, in Formula above, $R^{11}$ to $R^{13}$ represent a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted heteroaryl group having from 1 to 30 carbon atoms, or a group represented by Formula: $-[L^1-N(R^{11})]_p-L^1-N(R^{12})(R^{13})$. $R^{11}$ to $R^{13}$ may be the same as or different from each other. The alkyl group, the cycloalkyl group, the aryl group, and the heteroaryl group have the same definition as those in Formula (4) described above, and thus the description thereof will not be presented.

Among them, $R^{11}$ to $R^{13}$ is preferably an alkyl group having from 1 to 8 carbon atoms or a group represented by Formula: $-[L^1-N(R^{11})]_p-L^1-N(R^{12})(R^{13})$ and more preferably an alkyl group having from 1 to 3 carbon atoms (a methyl group, an ethyl group, a propyl group, or an isopropyl group) or a group represented by Formula: $-[L^1-N(R^{11})]_p-L^1-N(R^{12})(R^{13})$. Particularly preferably, $R^{12}$ or $R^{13}$ at the terminal is a hydrogen atom or a methyl group from the viewpoint of further improving the coordinative interaction to a metal atom.

p represents the repeating number of Formula: $-L^1-N(R^{11})-$ and may be appropriately selected depending on the desired number of the amino group. For example, p is preferably an integer of 0 to 5, more preferably an integer of 0 to 3, and particularly preferably 0 or 1.

In other words, the amino group as $A^1$ or $A^3$ preferably has the following structure (including a salt form).

[Chem. 8]

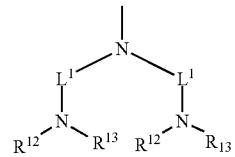

In addition, in another preferred embodiment, a form is also preferable in which at least one of $R^A$, $R^B$, and $R^C$ above of the amino group as $A^1$ or $A^3$ is an alkyl group, a cycloalkyl group, an aryl group, or a heteroaryl group which is substituted with a dithiocarbamate group to be described below. This is because the coordinative interaction to a metal atom can be enhanced in a case in which the amino group and the dithiocarbamate group are present at a high density. More preferably, at least one of $R^A$, $R^B$, and $R^C$ above is an alkyl group which has from 1 to 8 carbon atoms and is substituted with a dithiocarbamate group to be described below (for example, Exemplified Compound No. 62 to be described below).

(c) Dithiocarbamate Group or Thioamide Group

A dithiocarbamate group or a thioamide group is a monovalent group derived from dithiocarbamate or thioamide and has a sulfur atom exhibiting specifically high ligating property with respect to an element of Group 11 of the periodic table. Each of the dithiocarbamate group and the thioamide group has two isomers depending on the substitution site. In the case of dithiocarbamate group, one isomer takes a form of $-N(R^D)-C(=S)-S-R^E$, in which a nitrogen atom is linked with another group, and the other isomer takes a form of $-S-C(=S)-NR^FR^G$, in which a sulfur atom is linked with another group. In addition, in the case of thioamide group, one isomer takes a form of $-N(R^H)-C(=S)-R^I$, in which a nitrogen atom is linked with another group, and the other isomer takes a form of $-C(=S)-NR^JR^K$, in which a carbon atom is linked with another group. It is possible to preferably use either form in the present invention. Preferably, it is a dithiocarbamate group having a plurality of sulfur atoms, and more preferably, it is a dithiocarbamate group having a form in which a sulfur atom is linked with another group. In the case of taking such a form, a polar solvent such as water hardly remains in the film, and thus favorable durability tends to be obtained.

$R^D$ and $R^F$ to $R^K$ in the dithiocarbamate group or the thioamide group represent a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted heteroaryl group having from 1 to 30 carbon atoms.

In addition, $R^E$ represents a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted heteroaryl group having from 1 to 30 carbon atoms, or an alkali metal atom (Li, Na, K, or the like). Here, $R^D$ and $R^E$, and $R^F$ and $R^G$ in the dithiocarbamate group and $R^H$ and $R^I$, and $R^J$ and $R^K$ in the thioamide group may be the same as or different from each other. In addition, the plurality of $R^D$s to $R^K$s may be the same as or different from each other in a case in which the nitrogen-containing organic compound has a plurality of dithiocarbamate group or thioamide group. The alkyl group, the cycloalkyl group, the aryl group, and the heteroaryl group have the same definition as those in Formula (4) described above.

Among these, $R^D$ to $R^K$ are preferably sterically as small as possible from the viewpoint of the ligating property to a metal atom. Specifically, $R^D$ and $R^F$ to $R^K$ are preferably a hydrogen atom, a substituted or unsubstituted alkyl group having from 1 to 12 carbon atoms, a substituted or unsubstituted cycloalkyl group having from 3 to 12 carbon atoms, a substituted or unsubstituted aryl group having from 6 to 12 carbon atoms, or a substituted or unsubstituted heteroaryl group having from 4 to 12 carbon atoms, and more preferably a hydrogen atom, a substituted or unsubstituted alkyl group having from 1 to 8 carbon atoms or a substituted or unsubstituted heteroaryl group having from 4 to 6 carbon atoms. $R^D$ and $R^F$ to $R^K$ are even more preferably a hydrogen atom, a substituted or unsubstituted alkyl group having from 1 to 4 carbon atoms (particularly preferably a methyl group, an ethyl group, a propyl group, or a tert-butyl group) or a group derived from a substituted or unsubstituted nitrogen-containing aromatic ring having from 4 to 6 carbon atoms (particularly preferably a pyridyl group). $R^E$ is preferably a hydrogen atom, a substituted or unsubstituted alkyl group having from 1 to 12 carbon atoms, a substituted or unsubstituted heteroaryl group having from 4 to 12 carbon atoms, or an alkali metal atom and more preferably a hydrogen atom, a substituted or unsubstituted alkyl group having from 1 to 8 carbon atoms, a substituted or unsubstituted heteroaryl group having from 4 to 6 carbon atoms, or an alkali metal atom. $R^E$ is even more preferably a hydrogen atom, a substituted or unsubstituted alkyl group having from 1 to 4 carbon atoms (particularly preferably a methyl group, an ethyl group, a tert-butyl group) or a group derived from a substituted or unsubstituted nitrogen-containing aromatic ring having from 4 to 6 carbon atoms (particularly preferably a pyridyl group), or an alkali metal atom (particularly a sodium atom (Na)).

In addition, a form is also preferable in which at least one of $R^D$ to $R^G$ of the dithiocarbamate group (—N($R^D$)—C(=S)—S—$R^E$ or —S—C(=S)—NR$^F$R$^G$) is an alkyl group, a cycloalkyl group, an aryl group or a heteroaryl group which is substituted with a dithiocarbamate group. This is because it is possible to enhance the coordination interaction force to a metal atom per unit area in a case in which the dithiocarbamate group coordinating an element of Group 11 of the periodic table is present at a high density. Moreover, it is preferable to have a form such as a hyperbranched polymer in which a large number of substitutions have been performed in the main chain of a polymer or the like (a form branched in two or more generations). From this point of view, at least one of $R^D$, $R^F$, and $R^G$ bonding to the nitrogen atom is an alkyl group, a cycloalkyl group, an aryl group, or a heteroaryl group which is substituted with a dithiocarbamate group.

For example, at least one of $R^D$, $R^F$, and $R^G$ is preferably a group represented by the following Formula. The thiocarbamate group can be uniformly and densely present on the surface of the ground layer in the case of using a nitrogen-containing organic compound having such a thiocarbamate group branched in two or more generations, and thus it is possible to enhance the coordinative interaction thereof to a metal atom.

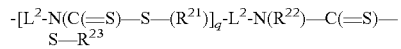

or

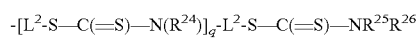

In Formulas above, $L^2$ represents a divalent linking group selected from a substituted or unsubstituted alkylene group having from 1 to 20 carbon atoms, a substituted or unsubstituted cycloalkylene group having from 3 to 20 carbon atoms, a substituted or unsubstituted arylene group having from 6 to 30 carbon atoms, a substituted or unsubstituted heteroarylene group having from 1 to 30 carbon atoms, and a substituted or unsubstituted alkyleneoxy group having from 1 to 20 carbon atoms. The alkylene group, the cycloalkylene group, the arylene group, the heteroarylene group, and the alkyleneoxy group have the same definition as those in the divalent linking group described above, and thus the description thereof will not be presented. $L^2$ is preferably a substituted or unsubstituted alkylene group having from 1 to 8 carbon atoms and more preferably a methylene group, an ethylene group, a trimethylene group, or a tetramethylene group.

In addition, in Formulas above, $R^{21}$ and $R^{23}$ each independently represent a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, an alkali metal atom, or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$. In addition, $R^{22}$, $R^{24}$ to $R^{26}$ each independently represent a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$. $R^{21}$ to $R^{26}$ may be the same as or different from each other. The alkyl group, the cycloalkyl group, the aryl group, and the heteroaryl group have the same definition as those in Formula (4) described above. In addition, the alkali metal atom has the same definition as that in $R^E$ described above.

Among them, $R^{21}$ and $R^{23}$ are each independently preferably a hydrogen atom, an alkali metal atom, an alkyl group having from 1 to 8 carbon atoms, or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$ and more preferably an alkali metal atom (Na or K), an alkyl group having from 1 to 3 carbon atoms (a methyl group, an ethyl group, a propyl group, or an isopropyl group), or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$.

In addition, $R^{22}$, $R^{24}$ to $R^{26}$ are each independently preferably a hydrogen atom, an alkyl group having from 1 to carbon atoms, or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$ and more preferably a hydrogen atom, an alkyl group having from 1 to 3 carbon atoms (a methyl group, an ethyl group, a propyl group, or an isopropyl group), or a group represented by Formula: -[$L^2$-N(C(=S)—S—($R^{21}$)]$_q$-$L^2$-N($R^{22}$)—C(=S)—S—$R^{23}$ or -[$L^2$-S—C(=S)—N($R^{24}$)]$_q$-$L^2$-S—C(=S)—NR$^{25}$R$^{26}$. Particularly preferably, $R^{25}$ or $R^{26}$ at the terminal is a hydrogen atom or a methyl group from the viewpoint of further improving the coordinative interaction to a metal atom.

q represents the repeating number of Formula: [$L^2$-N(C(=S)—S—($R^{21}$)] or [$L^2$-S—C(=S)—N($R^{24}$)], and may be appropriately selected depending on the desired number of the dithiocarbamate group. For example, q is preferably an integer of 0 to 5, more preferably an integer of 0 to 3, and particularly preferably 0 or 1.

In other words, in a preferred embodiment, the dithiocarbamate group as $A^1$ or $A^3$ preferably has the following structures S-1 to S-4.

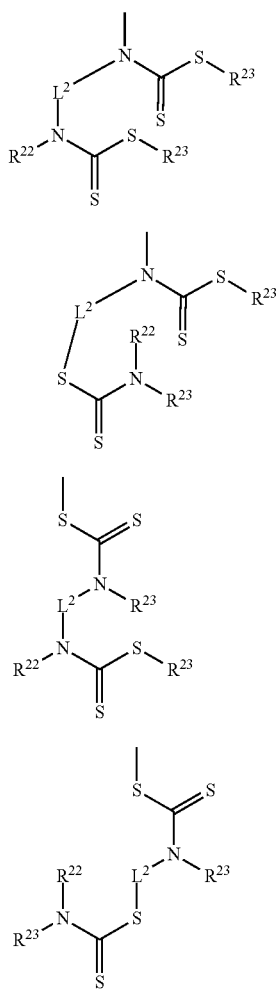

Among them, a group represented by S-3 or S-4, which is a dithiocarbamate group in a form in which the sulfur atom is linked with another group, is preferable from the viewpoint that a polar solvent such as water hardly remains in the film and the durability is improved.

On the other hand, a group represented by S-1 or S-2, which has a symmetrical structure, is preferable from the viewpoint of synthesis.

Among these, $A^1$ is preferably (a) a group containing a pyridine ring or a pyrimidine ring in terms of the coordinate bonding strength with an element of Group 11. On the other hand, from the viewpoint of enhancing the density of a substituent capable of coordinating an element of Group 11, $A^3$ is preferably (b) an amino group, (c) a dithiocarbamate group or a thioamide group, or a pyridine ring-containing ring group substituted with an alkyl group which has from 1 to 4 carbon atoms and is substituted with an amino group, a dithiocarbamate group, or a thioamide group to be described below. In other words, the lone pair of electrons of the nitrogen-containing heteroaromatic ring which is not delocalized tends to exhibit strong coordinate bonding strength but there is a limit to densely integrate the ring in the molecule due to its cyclic structure. On the other hand, an amino group or a dithiocarbamate group is a relatively small substituent, and thus it is estimated that there is a tendency that the substituent capable of coordinating an atom of Group 11 can be disposed on the outermost layer of the molecule at a high density in the manner of dendrimer/hyperbranched polymer. As a result, any of the structures can exhibit the effect of single layer growth type (Frank-van der Merwe: FW type) film growth by the same coordination to an element of Group 11.

In Formula (2) or (3) above, a divalent nitrogen atom-containing group represented by $A^2$, $A^4$ or $A^5$ is not particularly limited as long as it is an organic group containing a nitrogen atom. Examples thereof may include an imino group (—NR—), an amide group (—CO—NR—), an imide group (—CO—NR—CO—), a sulfonamide group (—$SO_2$—NR—), an oxime group (>C=N—OH), and a group containing a substituted or unsubstituted nitrogen-containing aromatic ring. Here, as the nitrogen-containing aromatic ring and a substituent thereof, the nitrogen-containing aromatic ring and a substituent thereof exemplified in $A^1$ or $A^3$ above can be used. In addition, one or more of the hydrogen atoms in the nitrogen-containing aromatic ring may be substituted with an amino group, a dithiocarbamate group, a thioamide group, a cyano group, an isonitrile group, an isocyanate group, or a thioisocyanate group, or the nitrogen-containing aromatic ring may be bonded with an amino group, a dithiocarbamate group, a thioamide group, a cyano group, an isonitrile group, an isocyanate group, or a thioisocyanate group via a divalent linking group. As the group containing a nitrogen-containing aromatic ring, a plurality of these nitrogen-containing aromatic rings may be used in combination. At this time, the plurality of heteroaromatic rings may be bonded directly or via the divalent linking group described above, or a plurality of nitrogen-containing aromatic rings may form a condensed ring.

In a preferred embodiment, a divalent nitrogen atom-containing group represented by $A^2$ or $A^4$ or $A^5$ contains a basic group, which exhibits high ligating property to a metal element of Group 11. Specifically, the group preferably contains (a) a group containing a pyridine ring or a pyrimidine ring, (b) an amino group, and (c) a dithiocarbamate group or a thioamide group in the same manner as $A^1$ and $A^3$ above. The specific form of the (a) group containing a pyridine ring or a pyrimidine ring is the same as that of the (a) group containing a pyridine ring or a pyrimidine ring in $A^1$ or $A^3$ except that one hydrogen atom is further removed from the group exemplified as the monovalent group thereof to form a divalent group, and thus the description thereof will not be presented. More preferably, $A^2$ or $A^4$ or $A^5$ contains a group derived from a pyridine ring-containing ring (pyridine ring-containing group) and even more preferably contains a group derived from a pyridine ring. Examples of the group derived from a pyridine ring may include the following divalent groups derived from a pyridine ring (pyridinylene group) in addition to the divalent groups represented by N-16 to N-36 above.

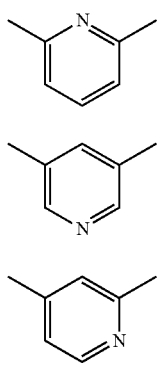

N-46

N-47

N-48

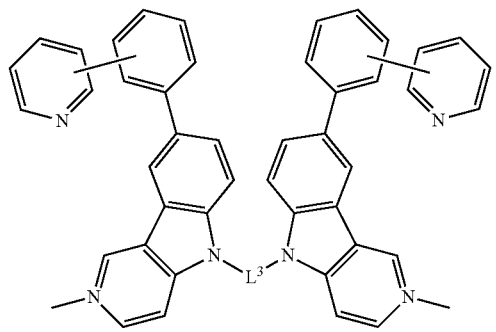

N-50

In another preferred embodiment, a divalent nitrogen atom-containing group represented by $A^2$ or $A^4$ or $A^5$ contains a divalent group derived from the nitrogen-containing aromatic ring having a condensed ring structure such as a carbazole backbone or an azacarbazole backbone which exhibits electron transport property. Specifically, the group preferably contains a divalent group represented by N-12 to N-36 above. In the case of having such a condensed ring structure, high carrier transport property is exhibited and thus the carrier can be sufficiently transported even in a case in which the ground layer is in contact with the power generation layer, the electron transport layer, or the like of the organic photoelectric conversion element, as a result, a decrease in power generation efficiency can be suppressed. Among them, preferably, the group preferably contains a divalent group represented by N-16 to N-36 above having an azacarbazole backbone in terms of improving the ligating property to a metal element of Group 11.

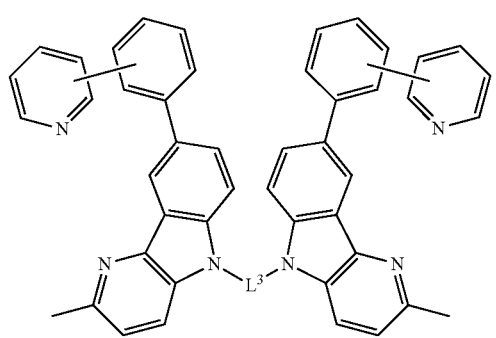

N-51

In still another preferred embodiment, it is preferable that a nitrogen-containing aromatic ring having a condensed ring structure such as a carbazole backbone or an azacarbazole backbone, which exhibits high electron transport property, is contained in the main chain structure of $A^2$ or $A^4$ or $A^5$ and a monovalent group derived from a pyridine ring, that is, a pyridyl group (N-1 to N-3) is contained in the side chain portion of $A^2$ or $A^4$ or $A^5$. The ligating property to a metal element of Group 11 and the carrier transport property are improved and thus a decrease in power generation efficiency can be prevented in the case of having such a condensed ring structure. For example, it is preferable to contain a structure represented by the following Formulas N-49 to N-56.

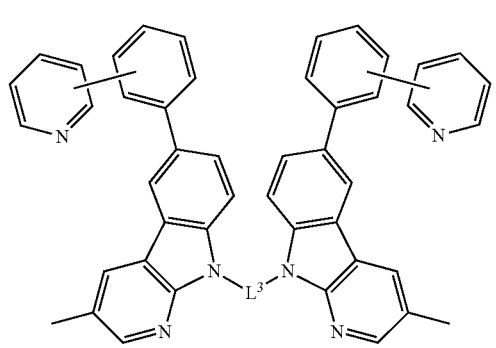

N-52

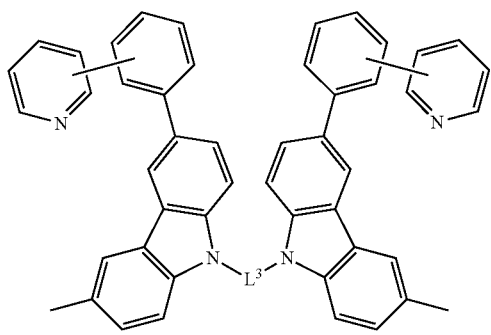

N-49

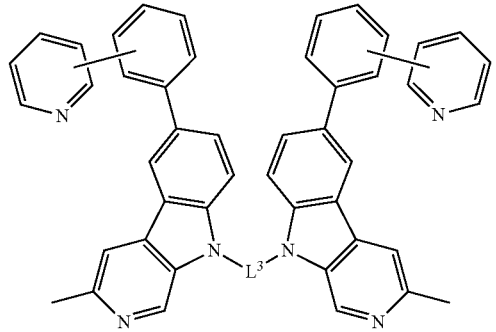

N-53

-continued

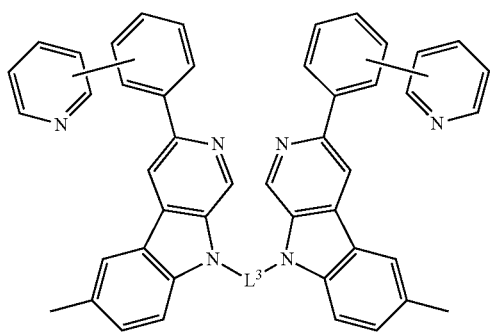

N-54

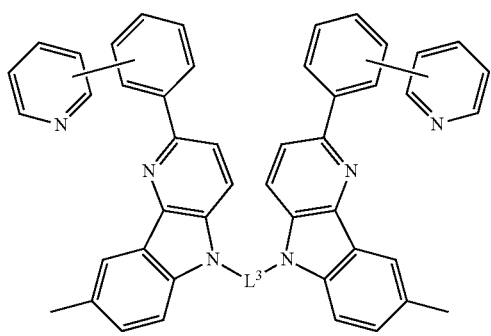

N-55

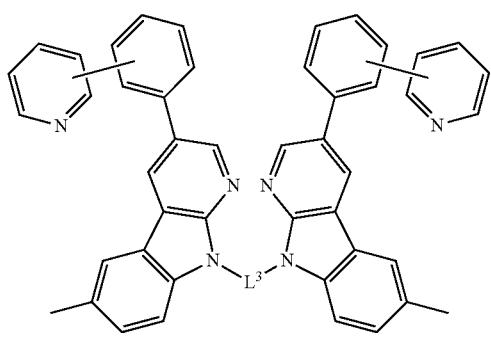

N-56

In Formulas above, $L^3$ represents a divalent linking group selected from a substituted or unsubstituted alkylene group having from 1 to 20 carbon atoms, a substituted or unsubstituted cycloalkylene group having from 3 to 20 carbon atoms, a substituted or unsubstituted arylene group having from 6 to 30 carbon atoms, a substituted or unsubstituted heteroarylene group having from 1 to 30 carbon atoms, and a substituted or unsubstituted alkyleneoxy group having from 1 to 20 carbon atoms. The alkylene group, the cycloalkylene group, the arylene group, and the alkyleneoxy group have the same definition as those in the divalent linking group described above. Examples of the heteroarylene group may include a group derived from a heteroaromatic ring containing a nitrogen atom (a nitrogen-containing aromatic ring) such as pyridine, pyrimidine, pyrazine, triazine, carbazole, carboline, diazacarbazole, pyrrole, quinoline, isoquinoline, quinolone, isoquinolone, piperidine, coumarin, benzimidazole, benzimidazolone, benzoxazole, benzoisoxazole, benzoxazolone, benzothiazole, benzothiazolethione, benzothiazolone, benzoisothiazolone, indole, carbazole, pyrazole, imidazole, oxazole, isoxazole, thiazole, isothiazole, indazole, pyridazine, cinnoline, quinazoline, quinazolone, quinoxaline, quinoxalone, phthalazine, acridine, acridone, benzoxazinedione, benzoxazinone, naphthalidine, naphtholactam, quinazolinedione, quinoxalinedione, phthalazinedione, pyridone, phthalazone, phthalamidine, naphthalimidine, or dioxopyrimidine in addition to a group derived from a heterocycle not containing a nitrogen atom as the heteroaryl group in the divalent linking group described above. A substituted or unsubstituted arylene group having from 6 to carbon atoms or a substituted or unsubstituted heteroarylene group having from 1 to 12 carbon atoms is preferable and a phenylene group or a pyridinylene group is more preferable.

In addition, as a form containing (b) an amino group and (c) a dithiocarbamate group or a thioamide group, a group obtained by substituting one or more of the hydrogen atoms of a divalent group derived from a nitrogen-containing aromatic ring with the amino group, the dithiocarbamate group, or the thioamide group described above, or an alkyl group which has from 1 to 4 carbon atoms (a methyl group, an ethyl group, a propyl group, an isopropyl group, a n-butyl group, a sec-butyl group, or a tert-butyl group) and is substituted with an amino group, a dithiocarbamate group, or a thioamide group. Preferably, $A^2$ or $A^4$ or $A^5$ has a structure in which a nitrogen-containing aromatic ring having a condensed ring structure such as a carbazole backbone or an azacarbazole backbone, which exhibits high electron transport property, is contained in the main chain structure thereof (for example, N-12 to N-35 above) and the nitrogen-containing aromatic ring is a group obtained by substituting one or more of the hydrogen atoms thereof with an amino group or a dithiocarbamate group to be described below, or an alkyl group which has from 1 to 4 carbon atoms (a methyl group, an ethyl group, a propyl group, a n-butyl group, or a t-butyl group) and is substituted with the amino group or the dithiocarbamate group described above. For example, the following structures are preferred (for example, Exemplified Compounds of No. 59 and No. 60 below).

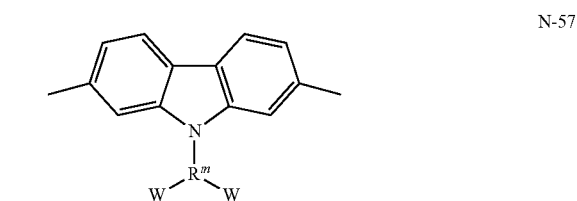

N-57

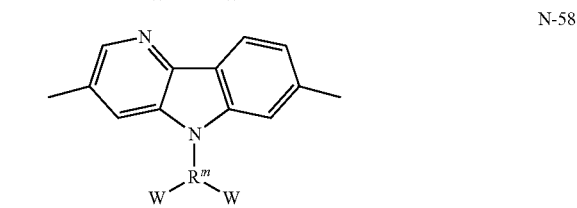

N-58

In Formulas above, $R^m$ represents a trivalent group derived from an alkyl chain having from 1 to 12 carbon atoms. Specific examples thereof may include an ethanetriyl group, a propanetriyl group, a butanetriyl group, a pentanetriyl group, a hexanetriyl group, a heptanetriyl group, an octanetriyl group, a nonanetriyl group, a decanetriyl group, an undecanetriyl group, and a dodecanetriyl group.

In Formulas above, W represents an amino group, a dithiocarbamate group, or an alkyl group which has from 1 to 4 carbon atoms (a methyl group, an ethyl group, a propyl group, an isopropyl group, a n-butyl group, a sec-butyl group, or a tert-butyl group) and is substituted with an amino group or a dithiocarbamate group. The specific forms of these are the same as the forms of the amino group and the dithiocarbamate group of $A^1$.

Alternatively, $A^2$ or $A^4$ or $A^5$ has a polyalkylene imine structure in another preferred embodiment in which the divalent nitrogen atom-containing group represented by $A^2$ or $A^4$ or $A^5$ contains (b) an amino group.

In the present invention, the polyalkylene imine refers to a linear or branched polymer having an aminoalkylene group as a repeating unit. Meanwhile, in the present specification, an oligomer such as a dimer or a trimer is also included in the polyalkylene imine. As an example of the polyalkylene imine used in the present embodiment, a polyethylene imine structure which is a branched polymer having an aminoethylene group as a repeating unit is presented below.

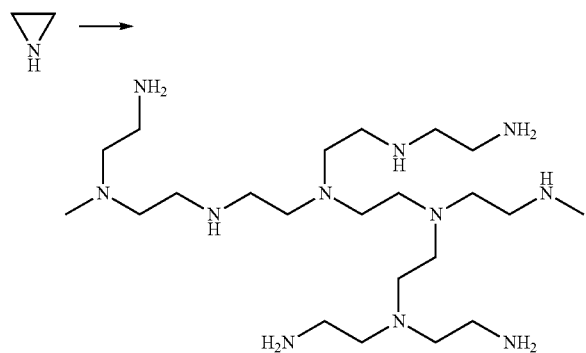

The polyethylene imine presented above contains a primary amino group ($NH_2$—$CH_2CH_2$—), a secondary amino group ($NH$—($CH_2CH_2$—)$_2$), and a tertiary amino group ($N$—($CH_2CH_2$—)$_3$). Among these, the primary amino group constitutes the terminal of the chain and the tertiary amino group constitutes the branch point of the chain.

The polyalkylene imine of the present embodiment is not particularly limited as long as it is a polymer having an aminoalkylene group as a repeating unit as described above. Examples of the alkylene group contained in the aminoalkylene group may include a methylene group (—$CH_2$—), an ethylene group (—$CH_2CH_2$—), a trimethylene group (—$CH_2CH_2CH_2$—), a propylene group (—$CH(CH_3)CH_2$—), a tetramethylene group (—$CH_2CH_2CH_2CH_2$—), and a 1,2-dimethylethylene group (—$CH(CH_3)CH(CH_3)$—). Among these, an ethylene group, a trimethylene group, or a propylene group is preferable and an ethylene group, a trimethylene group, or a propylene group is even more preferable from the viewpoint of ease of synthesis and availability, or from the viewpoint of compatibility with the coating solution. Meanwhile, the structure of the terminal is not particularly limited and is normally a primary amino group (—$NH_2$) or an alkyl group (for example, a methyl group, an ethyl group, a n-propyl group, an isopropyl group, a n-butyl group, or the like).

The polyalkylene imine of the present embodiment may be linear (that is, not containing a tertiary amino group) or branched, but a branched polyalkylene imine is preferable from the viewpoint of improving reactivity. In addition, the branch structure in the case of a branched polyalkylene imine is not also particularly limited and may be a mesh type structure or a dendrimer type structure. However, preferably, a dendrimer type structure is preferable in terms of improving the ligating property to a nitrogen atom. In the case of having such a structure, a large number of amino group is present at the terminal (side chain portion) of a dendrimer/hyperbranched polymer and an amino group can be uniformly and densely present on the outermost layer of the ground layer, and thus it is possible to further improve the coordinative interaction to a metal atom. The content proportion of each of the primary amino group, the secondary amino group, and the tertiary amino group in the case of a branched polyalkylene imine is not particularly limited.

Meanwhile, the terminal on the $A^2$ side of a polymer having a partial structure represented by Formula (2) above is usually an amino group in a case in which $A^2$ has a polyalkylene imine structure. However, the terminal may be a group (for example, a hydrogen atom or an alkyl group) other than an amino group as a matter of course.

In Formula (1) above, the n1-valent organic group as $Y^1$ is not particularly limited and examples thereof may include an n1-valent substituted or unsubstituted aromatic residue or an n1-valent substituted or unsubstituted aliphatic hydrocarbon residue. Here, the "aromatic residue" refers to a group obtained by removing n1 hydrogen atoms from an aromatic ring such as an aromatic hydrocarbon ring, a heterocyclic aromatic ring, and a condensed aromatic ring. In addition, the "aliphatic hydrocarbon residue" refers to a group obtained by removing n1 hydrogen atoms from an aliphatic hydrocarbon.

The n1-valent aromatic residue as $Y^1$ is not particularly limited. For example, a substituted or unsubstituted arylene group having from 6 to 30 carbon atoms and a substituted or unsubstituted heteroarylene group having from 1 to 30 carbon atoms may be mentioned in a case in which n1 is 2. Meanwhile, these groups may be bonded to each other via the divalent linking group described above. The arylene group having from 6 to 30 carbon atoms is the same as the case of the arylene group having from 6 to 30 carbon atoms in the divalent linking group. Examples of the heteroarylene group having from 1 to 30 carbon atoms may include a group derived from a heteroaromatic ring containing a nitrogen atom (a nitrogen-containing aromatic ring) such as pyridine, pyrimidine, pyrazine, triazine, carbazole, carboline, diazacarbazole (also referred to as monoazacarboline and indicating a ring constitution in which one of the carbon atoms constituting the carboline is substituted with a nitrogen atom), pyrrole, quinoline, isoquinoline, quinolone, isoquinolone, piperidine, coumarin, benzimidazole, benzimidazolone, benzoxazole, benzoisoxazole, benzoxazolone, benzothiazole, benzothiazolethione, benzothiazolone, benzoisothiazolone, indole, carbazole, pyrazole, imidazole, oxazole, isoxazole, thiazole, isothiazole, indazole, pyridazine, cinnoline, quinazoline, quinazolone, quinoxaline, quinoxalone, phthalazine, acridine, acridone, benzoxazinedione, benzoxazinone, naphthalidine, naphtholactam, quinazolinedione, quinoxalinedione, phthalazinedione, pyridone, phthalazone, phthalamidine, naphthalimidine, or dioxopyrimidine in addition to a group derived from a heterocycle not containing a nitrogen atom as the heteroarylene group in the divalent linking group described above. As the aromatic residue in a case in which n1 is 3 or more, a group obtained by further removing one or more hydrogen atoms from the arylene group or the heteroarylene group above.

The n1-valent aliphatic hydrocarbon residue as $Y^1$ is not particularly limited. For example, a substituted or unsubstituted alkylene group having from 1 to 20 carbon atoms and a substituted or unsubstituted cycloalkylene group having from 3 to 20 carbon atoms may be mentioned in a case in which n1 is 2.

The substituent in a case in which the aromatic residue or the aliphatic hydrocarbon residue has a substituent is not particularly limited and the substituents exemplified in $A^1$ or $A^3$ above may be preferably mentioned. A substituted or unsubstituted aryl group having from 6 to 12 carbon atoms, a substituted or unsubstituted heteroaryl group having from 1 to 12 carbon atoms, a substituted or unsubstituted arylene group having from 6 to 12 carbon atoms, or a substituted or unsubstituted heteroarylene group having from 1 to 12 carbon atoms is preferable.

Among them, $Y^1$ is preferably an n1-valent aromatic residue, and more preferably includes a group derived from benzene (a phenyl group, a phenylene group, or the like) and a heterocyclic group obtained by substituting a part thereof with nitrogen (a pyridyl group, a pyrazyl group, or the like) or a substituted or unsubstituted group which is derived from the structure represented by Formula (4) above in terms of obtaining adequate solubility. Particularly preferably, $Y^1$ includes a group derived from the structure represented by Formula (4) above. Such a condensed ring structure exhibits high carrier transport property and thus the carrier can be sufficiently transported even in a case in which the ground layer above is in contact with the photoelectric conversion layer or the electron transport layer of the organic photoelectric conversion element, as a result, a decrease in power generation efficiency can be suppressed.

Even more preferably, $Y^1$ is those having a carbazole backbone, an azacarbazole backbone, or a fluorene backbone, which exhibits high electron transport property (the following Y-5 and Y-5, N-12 to N-34, N-37, and N-38).

Preferred structures of $Y^1$ are presented below. The groups represented by N-12 to N-38, N-46, and N-47 above may be used as $Y^1$ in addition to the following Y-1 to Y-15.

Y-1

Y-2

Y-3

Y-4

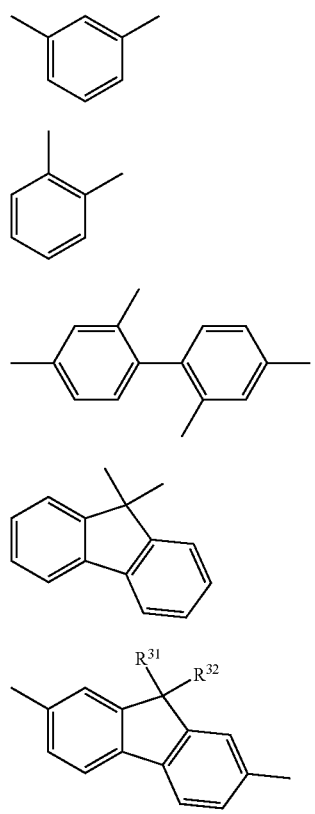

Y-5

Y-6

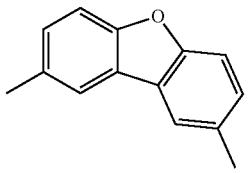

Y-7

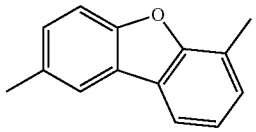

Y-8

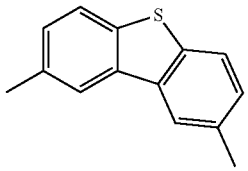

Y-9

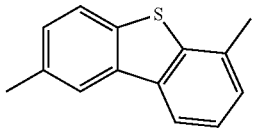

Y-10

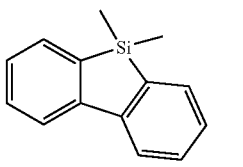

Y-11

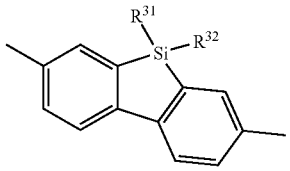

Y-12

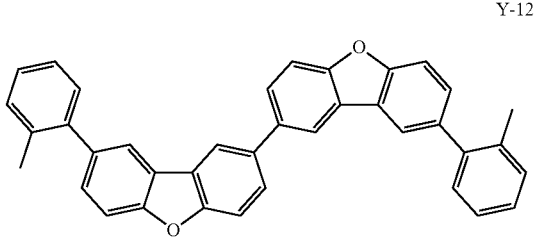

Y-13

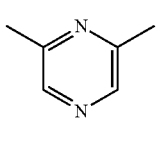

Y-14

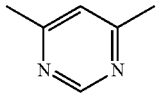

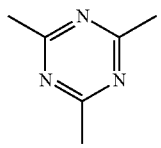

Y-15

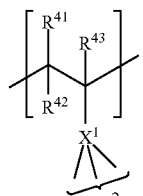

Formula (3A)

Formula (3B)

In Formulas above, $R^{31}$ and $R^{32}$ each independently represents a hydrogen atom or a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms. Specific groups thereof are the same as the groups exemplified above.

Among them, a condensed ring structure such as Y-2 to Y-5 and Y-9 to Y-12 is preferable among the above structures. This is because such a condensed ring structure exhibits high carrier transport property and thus the carrier can be sufficiently transported even in a case in which the ground layer is in contact with the photoelectric conversion layer or the electron transport layer of the organic photoelectric conversion element, as a result, a decrease in power generation efficiency can be suppressed.

In Formula (2) above, the divalent organic group as $Y^2$ is not particularly limited and is preferably a divalent substituted or unsubstituted aromatic residue. Examples thereof may include a substituted or unsubstituted arylene group having from 6 to 30 carbon atoms and a substituted or unsubstituted heteroarylene group having from 1 to 30 carbon atoms. Meanwhile, these groups may be bonded to each other via the divalent linking group described above. Specific groups of the arylene group, the heteroarylene group, and the substituent in a case in which these have a substituent are the same as those of the arylene group, the heteroarylene group, and the substituent in $Y^1$. A substituted or unsubstituted arylene group having from 6 to 12 carbon atoms or a substituted or unsubstituted heteroarylene group having from 1 to 12 carbon atoms is preferable, and more preferably $Y^2$ includes a phenylene group or a substituted or unsubstituted divalent group derived from the structure represented by Formula (4) above from the viewpoint of obtaining adequate solubility. Specifically, $Y^2$ is a divalent group represented by Y-1 to Y-14 or N-12 to N-38. In an embodiment of the present invention, $Y^2$ includes the structure represented by Formula (4) above. Such a condensed ring structure exhibits high carrier transport property and thus the carrier can be sufficiently transported even in a case in which the ground layer is in contact with the photoelectric conversion layer or the electron transport layer of the organic photoelectric conversion element, as a result, a decrease in power generation efficiency can be suppressed. Particularly preferably, $Y^2$ is a divalent group represented by Y-6 (2,6-pyridyl or the like) above from the viewpoint of obtaining adequate solubility.

The (n2+2)-valent organic group as $Y^3$ in Formula (3) above is not particularly limited. Examples thereof may include an (n2+2)-valent group represented by the following Formula (3A) or (3B).

In Formula (3A) and Formula (3B) above, the n2 numbers of lines downward the $X^1$ and $X^2$ indicate the linking sites with $A^1$, and [ ] indicate the repeating sites.

In Formula (3A) above, $R^{41}$ to $R^{43}$ represent a hydrogen atom or a methyl group. $R^{41}$ to $R^{43}$ may be the same as or different from each other.

In Formula (3A) above, in a case in which n2 is 1, $X^1$ represents a single bond (—), a substituted or unsubstituted alkylene group having from 1 to 20 carbon atoms, a substituted or unsubstituted cycloalkylene group having from 3 to 20 carbon atoms, a substituted or unsubstituted arylene group having from 6 to 30 carbon atoms, a substituted or unsubstituted heteroarylene group having from 1 to 30 carbon atoms, or a substituted or unsubstituted alkyleneoxycarbonyl group with an alkylene chain having from 1 to 20 carbon atoms. Specific groups of the arylene group, the heteroarylene group, and the substituent in a case in which these have a substituent are the same as those of the arylene group, the heteroarylene group, and the substituent in $Y^1$. In addition, specific groups of the alkylene group and the cycloalkylene group are the same as those of the divalent linking group described above. The unsubstituted alkyleneoxycarbonyl group with an alkylene chain having from 1 to 20 carbon atoms refers to "—CO—O-alkylene-" or "-alkylene-O—CO—", and the alkylene group at this time is an alkylene group having from 1 to 20 carbon atoms. Preferably, it has a form in which the carbon atom of the carbonyl group (—CO—) is bonded to the carbon atom of the main chain (in this case, an acrylic polymer is obtained). Here, the alkylene group having from 1 to 20 carbon atoms is not particularly limited, and the same alkylene groups as those described above may be exemplified. A linear or branched alkylene group having from 1 to 15 carbon atoms is preferable and a linear or branched alkylene group having from 1 to 12 carbon atoms is more preferable. In addition, the substituent is also the same as the substituent in the nitrogen-containing aromatic ring described above.

Among them, $X^1$ in a case in which n2 is 1 is preferably a single bond (—), a substituted or unsubstituted arylene group having from 6 to 30 carbon atoms, or a substituted or unsubstituted alkyleneoxycarbonyl group with an alkylene chain having from 1 to 20 carbon atoms in terms of obtaining adequate solubility, and is preferably a single bond (—), a substituted or unsubstituted arylene group having from 6 to 12 carbon atoms, or a substituted or unsubstituted alkyleneoxycarbonyl group having from 1 to 8 carbon atoms in terms of the density of the substituent that interacts with an element of Group 11.

In a case in which n2 is 2 or more, $X^1$ represents a substituted or unsubstituted (n2+1)-valent aromatic residue or a substituted or unsubstituted (n2+1)-valent aliphatic hydrocarbon residue. Specific examples thereof may include a group obtained by further removing (n2−1) hydrogen atoms from the substituted or unsubstituted alkylene group having from 1 to 20 carbon atoms, the substituted or unsubstituted cycloalkylene group having from 3 to 20 carbon atoms, the substituted or unsubstituted arylene group having from 6 to 30 carbon atoms, the substituted or unsubstituted heteroarylene group having from 1 to 30 carbon atoms.

In Formula (3B) above, $X^2$ represents an (n2+2)-valent aromatic residue or a substituted or unsubstituted (n2+1)-valent aliphatic hydrocarbon residue. Specific examples thereof may include a group obtained by further removing n2 hydrogen atoms from the substituted or unsubstituted alkylene group having from 1 to 20 carbon atoms, the substituted or unsubstituted cycloalkylene group having from 3 to 20 carbon atoms, the substituted or unsubstituted arylene group having from 6 to 30 carbon atoms, or the substituted or unsubstituted heteroarylene group having from 1 to 30 carbon atoms. A group obtained by further removing n2 hydrogen atoms from the substituted or unsubstituted arylene group having from 6 to 30 carbon atoms or the substituted or unsubstituted heteroarylene group having from 1 to 30 carbon atoms is preferable. The specific groups and substituents thereof are the same as above.

In an embodiment of the present invention, $X^2$ as $Y^3$ includes the structure represented by Formula (4) above. Such a condensed ring structure exhibits high carrier transport property and thus the carrier can be sufficiently transported even in a case in which the ground layer is in contact with the photoelectric conversion layer or the electron transport layer of the organic photoelectric conversion element, as a result, a decrease in power generation efficiency can be suppressed.

Preferred structures of $Y^3$ are presented below.

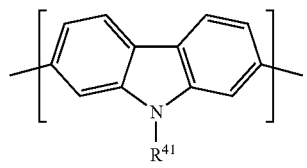
y-16

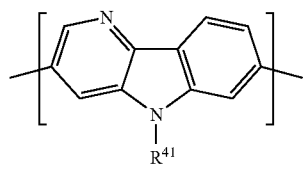
y-17

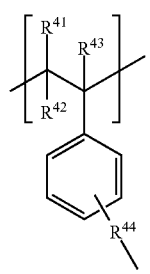
y-18

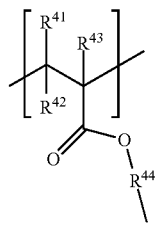
y-19

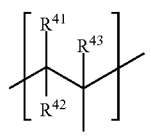
y-20

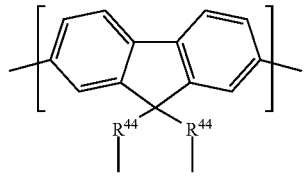
y-21

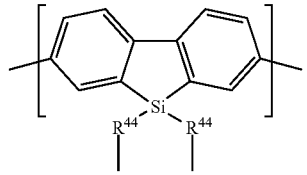
y-22

In Formulas above, $R^{41}$ to $R^{43}$ each independently represent a hydrogen atom or a methyl group.

In Formulas above, $R^{44}$ represents a single bond (—), or a substituted or unsubstituted linear or branched alkylene group having from 1 to 12 carbon atoms or an alkyleneoxycarbonyl group having from 1 to 12 carbon atoms, and is preferably a single bond (—) or a linear alkylene group having from 1 to 6 carbon atoms (for example, a methylene group, an ethylene group, or a pentamethylene group). The substituent at this time is the same as the substituent in the nitrogen-containing aromatic ring described above.

Even more preferably, $R^{44}$ is a group having a condensed ring structure such as Y-21 or Y-22 in terms of improving the carrier transport property and thus suppressing a decrease in power generation efficiency, and particularly preferably, $R^{44}$ is a group (Y-21), which has a fluorene backbone and an alkyl chain at the 9-position of fluorine, from the viewpoint of improving the solubility of the nitrogen-containing organic compound in the case of forming the ground layer by a coating method.

As described above, the nitrogen-containing organic compound may be a low molecular weight compound represented by Formula (1) (a compound that is not a polymer type) or a polymer compound (a compound that has a partial structure represented by Formula (2) or (3)), but is preferably a polymer compound. This is because the uniformity of the film quality is improved, a decrease in shunt resistance (Rsh) caused by a pinhole or the like is eliminated even at a significantly thin film thickness of 5 nm or the like, and a high fill factor (FF) is maintained, as a result, an organic photoelectric conversion element excellent in photoelectric conversion efficiency and durability is obtained in the case of a polymer compound.

The weight average molecular weight of the nitrogen-containing organic compound is not particularly limited, but a polymer compound having a weight average molecular weight of 3000 or more is preferable in terms of the uniformity of film quality, conversion efficiency, and durability. The weight average molecular weight is more preferably 4000 or more and even more preferably 5000 or more. Here, the upper limit of the weight average molecular weight of the nitrogen-containing organic compound is not particularly limited but is preferably 50,000 or less and more preferably 30,000 or less. The weight average molecular weight can be measured by gel permeation chromatography (GPC) (standard substance).

Specifically, the measurement of the weight average molecular weight (Mw) of the nitrogen-containing organic compound according to the present invention can be performed by measuring the molecular weight by GPC (gel permeation chromatography) using THF (tetrahydrofuran) as a column solvent. However, the molecular weight of the main chain may be confirmed by measuring the molecular weight of the precursor thereof (compound having a ω-bromoalkyl group as a substituent) one process before in the manufacturing process of the nitrogen-containing compound of the present invention since there are some compounds which are not soluble in THF. Meanwhile, the weight average molecular weight of the nitrogen-containing organic compound can be easily estimated from the weight average molecular weight of the precursor since the nitrogen-containing organic compound according to the present invention is obtained from the precursor by a polymer reaction and the length of the main chain does not significantly change.

Specifically, 1 ml of THF (using those subjected to degassing treatment) is added with respect to 1 mg of measurement sample and stirred using a magnetic stirrer at room temperature in order to sufficiently dissolve. Subsequently, the resultant solution is filtered with a membrane filter having a pore size of from 0.45 to 0.50 μm and then injected into the GPC (gel permeation chromatography) equipment.

The measurement conditions of GPC are as follows. That is, the column is stabilized at 40° C., THF (tetrahydrofuran) is allowed to flow at a flow rate of 1 ml per minute, and about 100 μl of sample having a concentration of 1 mg/ml is injected and measured.

As the column, commercially available polystyrene gel columns are preferably used in combination. For example, the combination of Shodex GPC KF-801, 802, 803, 804, 805, 806, and 807 manufactured by SHOWA DENKO K. K., the combination of TSKgel G1000H, G2000H, G3000H, G4000H, G5000H, G6000H, G7000H, and TSK guard column manufactured by TOSOH CORPORATION, or the like is preferable.

As the detector, a refractive index detector (RI detector) or a UV detector is preferably used. In the measurement of the molecular weight of the sample, the molecular weight distribution of the sample is calculated using the standard curve created using a monodisperse polystyrene standard particle. It is preferable to use about 10 samples as the polystyrene for standard curve creation.

In the present specification, the weight average molecular weight of the nitrogen-containing organic compound is the value measured under the following measurement conditions.

(Measurement Conditions)
Equipment: Tosoh high performance GPC system HLC-8220GPC
Column: TOSOH TSKgel Super HM-M
Detector: RI and/or UV
Eluent flow rate: 0.6 ml/minute
Sample concentration: 0.1% by mass
Sample volume: 100 μl
Standard curve: created by a standard polystyrene: the standard curve (also referred to as the calibration curve) was created using 13 samples of a standard polystyrene, STK standard polystyrene (manufactured by TOSOH CORPORATION) having a Mw of about from 1,000,000 to 500 and used to calculate the molecular weight. Here, the 13 samples preferably have almost an equal interval.

The method of producing the nitrogen-containing organic compound according to the present invention is not particularly limited, and a known production method can be applied as it is or in an appropriately modified manner. For example, the nitrogen-containing organic compound according to the present invention can be synthesized by referring to ADVANCED MATERIALS 2007, 19, 2010, or the like.

More specifically, the nitrogen-containing organic compound according to the present invention includes those having the following structures. Meanwhile, the present invention is not limited thereto. Meanwhile, in the present specification, the compound is defined by the following compound number.

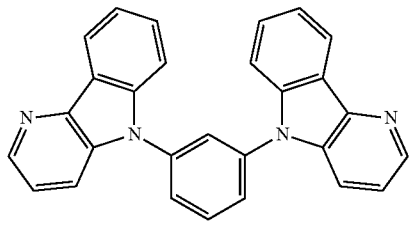

1

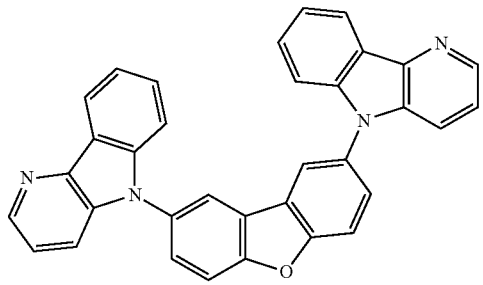

2

-continued
3
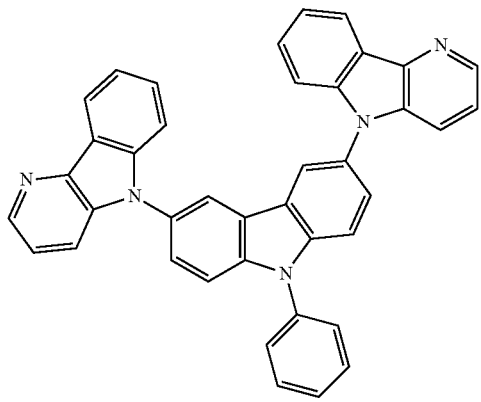
4
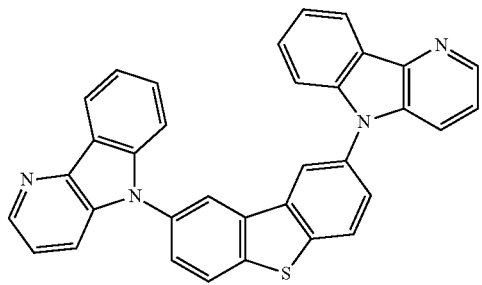
5
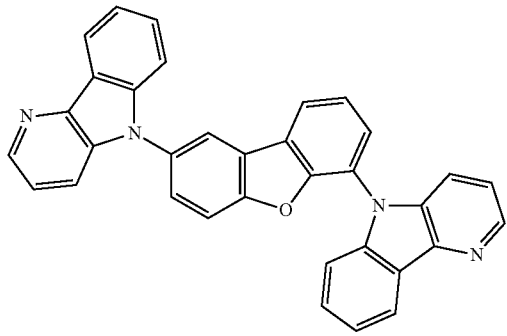
6
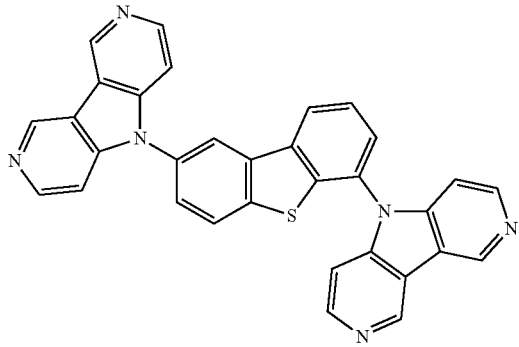
7
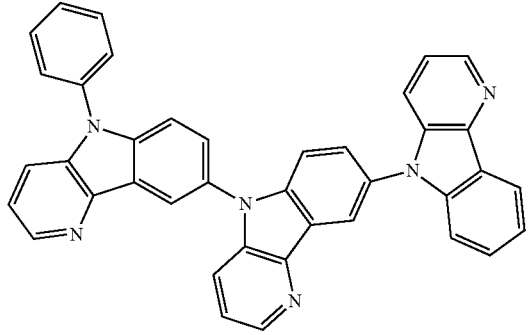
8
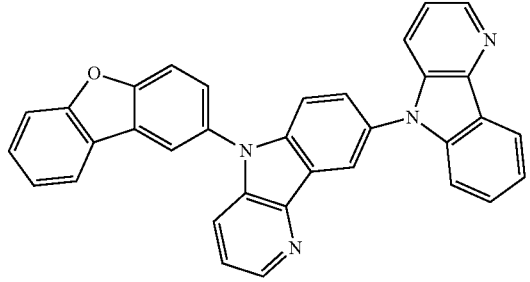
9
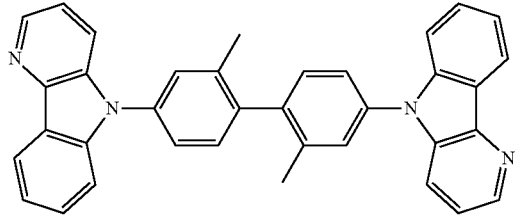
10
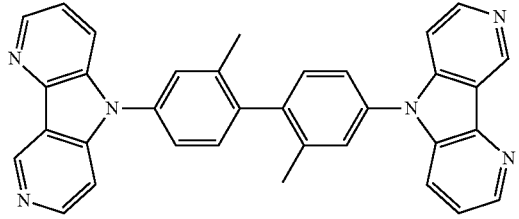
11
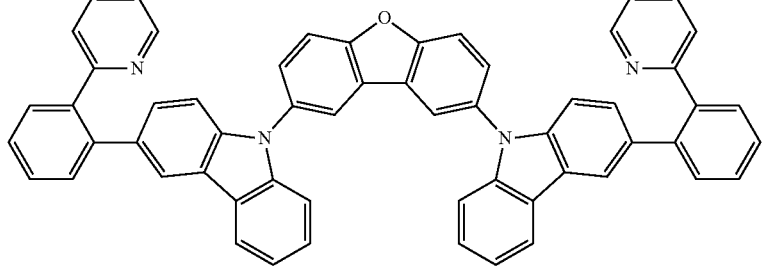

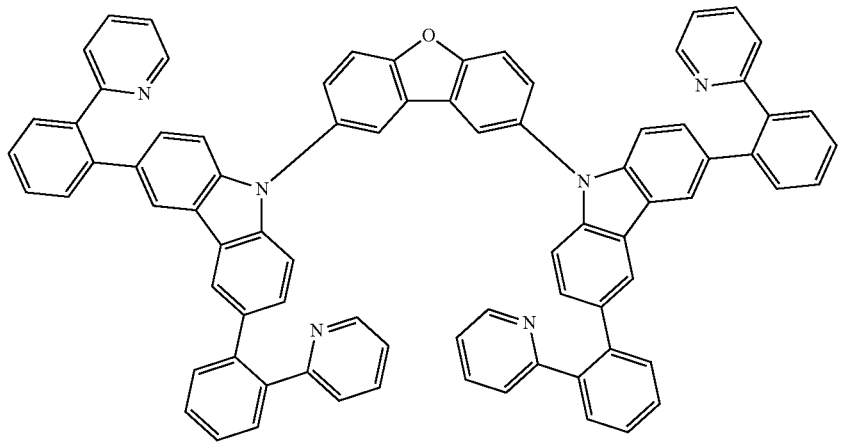
12
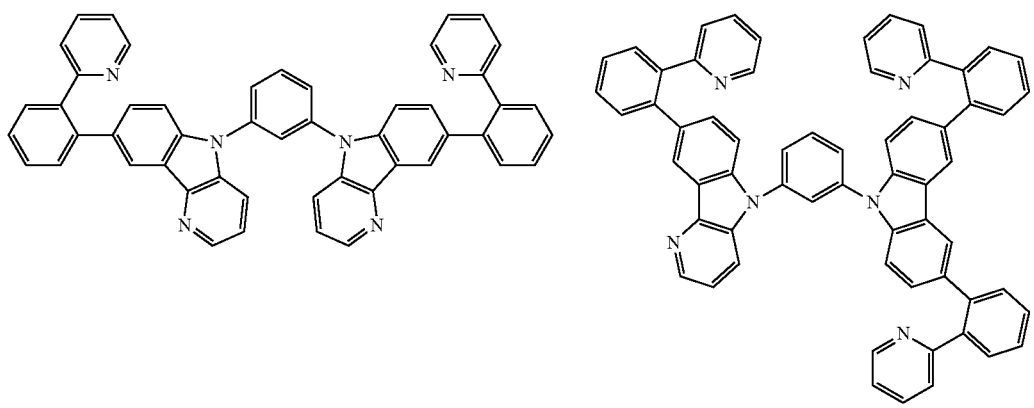
13
14
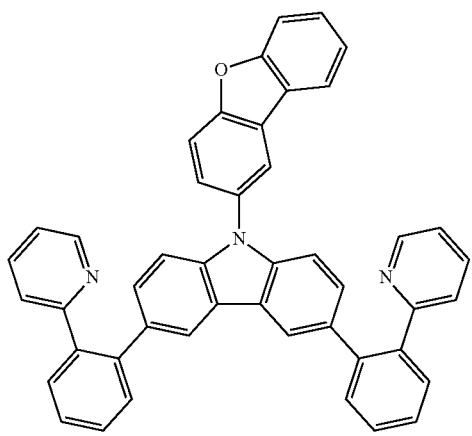
15

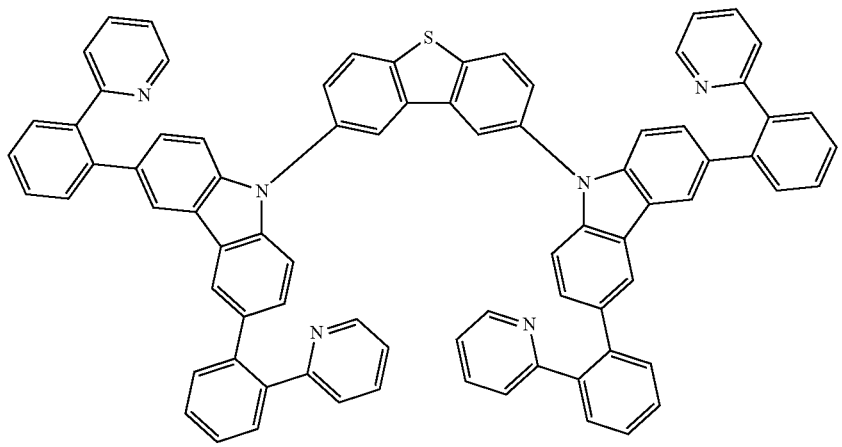
16
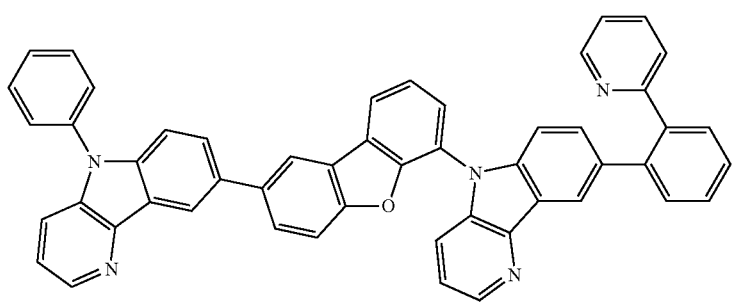
17
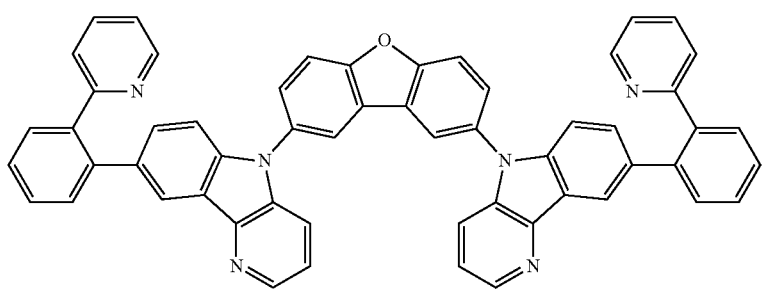
18
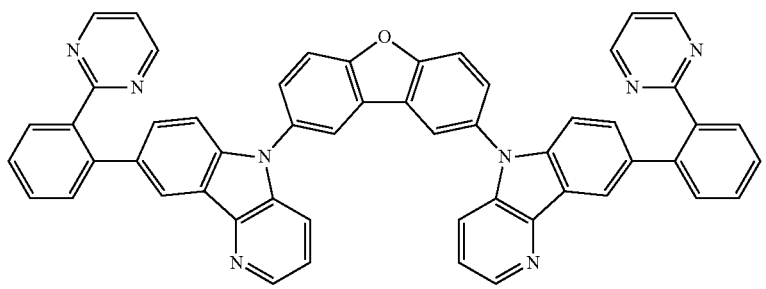
19
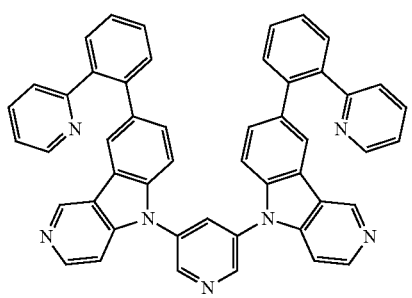
20
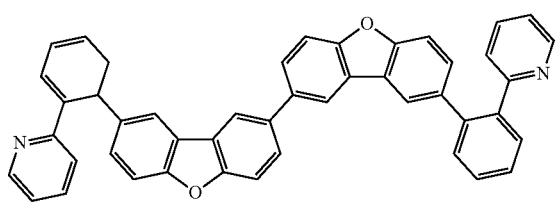
21

-continued
22
23
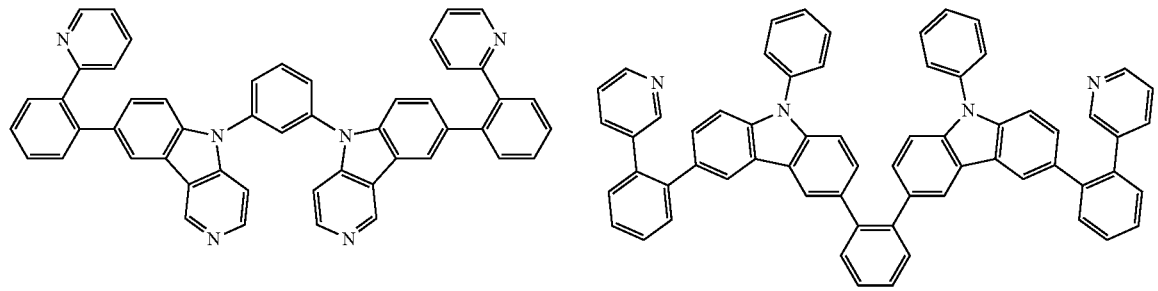
24
25
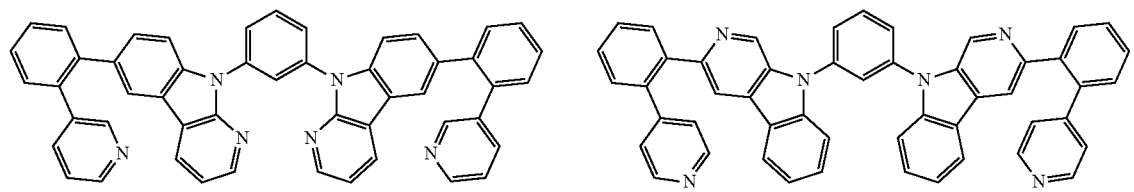
26
27
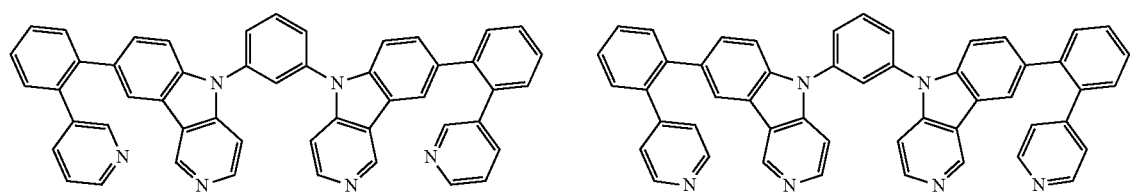
28
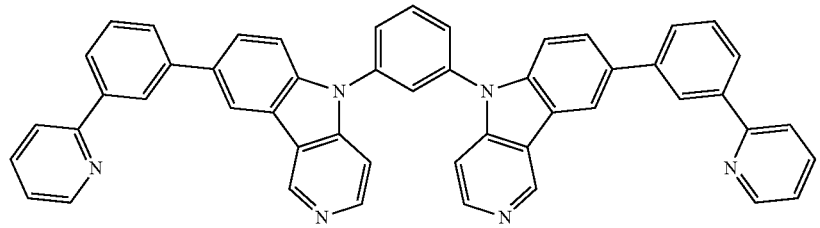
29
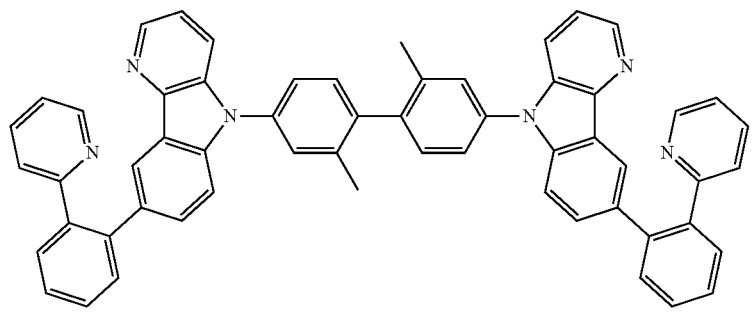
30
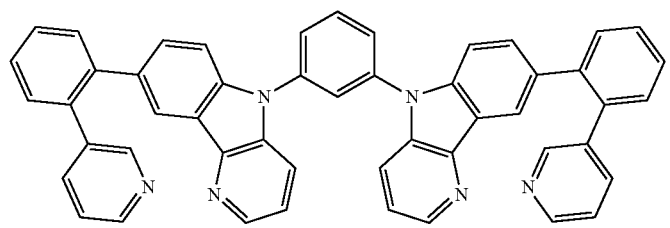

-continued
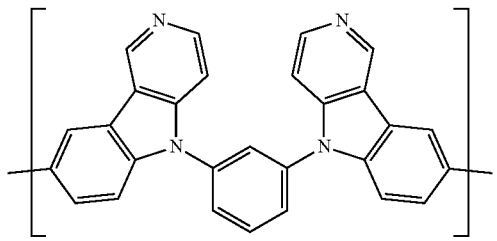
31
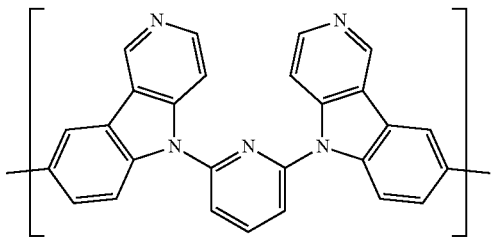
32
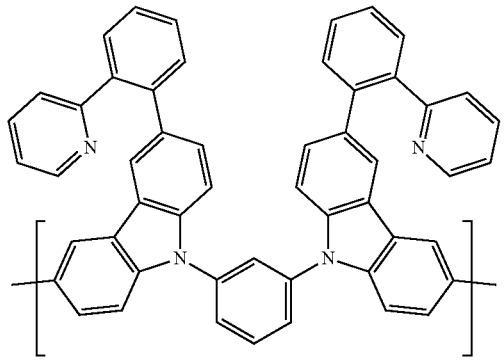
33
34
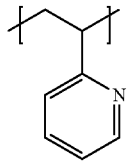
35
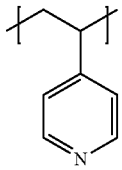
36
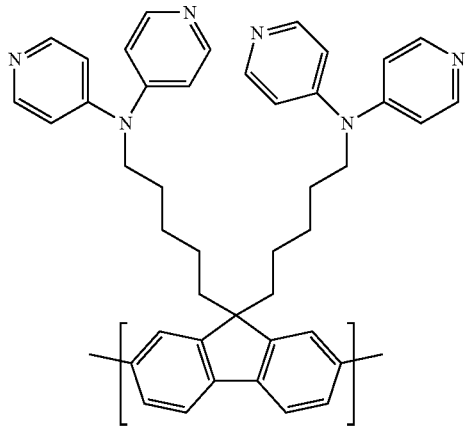
37
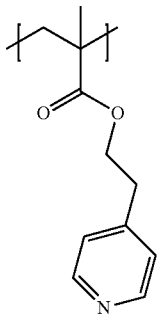
38
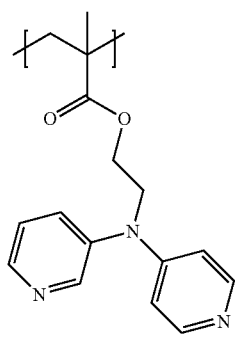
39
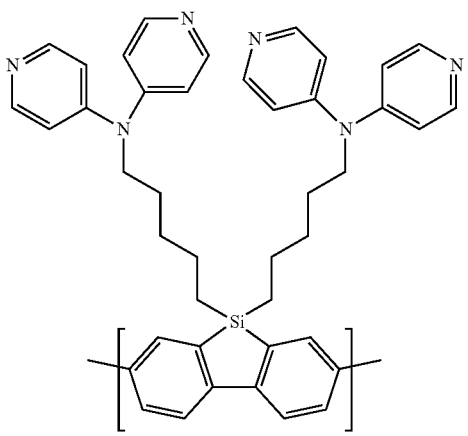
40

-continued
41
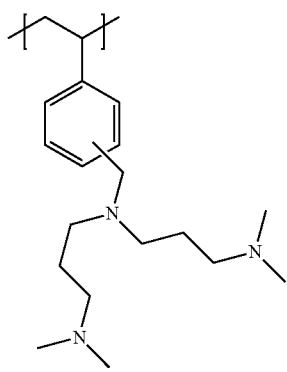
42
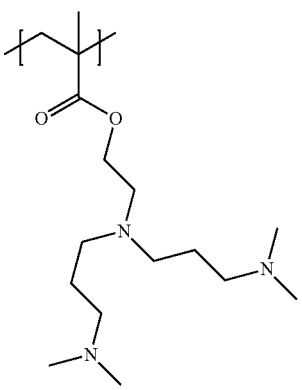
43
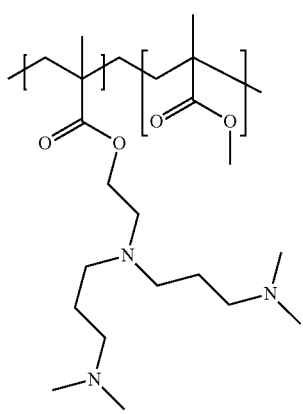
44
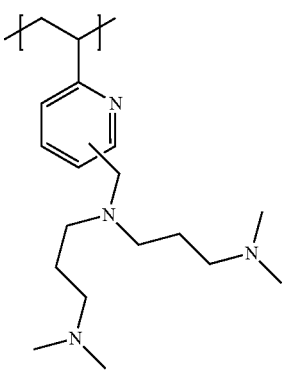
45
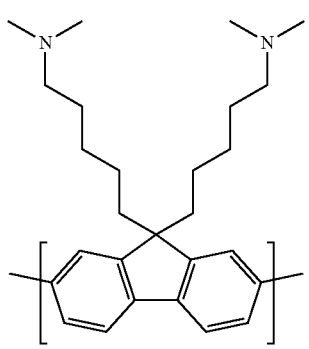
46
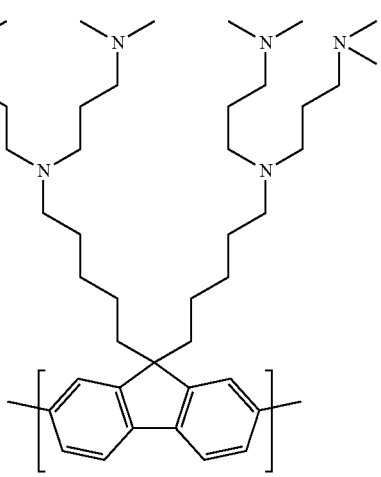

-continued
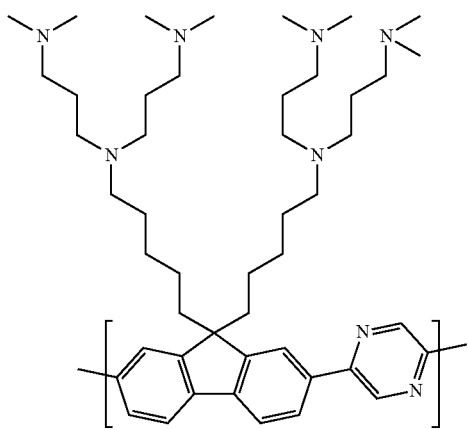
47
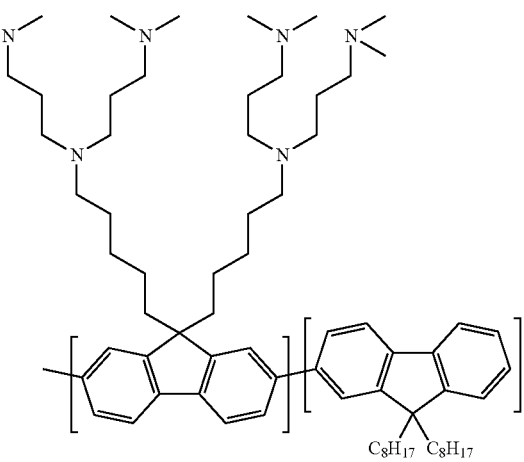
48
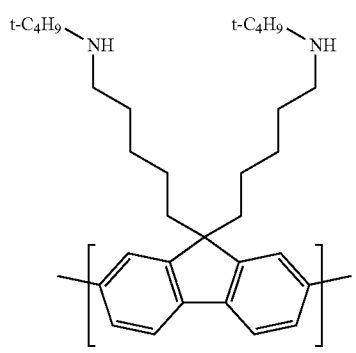
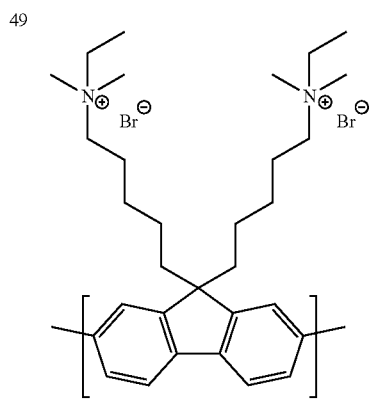
49
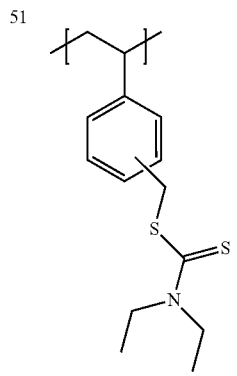
50
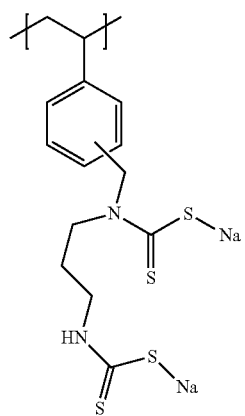
51
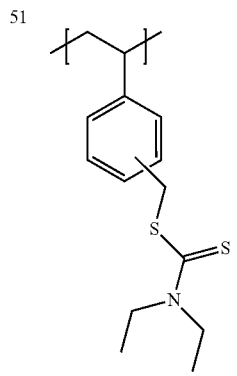
52

-continued
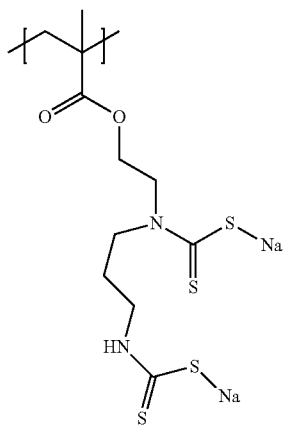
53
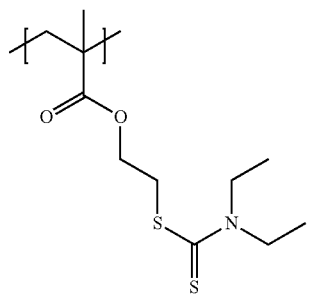
54
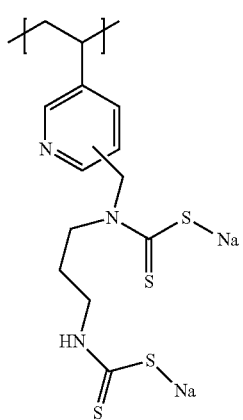
55
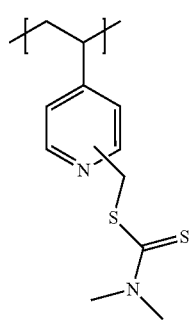
56
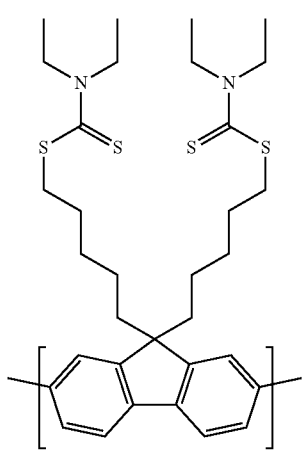
57
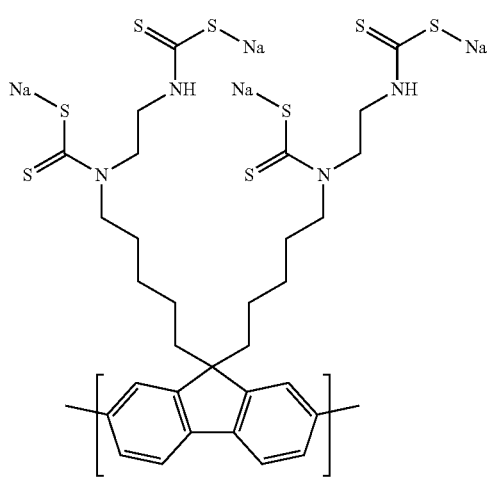
58

-continued
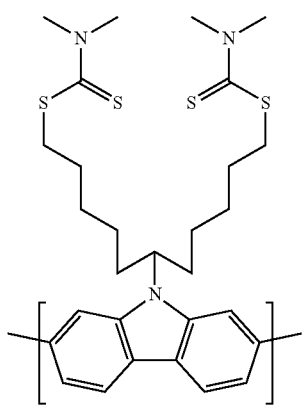
59
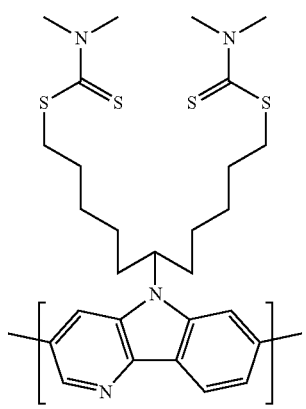
60
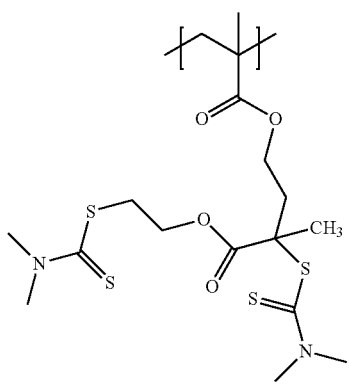
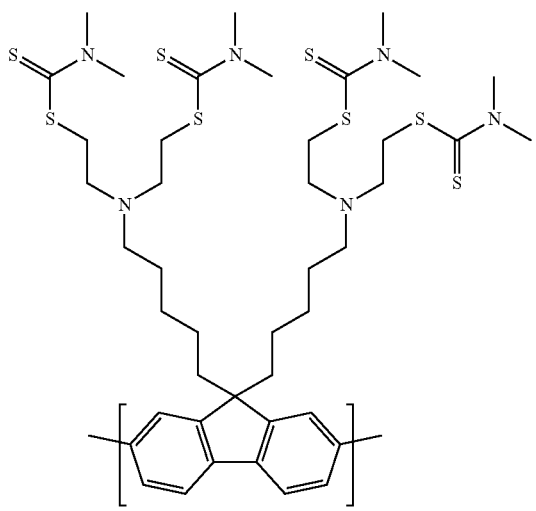
61
62
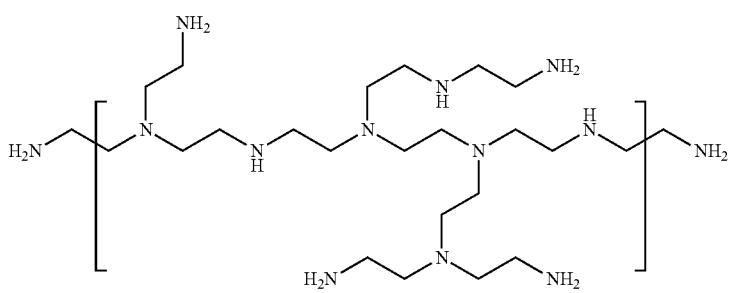
63

-continued
64
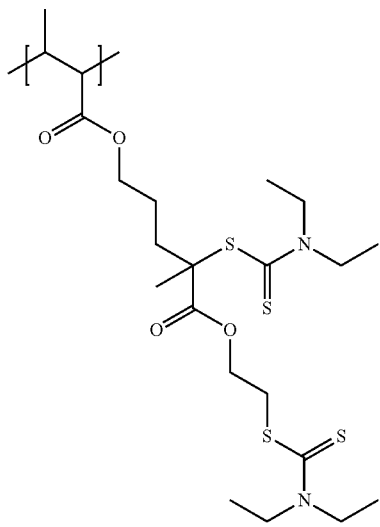
65
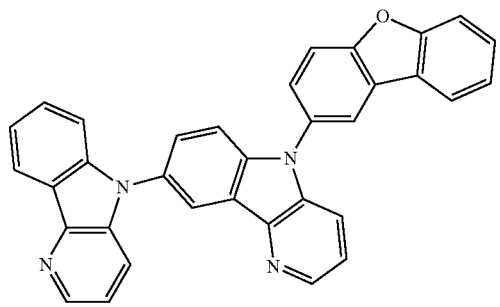
66
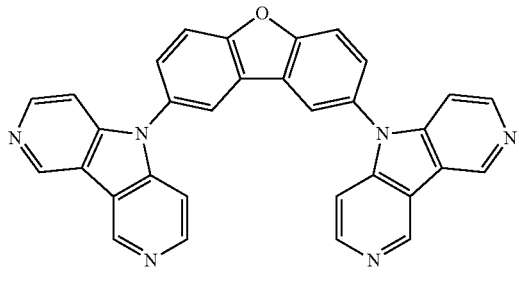
67
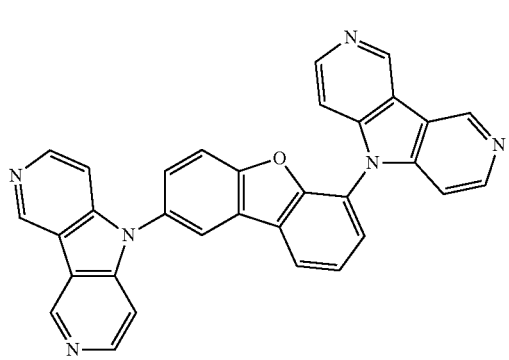
68
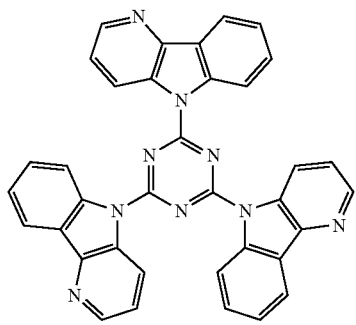
69
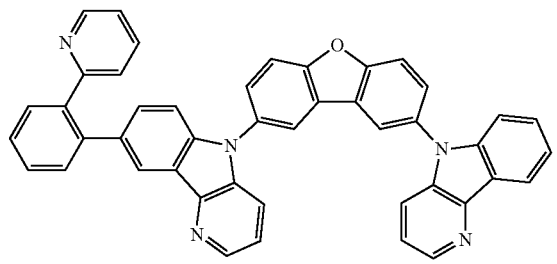
70
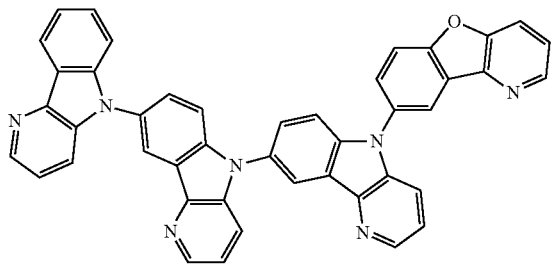
71
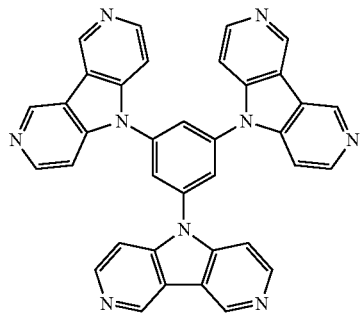

-continued
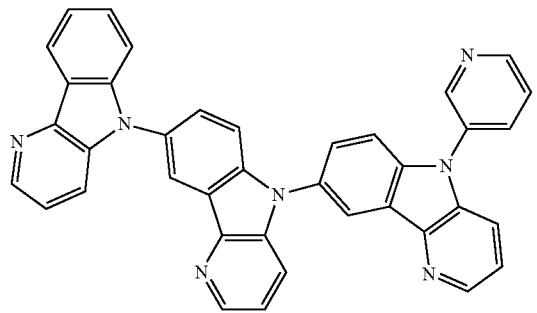
72
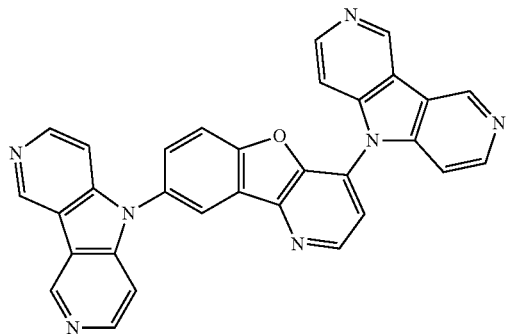
73
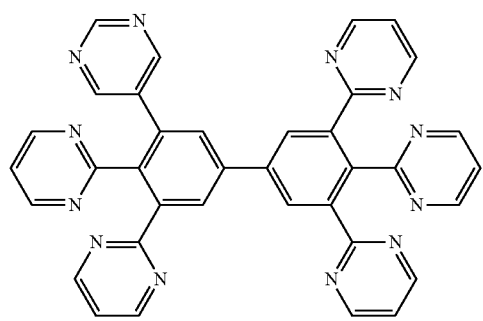
74
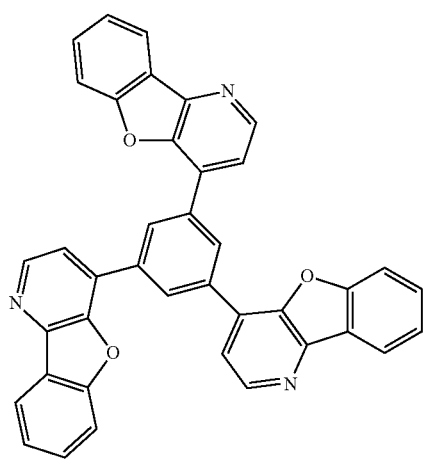
75
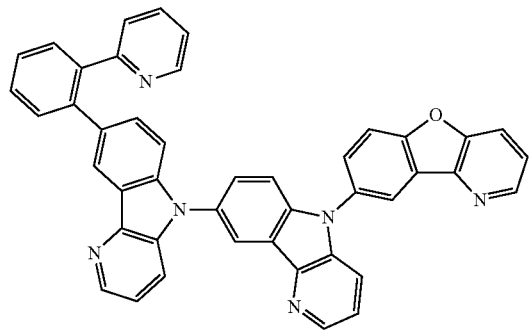
76
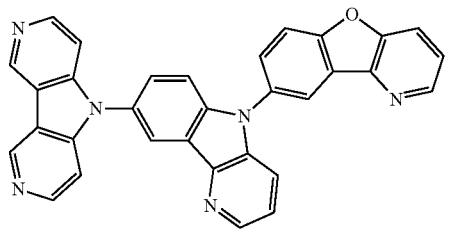
77
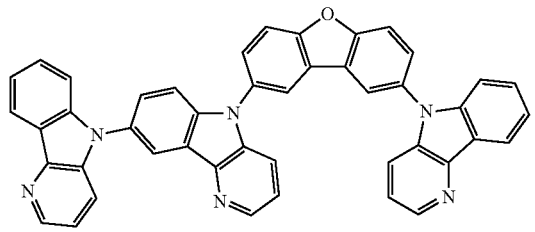
78
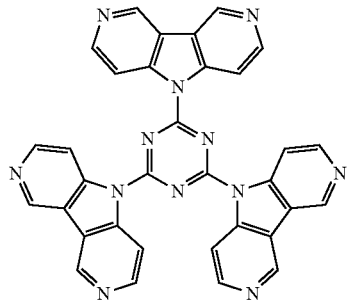
79

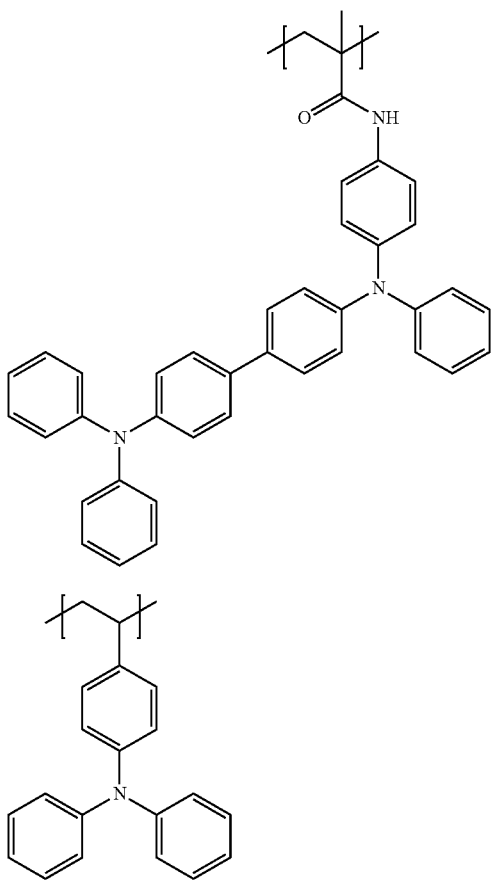

The thickness (thickness when dried) of the ground layer is not particularly limited but is usually from 1 to 2000 nm. The thickness is preferably 3 nm or more from the viewpoint of obtaining a uniform metal thin film layer. In addition, the thickness is 1000 nm or less and more preferably 200 nm or less from the viewpoint of maintaining high transmittance and low resistance. The thickness is more preferably in the range of 5 to 30 nm, even more preferably from 5 to 25 nm, and particularly preferably from 5 to 20 nm.

The ground layer may contain another material as long as the effect by the nitrogen-containing organic compound according to the present invention is not impaired. For example, in a case in which the ground layer is disposed between the photoelectric conversion layer and the metal thin film layer as an anode, the ground layer may contain another electron transporting material. In addition to this, lithium fluoride, cesium carbonate, or the like may be contained.

(Metal Thin Film Layer)

The metal thin film layer 3 is constituted to contain a metal element of Group 11 of the periodic table and has high conductivity as an electrode material and high transparency. The metal thin film layer substantially serves as a conductive material in a case in which the transparent conductive film is used as an electrode.

Specific examples of the metal element of Group 11 of the periodic table may include gold (Au), silver (Ag), and copper (Cu). These metal elements are a stable material having a deep work function and are able to improve the durability of the transparent conductive film (transparent electrode). These may be used as a simple substance or an alloy. As the alloy, there are an alloy obtained by combining at least two kinds of gold (Au), silver (Ag), and copper (Cu) and an alloy obtained by adding one or more kinds of metals such as aluminum (Al), palladium (Pd), platinum (Pt), neodymium (Nd), and bismuth (Bi) to at least one kind of gold (Au), silver (Ag), and copper (Cu). Silver, copper, or an alloy thereof is preferable, silver or a silver alloy (for example, Ag—Au, Ag—Au—Cu, Ag—Au—Nd, Ag—Bi, or the like) is more preferable, and silver is particularly preferable from the viewpoint of conductivity.

The metallic materials described above are usually opaque and thus need to be formed into a thin film in order to obtain transparency. However, in general, a metal is easily isolated in an island shape in a significantly thin region by the nucleus growth type (Volumer-Weber: VW type) film growth, and thus a metal of Group 11 (for example, silver) usually has an island constitution at 10 nm or less when deposited on a usual substrate and an insulating thin film is obtained due to the lack of continuity between the islands. Consequently, the transparency and the conductivity are in the trade-off relation in a metal film formed by a method of the related art, and thus the compatibility thereof is difficult.

On the contrary to this, in the present invention, a metal layer is formed on a ground layer exhibiting great interaction with a metal element of Group 11 of the periodic table and thus a single layer growth type (Frank-van der Merwe: FW type) film growth is possible, as a result, a transparent and highly conductive metal thin film can be obtained. Hence, it is possible to form a transparent conductive film (transparent electrode) exhibiting secure conductivity while maintaining light transmittance even at a thin film thickness.

Specifically, in an embodiment, the film thickness of the metal thin film layer 3 is from 2 to 10 nm. The metal thin film layer 3 cannot function as a conductive film since the sheet resistance thereof increases in a case in which the thickness is less than 2 nm. On the other hand, it is possible to secure sufficient visible light transmittance so as to secure transparency when the film thickness is 10 nm or less. The thickness is preferably from 5 to 8 nm from the viewpoint of achieving both the transparency and conductivity. In addition, in another embodiment, the film thickness of the metal thin film layer 3 is from 10 to 30 nm. The metal thin film layer 3 is semi-transparent when the thickness of the metal thin film layer 3 has a value within such a range, and it is possible to obtain an advantage that is suitable for a semi-transparent type (see-through type) exhibiting moderate light shielding property by using this.

The metal thin film layer 3 may also contain another material other than the metal element described above as long as the transparency and conductivity are not impaired. Specifically, a metal salt or a chelating agent such as sodium carbonate or EDTA may be added for the purpose of adjusting the hardness of the film; an anionic surfactant, a cationic surfactant, and a nonionic surfactant may be added for the purpose of adjusting the surface tension of the film; an electron transporting material capable of being codeposited such as an alkali metal compound such as lithium fluoride may be added for the purpose of reducing the electrical resistance with the organic semiconductor layer. Moreover, the solvent or the additive used for the film formation may be contained in the metal thin film layer 3 in the case of forming a metal thin film layer 3 by a die coating method, an ink jet method, or the like to be described below.

(Protective Layer)

The protective layer 4 is provided on the light incident side of the metal thin film layer 3 and has a function of suppressing the reflection of sunlight on the surface of the metal thin film layer. The metal thin film layer 3 is a material having a high refractive index despite a thin film and thus has a relatively high reflectance. It is possible to increase the quantity of light absorbed by the photoelectric conversion layer and to improve the photoelectric conversion efficiency by forming a protective layer on the light incident side of the metal thin film layer. In addition, it is also possible to suppress a decrease in photoelectric conversion efficiency due to the migration of the metal atom in the metal thin film layer consisting of an element of Group 11 of the periodic table by the protective layer.

Specifically, the protective layer 4 is formed on the metal thin film layer 3 positioned on the outermost surface in the case of using the transparent conductive film as the anode (second electrode) 12 of the organic photoelectric conversion element 10 illustrated in FIG. 1. On the other hand, the ground layer 2 is present on the substrate side of the metal thin film layer 3 and thus this ground layer 2 can suppress the reflection of light from the substrate side. In addition, in a case in which the ground layer, the hole transport layer, or the electron transport layer is positioned on both sides of the metal thin film layer, these layers may serve as a protective layer and thus it is not necessary to provide a protective layer separately as in the case of using a transparent conductive film as a cathode (first electrode) 11.

The material constituting the protective layer is preferably a material having a low refractive index so as to sufficiently suppress the reflection of sunlight. The refractive index of the protective layer is preferably from 1.5 to 1.8 and more preferably from 1.6 to 1.7.

As a specific material, a known material usable in the sealing of an organic photoelectric conversion element or a known material usable as the substrate of an organic photoelectric conversion element may be exemplified. In particular, as the protective layer in the anode (second electrode) 12 of the organic photoelectric conversion element illustrated in FIG. 1, it is preferable to use a material that forms a sealing layer. Specifically, the protective layer can be formed by a technique of sealing by adhering a cap fabricated by aluminum or glass with an adhesive, a technique of sticking a plastic film having a barrier layer of aluminum, silicon oxide, aluminum oxide or the like formed thereon on the organic photoelectric conversion element with an adhesive, a method of spin coating an organic polymer material exhibiting high gas barrier property (polyvinyl alcohol or the like), a method of piling an inorganic thin film having high gas barrier property (silicon oxide, aluminum oxide, or the like) or an organic film (Parylene (registered trademark) or the like) under vacuum, a method of laminating these integrally, and the like. Among them, an organic film composed of Parylene (registered trademark) that is a paraxylylene-based polymer is preferable in terms of a moderate refractive index and high gas barrier property. Parylene (registered trademark) is sold on the market by Specialty Coating Systems, Inc. under a trade name such as Parylene HT, Parylene C, Parylene N, Parylene D or the like. Other than these, a luminescent material such as a metal complex including tris(8-quinolinolato)aluminum complex (Alq3) or the nitrogen-containing organic compound according to the present invention described above may also be used as a protective layer.

The refractive index of these protective layers can be measured by preparing a sample provided with only the protective layer by coating and then measuring the visible light reflectance of the sample using a spectrophotometer as in Examples to be described below.

The film thickness of the protective layer is not particularly limited but is preferably 150 nm or less in terms of suppressing the decrease in transmittance due to optical interference and more preferably 10 nm or more in terms of gas barrier property. The film thickness is more preferably in the range of from 20 to 50 nm.

(Method of Manufacturing Transparent Conductive Film)

The method of manufacturing the transparent conductive film is not particularly limited. The method of manufacturing a transparent conductive film according to an embodiment of the present invention has a step of forming a ground layer by forming a film of a nitrogen-containing organic compound and a step of forming a metal thin film layer which contains a transition metal element of Group 11 of the periodic table and has a thickness of from 2 to 10 nm or from 10 to 30 nm on the ground layer. It is possible to form a continuous metal thin layer having a significantly thin film thickness in a simple manner by forming a metal thin film layer on the ground layer containing a nitrogen-containing organic compound, as a result, a transparent conductive film that exhibits both high conductivity and high transparency can be obtained.

The transparent conductive film is formed on the substrate 25 or photoelectric conversion layer 14, 14a, or 14b or the electron transport layer 27 constituting the organic photoelectric conversion element.

Examples of the method of forming the ground layer may include a deposition method and a coating method (including a casting method, a spin coating method). Among these, a coating method is preferable. The coating method is also excellent in the production rate. As a method of forming the ground layer by the coating method, for example, there is a method in which the nitrogen-containing organic compound according to the present invention and another additive (for example, another electron transporting material or the like) if necessary are dissolved in a proper solvent to prepare a solution for electron transport layer formation, subsequently, this solution is coated on a substrate, dried, and then heat treated.

The solvent is not particularly limited as long as a solvent can dissolve the nitrogen-containing organic compound or the like, and examples thereof may include an alcohol such as isopropanol or n-butanol; a halogen-containing alcohol obtained by substituting the hydrogen atom of an alcohol with a halogen atom such as hexafluoroisopropanol or tetrafluoropropanol; dimethyl sulfoxide, and dimethylformamide. One kind of these may be used singly or two or more kinds thereof may be mixed and used. Among these, an alcohol, a halogen-containing alcohol, or a mixed solvent thereof is preferable. These are excellent in terms of the coating property due to the surface tension, the drying speed, or the like and exhibit high polarity, and thus an intermediate layer can be easily formed on the photoelectric conversion layer which does not dissolve in a highly polar solvent by a coating method. Particularly, a solvent containing a fluorine-containing alcohol obtained by substituting the hydrogen atom of an alcohol with a fluorine atom is preferably used. The nitrogen-containing organic compound of the present invention is excellent in solubility in an alcohol and a fluorinated alcohol and thus it is preferable to coat and form a film using these solvents. In other words, it is preferable to form the ground layer using a solvent containing a fluorine-containing alcohol by a manufacturing method including a coating process. The concentration (solid matter concentration) of the nitrogen-containing organic compound and another additive if necessary in the solvent at this time is not particularly limited and, for example, the concentration in the solution is preferably from 0.005 to 0.5% by mass. In the present embodiment, the coating method is not limited, and examples thereof may include a spin coating method, a method of casting from a solution, a dip coating method, a blade coating method, a wire bar coating method, a gravure coating method, and a spray coating method. Moreover, it can also be patterned by a printing method such as an inkjet method, a screen printing method, a relief printing method, an intaglio printing method, an offset printing method, or a flexographic printing method. In addition, the heat treatment conditions after coating are not particularly limited as long as the electron transport layer can be formed by the conditions. For example, the temperature for heat treatment is preferably from room temperature (25° C.) to 180° C. and more preferably from 60 to 120° C. In addition, the time for heat treatment is preferably from 10 seconds to 10 minutes and more preferably from 30 seconds to 5 minutes.

In addition, a crosslinking agent is concurrently used with the nitrogen-containing organic compound according to the present invention since the nitrogen-containing organic compound is crosslinked during or after the formation of coating film by concurrently using a crosslinking agent and thus the molecular weight thereof increases, as a result, the charge transport property thereof is enhanced. Examples of the crosslinking agent may include a known crosslinking agent such as an epoxy-based crosslinking agent, an oxetane-based crosslinking agent, an isocyanate-based crosslinking agent, an alkoxysilane-based crosslinking agent, and a vinyl-based crosslinking agent. In addition, a polyhydric alcohol compound, a polyvalent amine compound, a polyvalent thiol compound, or the like is preferably concurrently used in order to promote the reaction.

As the method of forming a metal thin film layer, it is possible to use either a dry method such as a vacuum deposition method or a sputtering method; or a wet method such as a method coating a metal ink obtained by dispersing a nano-sized metal ink in a solvent, among them, a metal ink using an ink in which a binder is not used and thus an organic material does not remain after coating and drying (for example, TEC-PR-010, TEC-PR-010, TEC-CO-010, or the like manufactured by InkTec Co., Ltd., and a silver complex ink described in U.S. Pat. No. 4,452,841). A vacuum deposition method is preferably used. The conditions of deposition may be appropriately selected, for example, in the range of a degree of vacuum of $10^{-6}$ to $10^{-3}$ Pa, a deposition rate of 0.01 to 50 nm/sec, and a substrate temperature of −50 to +150° C.

(Other Electrode Materials)

An electrode material which is able to constitute the organic photoelectric conversion element of the present embodiment other than the transparent conductive film described above and known in the related art is not particularly limited as long as an electrode material is driven as a photoelectric conversion element, and an electrode material usable in the art can be appropriately adopted. Among them, the cathode is preferably constituted with a material having a relatively greater work function compared to the anode. In contrast, the anode is preferably constituted with a material having a relatively smaller work function compared to the cathode.

For example, the cathode 11 of the forwardly layered type organic photoelectric conversion element 10 illustrated in FIG. 1 is preferably constituted with an electrode material which has a relatively great work function (for example, −4.5 eV or less and preferably −4.7 eV or less) and is transparent (capable of transmitting light of 380 to 800 nm). On the other hand, an electrode material having a smaller work function (for example, −4.5 eV or less and preferably less than −4.5 eV) than the cathode is preferably used in the anode 12, and an electrode material substantially stable against oxidation can be used. Meanwhile, the anode 12 can be usually constituted with an electrode material having low light transmitting property. Meanwhile, an electrode having light transmitting property is referred to as the transparent electrode and an electrode having low light transmitting property is referred to as the counter electrode. In addition, a semi-transparent type (see-through type) organic photoelectric conversion element (organic thin film solar cell) is obtained in a case in which both the cathode and the anode are constituted with a transparent material.

In such a forwardly layered type organic photoelectric conversion element 10, examples of the electrode material used in the cathode (the first electrode) may include a metal such as gold, silver, platinum, and nickel; a transparent conductive metal oxide such as indium tin oxide (ITO), $SnO_2$, ZnO, and indium zinc oxide (IZO); and a carbon material such as a metal nanowire and a carbon nanotube. In addition, it is also possible to use a conductive polymer as an electrode material for the cathode. Examples of the conductive polymer usable in the cathode may include PEDOT: PSS, polypyrrole, polyaniline, polythiophene, polythienylenevinylene, polyazulene, polyisothianaphthene, polycarbazole, polyacetylene, polyphenylene, polyphenylene vinylene, polyacene, polyphenylacetylene, polydiacetylene, poly naphthalene, and a derivative thereof. Among these, an inorganic substance such as a metal is preferably used from the viewpoint of the hole extraction performance and the durability. One kind of these electrode materials may be used singly, or two or more kinds of these materials may be mixed and used. In addition, it is also possible to constitute the electrode by laminating two or more kinds of layers composed of the respective materials. Meanwhile, the thickness of the cathode is not particularly limited but is usually from 10 nm to 5 μm and preferably from 50 to 200 nm.

On the other hand, in the forwardly layered type organic photoelectric conversion element, examples of the electrode material used in the anode (the second electrode) may include a metal having a work function of −4.5 eV or less, an alloy, an electronically conductive compound, and a mixture thereof. Specific examples thereof may include a metal such as gold (−5.1 eV), silver (−4.7 eV), copper (−4.7 eV), zinc (−4.5 eV), platinum (−6.3 eV), and nickel (−5.0 V); a conductive metal oxide such as indium tin oxide (ITO) (−4.8 eV), ZnO (−4.5 eV), molybdenum oxide (−5.4 eV), and indium zinc oxide (IZO) (−5.3 eV); and a nanowire and nanoparticle of the metals above. Meanwhile, in the above, the values in the ( ) indicates the work function of each material. Among these, indium tin oxide (ITO), molybdenum oxide, copper, silver, and gold are preferable, indium tin oxide (ITO), molybdenum oxide, copper, and silver are more preferable, and silver is particularly preferable. The counter electrode is prevented from being oxidized and deteriorated with time and the stability of the electrode (durability) is improved when such a material is used in the electrode, as a result, the organic photoelectric conversion element can exhibit a sufficient built-in electric field enhancement effect, excellent photoelectric conversion efficiency, and durability.

One kind of these electrode materials may be used singly, or two or more kinds of these materials may be mixed and used. In addition, it is also possible to constitute the electrode by laminating two or more kinds of layers composed of the respective materials. Meanwhile, the thickness of the anode (counter electrode) is not particularly limited but is usually from 10 nm to 5 μm and preferably from 50 to 200 nm.

Meanwhile, the work function may vary about ±0.3 eV depending on the method of measurement or the surface treatment state of the thin film (presence or absence of ozone oxidation, or the like) and thus can be determined by the first ionization potential as another indicator (provided that, applicable to the case of a metal element only).

In an embodiment of the present invention, it is possible to use a metal having a great first ionization potential and a deep work function instead of aluminum or the like having a small ionization potential and easily oxidizable as the anode in a case in which an electron transport layer is provided so as to be adjacent to the anode in the forwardly layered type organic photoelectric conversion element. The first ionization potential of aluminum is 138 kcal/mol, and the ionization potential of calcium is 140 kcal/mol. As the metal having a greater first ionization potential than these easily oxidizable metals and stable, for example, gold (212 kcal/mol), platinum (208 kcal/mol), nickel (176 kcal/mol), silver (174 kcal/mol), copper (178 kcal/mol), and zinc (216 kcal/mol) may be mentioned. It is possible to obtain an organic photoelectric conversion element exhibiting high durability when such a metal having a first ionization potential greater than about 170 kcal/mol. Among these, an element of Group 11 (gold, silver, or copper) is preferable from the viewpoint of the hole extraction performance and the conductivity. It is possible to improve the conversion efficiency and the durability by using gold, silver, or copper as the anode.

In the reversely layered type organic photoelectric conversion element illustrated in FIG. 4, the anode 12 is positioned on the substrate 25 side from which light is incident and the cathode 11 is positioned on the opposite side. Hence, the cathode 11 in the form of reversely layered type illustrated in FIG. 4 is constituted with an electrode material having a relatively great work function and usually low light transmitting property. On the other hand, the anode 12 is preferably constituted with a transparent electrode material having a relatively small work function.

In such a reversely layered type organic photoelectric conversion element, as an electrode material used in the cathode (counter electrode), a metal having a work function of −4.5 eV or less, an alloy, an electronically conductive compound, and a mixture thereof are used. Such materials are the same as those exemplified in the anode of the forwardly layered type organic photoelectric conversion element described above, and gold, silver, platinum, nickel, or the like is preferably used. Among these, silver is preferably used from the viewpoint of the hole extraction performance, the reflectance of light, and the durability with respect to oxidation or the like. One kind of these electrode materials may be used singly, or two or more kinds of these materials may be mixed and used. In addition, it is also possible to constitute the electrode by laminating two or more kinds of layers composed of the respective materials. Meanwhile, the thickness of the cathode (counter electrode) is not particularly limited but is usually from 10 nm to 5 μm and preferably from 50 to 200 nm.

On the other hand, in the reversely layered type organic photoelectric conversion element, examples of the electrode material used in anode (transparent electrode) may include a metal such as gold, silver, copper, platinum, rhodium, ruthenium, aluminum, magnesium, indium, and nickel; a transparent conductive metal oxide such as indium tin oxide (ITO), $SnO_2$, ZnO, and indium zinc oxide (IZO); and a carbon material such as a metal nanowire, a carbon nanoparticle, a carbon nanowire, and a carbon nanostructure. In addition, it is also possible to use a conductive polymer as an electrode material of the cathode.

One kind of these electrode materials may be used singly, or two or more kinds of these materials may be mixed and used. In addition, it is also possible to constitute the electrode by laminating two or more kinds of layers composed of the respective materials. Among these, it is preferable to use a carbon nanowire since a transparent and highly conductive anode can be formed by a coating method. In addition, in the case of using a metallic material, it is possible to fabricate the anode (transparent electrode) by fabricating an auxiliary electrode having a thickness of about from 1 to 20 nm on the side facing the cathode (counter electrode) using, for example, aluminum, an aluminum alloy, silver, or a silver compound and then providing a film of the conductive polymer exemplified as the cathode (transparent electrode) material of the forwardly layered type organic photoelectric conversion element described above. Meanwhile, the thickness of the anode (transparent electrode) is not particularly limited but is usually from 10 nm to 5 µm and preferably from 50 to 200 nm.

[Electron Transport Layer (Also Referred to as Hole Preventing Layer or Hole Blocking Layer (HBL))]

The organic photoelectric conversion element of the present embodiment can include an electron transport layer if necessary between the photoelectric conversion layer and the cathode. The electron transport layer has a function of transporting an electron and has a property that the ability of transporting a hole is significantly low (for example, equal to or less than one-tenth of the electron mobility). The electron transport layer is provided between the photoelectric conversion layer and the anode and prevents the movement of a hole while transporting an electron to the anode, and thus it is possible to prevent the electron and the hole from recombining.

The electron transporting material used in the electron transport layer (hole blocking layer) is not particularly limited, and a material known in the related art can be used without limitation. Examples thereof may include a nitro-substituted fluorene derivative, a diphenylquinone derivative, a thiopyran dioxide derivative, carbodiimide, fluorenylidenemethane derivative, an anthraquinodimethane and anthrone derivative, and an oxadiazole derivative.

In addition, in the oxadiazole derivative exemplified as the hole transporting material below, a thiadiazole derivative obtained by substituting the oxygen atom of the oxadiazole ring with a sulfur atom and a quinoxaline derivative having a quinoxaline ring known as an electron withdrawing group can also be used as the electron transporting material. Moreover, it is also possible to use a polymer material obtained by introducing the structural unit contained in the compound above into a polymer chain or by having the compound above as the main chain of a polymer as the electron transporting material.

In addition, it is also possible to use a metal complex of 8-quinolinol derivative such as tris(8-quinolinol)aluminum (Alq3), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, or bis(8-quinolinol)zinc (Znq) and a metal complex obtained by substituting the central metal of these metal complexes with In, Mg, Cu, Ca, Sn, Ga, or Pb as the electron transporting material. Furthermore, it is also possible to preferably use metal-free phthalocyanine or metal phthalocyanine or a compound obtained by substituting the terminal of those compounds with an alkyl group or a sulfonic acid group as the electron transporting material.

In addition, it is also possible to use an electron transporting material having high n-property obtained by doping with impurities. As an example, those described in Japanese Patent Application Laid-Open No. H4-297076, Japanese Patent Application Laid-Open No. H10-270172, Japanese Patent Application Laid-Open No. 2000-196140, Japanese Patent Application Laid-Open No. 2001-102175, J. Appl. Phys., 95, 5773 (2004), or the like may be mentioned. As specific examples, an aromatic diamine compound such as N,N'-bis(3-methylphenyl)-(1,1'-biphenyl)-4,4'-diamine (TPD) or 4,4'-bis[N-(naphthyl)-N-phenylamino]biphenyl (α-NPD) or a derivative thereof; oxazole, oxadiazole, triazole, imidazole, imidazolone, a stilbene derivative, a pyrazoline derivative, tetrahydroimidazole, polyarylalkane, butadiene, 4,4',4"-tris(N-(3-methylphenyl)N-phenylamino) triphenylamine (m-MTDATA), a porphyrin compound such as porphine, tetraphenylporphine copper, phthalocyanine, copper phthalocyanine, and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, and a silazane derivative can be used, and among polymer materials, a polymer such as phenylene vinylene, fluorene, carbazole, indole, pyrene, pyrrole, picoline, thiophene, acetylene, and diacetylene or a derivative thereof can be preferably used.

Meanwhile, two or more kinds of these electron transporting materials may be used concurrently. In addition, it is also possible to constitute the electron transport layer by laminating two or more kinds of layers composed of the respective materials.

Meanwhile, the ground layer constituting the transparent conductive film of the present invention may serve as the electron transport layer. Hence, in the forwardly layered type organic photoelectric conversion element of an embodiment of the present invention (element illustrated in FIG. 1 or FIG. 5), the ground layer can also serve as the electron transport layer 27 in the case of using a transparent conductive film of the present invention as the second electrode 12. By virtue of this, it is possible to omit the electron transport layer of the related art. In addition, it is possible to further improve the electron transport performance and the hole blocking performance in the case of further providing an electron transport layer between the ground layer and the photoelectric conversion layer.

The method of forming the electron transport layer is not particularly limited and a known manufacturing method can be applied as it is or in an appropriately modified manner.

The thickness (thickness when dried) of the electron transport layer is not particularly limited but is usually from 1 to 2000 nm. The thickness is preferably 3 nm or more from the viewpoint of enhancing the leakage preventing effect. In addition, the thickness is preferably 1000 nm or less and more preferably 200 nm or less from the viewpoint of maintaining the high transmittance and the low resistance. More preferably, the thickness is in the range of from 5 to 20 nm.

The conductivity of the electron transport layer is generally preferred to be high. The ability to prevent the hole from moving decreases when the conductivity is too high, and thus rectification may decrease. Consequently, the conductivity of the electron transport layer is preferably from $10^{-5}$ to 100 S/cm and more preferably from $10^{-4}$ to 1 S/cm.

(Hole Transport Layer (Also Referred to as Electron Blocking Layer))

The organic photoelectric conversion element of the present invention may include a hole transport layer between the photoelectric conversion layer and the anode if necessary. The hole transport layer has a function of transporting a hole and has a property that the ability of transporting an electron is significantly low (for example, equal to or less than one-tenth of the hole mobility). The hole transport layer is provided between the photoelectric conversion layer and the cathode and prevents the movement of an electron while transporting a hole to the cathode, and thus it is possible to prevent the electron and the hole from recombining.

The hole transporting material used in the hole transport layer is not particularly limited, and a material usable in the art can be appropriately adopted. Examples thereof may include a triazole derivative, an oxadiazole derivative, an imidazole derivative, a polyarylalkane derivative, a pyrazoline derivative, and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, or a conductive polymer oligomer, and particularly thiophene oligomer.

In addition, it is possible to use a porphyrin compound, an aromatic tertiary amine compound, a styrylamine compound, and the like in addition to these, among these, an aromatic tertiary amine compound is preferably used. Meanwhile, in some cases, a hole transport layer may be formed using an inorganic compound such as a metal oxide of molybdenum, vanadium, and tungsten or a mixture thereof.

Meanwhile, among these metal oxides, vanadium oxide, molybdenum oxide, or the like is preferable since the work function thereof is appropriate, but it is known that the work function of these metals having a large oxidation number, particularly molybdenum oxide generally, significantly changes after deposition (Appl. Phys. Lett. 96, p 243307, 2010), and the work function is favorable (to −5.4 eV) immediately after the deposition but is rapidly deepened (to −6.0 eV) when the metal is exposed to oxygen or the like and thus becomes the trap of carrier transport. The rapid change in the work function as described above is suppressed when the thin film of the conjugated polymer compound of the present invention is formed with respect to such an unstable hole transport layer showing a severe time course, and thus it is possible to improve the durability of the organic thin film photoelectric conversion element using a metal oxide as a hole transport layer.

Moreover, it is also possible to use a polymer material obtained by introducing the structural unit contained in the compound above into a polymer chain or by having the compound above as the main chain of a polymer as the hole transporting material. In addition, it is also possible to use a p-type hole transporting material described in Japanese Patent Application Laid-Open No. H11-251067 and J. Huang et. al., Applied Physics Letters, 80 (2002), p. 139.

In addition, it is also possible to use a hole transporting material having a high p-property obtained by doping with impurities. As an example, a material described in Japanese Patent Application Laid-Open No. H4-297076, Japanese Patent Application Laid-Open No. 2000-196140, Japanese Patent Application Laid-Open No. 2001-102175, J. Appl. Phys., 95, 5773 (2004), or the like may be mentioned. Among those, PEDOT (poly-3,4-ethylenedioxythiophene)-PSS (polystyrene sulfonic acid) and polyaniline are preferable. Meanwhile, one kind of these hole transporting materials may be used singly or two or more kinds thereof may be used concurrently. In addition, it is also possible to constitute the hole transport layer by laminating two or more kinds of layers composed of the respective materials.

The method of forming the hole transport layer is not particularly limited and a known manufacturing method can be applied as it is or in an appropriately modified manner.

The thickness of the hole transport layer is not particularly limited and is usually from 1 to 2000 nm. The thickness is preferably 5 nm or more from the viewpoint of enhancing the leakage preventing effect. In addition, the thickness is preferably 1000 nm or less and more preferably 200 nm or less from the viewpoint of maintaining the high transmittance and the low resistance.

The conductivity of the hole transport layer is generally preferred to be high. The ability to prevent the electron from moving decreases when the conductivity is too high, and thus rectification may decrease. Consequently, the conductivity of the hole transport layer is preferably from $10^{-5}$ to 1 S/cm and more preferably from $10^{-4}$ to $10^{-2}$ S/cm.

[Another Intermediate Layer (Charge Recombination Layer; Intermediate Electrode)]

In the tandem type organic photoelectric conversion element (multi-junction type) having two or more photoelectric conversion layers as illustrated in FIG. 5, another intermediate layer (also referred to as the charge recombination layer and the intermediate electrode) is disposed between the photoelectric conversion layers.

The material used in another intermediate layer is not particularly limited as long as a material exhibits both conductivity and light transmitting property, and it is possible to use a transparent metal oxide such as ITO, AZO, FTO, and titanium oxide, a metal such as Ag, Al, and Au, a carbon material such as a carbon nanoparticle and a carbon nanowire, a conductive polymer such as PEDOT: PSS and polyaniline, and the like which are exemplified as the electrode materials described above. One kind of these materials may be used singly or two or more kinds thereof may be used concurrently. In addition, it is also possible to constitute the intermediate layer by laminating two or more kinds of layers composed of the respective materials.

The conductivity of another intermediate layer is preferred to be high from the viewpoint of charge transport, and specifically, the conductivity is preferably from 5 to 50000 S/cm and more preferably from 100 to 10000 S/cm. In addition, the thickness of the charge recombination layer is not particularly limited but is preferably from 1 to 1000 nm and preferably from 5 to 50 nm. The leakage can be suppressed when the thickness is 1 nm or more. On the other hand, it is possible to increase the transparency when the thickness is 1000 nm or less.

Meanwhile, it is possible to obtain a combination acts as an intermediate electrode (charge recombination layer) by laminating some of the hole transport layers and the electron transport layers described above in an appropriate combination, and an intermediate layer having such a constitution is also preferable. In other words, in an embodiment of the present invention, it is possible to use a transparent conductive film according to the present invention as another intermediate layer (intermediate electrode). In other words, the charge recombination layer 38 illustrated in FIG. 5 may be the transparent conductive film 1A illustrated in FIG. 2. At this time, it is preferable to dispose the ground layer on the first photoelectric conversion layer 14a side and the metal thin film layer on the second photoelectric conversion layer 14b side. In such a case, the ground layer containing a nitrogen-containing organic compound may function as an electron transport layer. As a still more preferred embodiment, the intermediate layer 38 further has a hole transport layer on the metal thin film layer of the transparent conductive film 1A. In other words, the organic photoelectric conversion element 30 preferably has a hole transport layer between the metal thin film layer of the transparent conductive film 1A and the second photoelectric conversion layer 14b. It is preferable to use a p-type conductive polymer material exhibiting high conductivity and a high acidity as such a hole transport layer of the intermediate layer of such a tandem type. Examples of the p-type conductive polymer material exhibiting high conductivity and a high acidity may include a conductive polymer such as PEDOT (poly-3,4-ethylenedioxythiophene)-PSS (polystyrene sulfonic acid) and polyaniline. The hole transport layer containing these p-type conductive polymer material exhibiting high conductivity and a high acidity and the ground layer containing a nitrogen-containing organic compound according to the present invention are usually laminated such that the electron transport layer (ground layer) is laminated after laminating the hole transport layer in the forwardly layered tandem type and the hole transport layer is laminated after laminating the electron transport layer (ground layer) in the reversely layered tandem type.

[Photoelectric Conversion Layer]

The organic photoelectric conversion element 10 of the present embodiment essentially includes a photoelectric conversion layer 14 between the anode 12 and cathode 11 described above. The photoelectric conversion layer has a function of converting light energy into electrical energy by utilizing the photovoltaic effect.

In the embodiments illustrated in FIG. 1, FIG. 4, and FIG. 5, the photoelectric conversion layer 14 essentially includes a p-type organic semiconductor material and an n-type organic semiconductor material. An exciton is generated when light is absorbed by these photoelectric conversion materials, and this exciton is charge separated into a hole and an electron at the pn junction interface.

<p-Type Semiconductor Material>

Examples of the p-type organic semiconductor material used in the photoelectric conversion layer may include various condensed polycyclic aromatic low molecular weight compounds or conjugated polymers.

Examples of the condensed polycyclic aromatic low molecular weight compound may include a compound such as anthracene, tetracene, pentacene, hexacene, heptacene, chrysene, picene, fulminene, pyrene, peropyrene, perylene, terylene, quaterrylene, coronene, ovalene, circumanthracene, bisanthene, zethrene, heptazethrene, pyranthrene, bioranthene, isobioranthene, circobiphenyl, and an anthradithiophene, porphyrin or copper phthalocyanine, a tetrathiafulvalene (TTF)-tetracyanoquinodimethane (TCNQ) complex, a bis(ethylenedithio)tetrathiafulvalene (BEDTTTF)-perchloric acid complex, and a derivative and a precursor thereof.

In addition, examples of the derivative having the condensed polycycle above may include a pentacene derivative having a substituent described in International Publication WO 03/16599 Pamphlet, International Publication WO 03/28125 Pamphlet, U.S. Pat. No. 6,690,029, Japanese Patent Application Laid-Open No. 2004-107216, or the like, a pentacene precursor described in the specification of U.S. Patent Application Laid-Open No. 2003/136964 or the like, an acene-based compound substituted with a trialkylsilylethynyl group described in J. Amer. Chem. Soc., Vol. 127, No. 14, p 4986, J. Amer. Chem. Soc., Vol. 123, p 9482, J. Amer. Chem. Soc., Vol. 130 (2008), No. 9, p 2706, or the like. Alternatively, it is possible to exemplify a material in which a soluble substituent is insolubilized (pigmented) through a reaction by applying energy such as heat as described in the specification of U.S. Patent Application Laid-Open No. 2003/136964, Japanese Patent Application Laid-Open No. 2008-16834, and the like.

Examples of the conjugated polymer may include a polymer material such as a polythiophene such as poly3-hexylthiophene (P3HT) and an oligomer thereof or a polythiophene having a polymerizable group described in Technical Digest of the International PVSEC-17, Fukuoka, Japan, 2007, P 1225, a polythiophene copolymer such as a polythiophene-thienothiophene copolymer described in Nature Material, (2006) vol. 5, p 328, a polythiophene-diketopyrrolopyrrole copolymer described in the specification of International Publication WO 2008/000 664, a polythiophene-thiazolothiazole copolymer described in Adv. Mater., 2007, p 4160, PCPDTBT described in Nature Mat., Vol. 6 (2007), p 497, and an -conjugated polymer such as polypyrrole and an oligomer thereof, polyaniline, polyphenylene and an oligomer thereof, polyphenylenevinylene and an oligomer thereof, polythienylenevinylene and an oligomer thereof, polyacetylene, polydiacetylene, polysilane, and polygermane.

In addition, as an oligomer material but not a polymer material, it is possible to preferably use an oligomer such as α-sexithiophene α,ω-dihexyl-α-sexithiophene, α,ω-dihexyl-α-quinquethiophene, or α,ω-bis(3-butoxypropyl)-α-sexithiophene, which is a thiophene hexamer.

More preferably, a p-type conjugated polymer is a copolymer having an electron-donating group (donor unit) and an electron-withdrawing group (acceptor unit) in the main chain. More specifically, the p-type conjugated polymer has a structure polymerized such that the donor unit and the acceptor unit are alternately arranged. In this manner, it is possible to expand the absorption region of the p-type organic semiconductor to a long wavelength region by alternately arranging the donor unit and the acceptor unit. In other words, the p-type conjugated polymer is able to absorb light in a long wavelength region (for example, 700 to 1000 nm), in addition to the absorption region (for example, 400 to 700 nm) of the p-type organic semiconductor of the related art, and thus the radiant energy over a wide range of the solar spectrum can be efficiently absorbed.

As the donor unit which may be contained in the p-type conjugated polymer, a unit having a shallower LUMO level or HOMO level than the hydrocarbon aromatic ring (benzene, naphthalene, anthracene, or the like) having the same number of electrons can be used without limitation. Examples thereof may include a unit containing a heterocyclic 5-membered ring such as a thiophene ring, a furan ring, a pyrrole ring, a cyclopentadiene, or a silacyclopentadiene, and a condensed ring thereof.

Specific examples thereof may include fluorene, silafluorene, carbazole, dithienocyclopentadiene, dithienosilacyclopentadiene, dithienopyrrole, and benzodithiophene.

On the other hand, examples of the acceptor unit which may be contained in the p-type conjugated polymer may include a quinoxaline skeleton, a pyrazinoquinoxaline skeleton, a benzothiadiazole skeleton, a benzoxadiazole skeleton, a benzoselenadiazole skeleton, benzotriazole skeleton, a pyridothiadiazole skeleton, a thienopyrazine skeleton, a phthalimide skeleton, 3,4-thiophenedicarboxylic acid imide skeleton, a isoindigo skeleton, a thienothiophene skeleton, a diketopyrrolopyrrole skeleton, a 4-acylthieno[3,4-b]thiophene skeleton, a thienopyrroledione skeleton, a thiazolothiazole skeleton, and a pyrazolo[5,1-c][1,2,4]triazole skeleton. Meanwhile, as the donor unit or the acceptor unit contained in the p-type conjugated polymer of the present embodiment, one kind thereof may be used singly or two or more kinds thereof may be concurrently used.

In the present embodiment, examples of the preferred p-type conjugated polymer may include a polythiophene-thienothiophene copolymer described in Nature Material, (2006) vol. 5, p 328, a polythiophene-diketopyrrolopyrrole copolymer described in International Publication WO 08/000664 Pamphlet, a polythiophene-thiazolothiazole copolymer described in Adv. Mater., 2007, p 4160, a dithienocyclopentadiene derivative such as PCPDTBT described in Nature Mat. vol. 6 (2007), p 497, a dithienocyclopentadiene derivative described in U.S. Pat. No. 8,008, 421, and a dithienosilole derivative described in U.S. Pat. No. 8,008,421 or the like.

Among these, a material capable of forming a thick power generation layer having high mobility as described in Appl.

Phys. Lett. Vol. 98, p 043301 is preferable. It is possible to obtain high external quantum efficiency in the entire spectral region by the use of a material capable of forming a thick power generation layer, and the fill factor does not decrease since mobility is high even if the power generation layer is thick (built-in electric field is reduced), and thus both the high external quantum efficiency and the fill factor can be achieved and a highly efficient element can be obtained.

In other words, specifically, the p-type organic semiconductor material preferably has a structure represented by the following Formula (5).

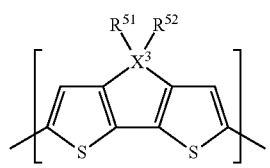

Formula (5)

In Formula (5) above, $X^3$ represents a carbon atom, a silicon atom, or germanium, $R^{51}$ and $R^{52}$ each independently represent an alkyl group, a cycloalkyl group, an aryl group, or a heteroaryl group which is substituted or unsubstituted. Here, $R^{51}$ and $R^{52}$ may be the same as or different from each other. In addition, $R^{51}$ and $R^{52}$ in each structural unit may be the same as or different from each other. In Formula (5) above, the alkyl group, the cycloalkyl group, the aryl group, and the heteroaryl group which are substituted or unsubstituted have the same definition as the substituted or unsubstituted cycloalkyl group having from 3 to 20 carbon atoms, the substituted or unsubstituted aryl group having from 6 to 30 carbon atoms, and the substituted or unsubstituted heteroaryl group having from 1 to 30 carbon atoms in Formula (4) described above, respectively, and thus the description thereof will not be presented here.

The p-type organic semiconductor material is preferably a compound having a silicon atom (Si) as $X^3$ in Formula (5) above in terms of ease of synthesis and easily obtaining a material exhibiting high crystallinity and high mobility.

The molecular weight of the p-type conjugated polymer is not particularly limited, but the number average molecular weight thereof is preferably from 5,000 to 500,000, more preferably from 10,000 to 100,000, and even more preferably from 15000 to 50000. The effect of the fill factor improvement is even more remarkable when the number average molecular weight is 5,000 or more. On the other hand, the solubility of p-type conjugated polymer is improved when the number average molecular weight is 500000 or less, and thus it is possible to increase the productivity. Meanwhile, in the present specification, the value measured by gel permeation chromatography (GPC) is adopted as the number average molecular weight.

Meanwhile, the photoelectric conversion layer of the present invention may include another p-type organic semiconductor material in addition to the p-type conjugated polymer described above. Examples of such another p-type organic semiconductor material may include a metal complex having a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a condensed aromatic carbocyclic compound (a naphthalene derivative, an anthracene derivative, a phenanthrene derivative, a tetracene derivative, a pyrene derivative, a perylene derivative, or a fluoranthene derivative), and a nitrogen-containing heterocyclic compound as a ligand. However, the mass proportion of the p-type conjugated polymer in the p-type organic semiconductor material contained in the photoelectric conversion layer is preferably 5% by mass or more, more preferably 10% by mass or more, even more preferably 50% by mass or more, particularly preferably 90% by mass or more, and most preferably 100% by mass from the viewpoint of remarkably exerting the effect of the present invention.

In the present invention, the band gap of the p-type organic semiconductor material contained in the photoelectric conversion layer is preferably 1.8 eV or less and more preferably from 1.6 to 1.1 eV. It is possible to absorb sunlight widely when the band gap is 1.8 eV or less. On the other hand, the open circuit voltage Voc (V) is easily obtained when the band gap is 1.1 eV or more, and thus the conversion efficiency can be improved. Meanwhile, in the present embodiment, one kind of p-type organic semiconductor may be used singly or two or more kinds thereof may be used concurrently.

<n-Type Organic Semiconductor Material>

The n-type organic semiconductor material used in the photoelectric conversion layer of the present embodiment is not particularly limited as long as a material is an acceptor (electron-accepting) organic compound, and a material usable in the art can be appropriately adopted. Examples of such a compound may include fullerene, carbon nanotube, octaazaporphyrin, and the like, a perfluoro compound obtained by substituting a hydrogen atom of the p-type organic semiconductor material described above with a fluorine atom (for example, perfluoropentacene, perfluorophthalocyanine, or the like), and a polymer compound containing an aromatic carboxylic acid anhydride or an imide compound thereof such as naphthalenetetracarboxylic anhydride, naphthalenetetracarboxylic diimide, perylenetetracarboxylic anhydride, and perylenetetracarboxylic diimide as a skeleton.

Among these, fullerene, a carbon nanotube, or a derivative thereof is preferably used from the viewpoint that the charge separation with the p-type organic semiconductor material can be performed fast (to 50 fs) and efficiently. More specific examples thereof may include fullerene C60, fullerene C70, fullerene C76, fullerene C78, fullerene C84, fullerene C240, fullerene C540, a mixed fullerene, a fullerene nanotube, a multi-walled carbon nanotube, a single-walled carbon nanotube, a carbon nanohorn (conical), and a fullerene derivative obtained by substituting a part thereof with a hydrogen atom, a halogen atom (a fluorine atom, a chlorine atom, a bromine atom, an iodine atom), or an alkyl group, an alkenyl group, an alkynyl group, an aryl group, a heteroaryl group, a cycloalkyl group, a silyl group, an ether group, a thioether group, or an amino group which is substituted or unsubstituted.

Particularly, it is preferable to use a fullerene derivative exhibiting solubility improved by a substituent such as [6,6]-phenyl C61-butyric acid methyl ester (abbreviated to PCBM or PC61BM), [6,6]-phenyl C61-butyric acid-n-butyl ester (PCBnB), [6,6]-phenyl C61-butyric acid-isobutyl ester (PCBiB), [6,6]-phenyl C61-butyric acid n-hexyl ester (PCBH), [6,6]-phenyl C71-butyric acid methyl ester (abbreviated to PC71BM), bis-PCBM described in Adv. Mater., Vol. 20 (2008), p 2116, an aminated fullerene described in Japanese Patent Application Laid-Open No. 2006-199674, a fullerene-derived metallocene described in Japanese Patent Application Laid-Open No. 2008-130889, or a fullerene having a cyclic ether group described in the specification of U.S. Pat. No. 7,329,709. Meanwhile, in the present embodiment, one kind of the n-type organic semiconductor material may be used singly or two or more kinds thereof may be used concurrently.

The junction form of the p-type organic semiconductor and the n-type organic semiconductor in the photoelectric conversion layer of the present embodiment is not particularly limited and may be a planar heterojunction or a bulk heterojunction. A planar heterojunction is a junction form in which a p-type organic semiconductor layer containing a p-type organic semiconductor and an n-type organic semiconductor layer containing an n-type organic semiconductor are laminated and the surface where the two layers are brought into contact with each other becomes a pn junction interface. On the other hand, the bulk heterojunction is formed by coating a mixture of a p-type organic semiconductor and an n-type organic semiconductor and the domain of the p-type organic semiconductor and the domain of the n-type organic semiconductor take a microphase-separated structure in this single layer. Hence, a large number of pn junction interfaces are present over the entire layer in the bulk heterojunction compared to the planar heterojunction. Consequently, a large number of excitons generated by light absorption can reach the pn junction interface and thus the efficiency leading to charge separation can be enhanced. For this reason, the junction of the p-type organic semiconductor and the n-type organic semiconductor in the photoelectric conversion layer of the present embodiment is preferably a bulk heterojunction.

In the present invention, the mixing ratio of the p-type organic semiconductor material to the n-type organic semiconductor material contained in the photoelectric conversion layer is preferably in the range of from 2:8 to 8:2 and more preferably in the range of from 3:7 to 7:3 in a mass ratio. In addition, the film thickness of the photoelectric conversion layer is preferably from 50 to 400 nm and more preferably from 80 to 300 nm.

In addition, an inorganic p-type semiconductor material and an inorganic n-type semiconductor material may be contained if necessary.

[Substrate]

The organic photoelectric conversion element of the present invention may include a substrate if necessary.

In a case in which the light to be photoelectrically converted is incident from the substrate side, the substrate is preferably a member capable of transmitting the light to be photoelectrically converted, that is, transparent with respect to the wavelength of the light to be photoelectrically converted. Suitable examples of the substrate may include a glass substrate or a transparent resin substrate. It is desirable to use a transparent resin film from the viewpoint of lightness and flexibility. In addition, it is desirable to use a glass substrate from the viewpoint of gas barrier property and light transmittance.

There is no particular limitation on the transparent resin film which can be preferably used as the transparent substrate in the present invention. The material, shape, structure, and thickness thereof can be appropriately selected from those known. Examples of the transparent resin film may include a polyester resin film such as polyethylene terephthalate (PET) and polyethylene naphthalate (PEN) modified polyester, a polyethylene (PE) resin film, a polypropylene (PP) resin film, a polystyrene resin film, a polyolefin resin film such as a cyclic olefin-based resin, a vinyl resin film such as polyvinyl chloride and polyvinylidene chloride, a polyetheretherketone (PEEK) resin film, a polysulfone (PSF) resin film, a polyether sulfone (PES) resin film, a polycarbonate (PC) resin film, a polyamide resin film, a polyimide resin film, an acrylic resin film, and a triacetyl cellulose (TAC) resin film, but a resin film having a transmittance of 80% or more at a wavelength in the visible light region (380 to 800 nm) can be preferably applied to the transparent resin film according to the present invention. Among them, a biaxially oriented polyethylene terephthalate film, a biaxially oriented polyethylene naphthalate film, a polyether sulfone film, and a polycarbonate film are preferable and a biaxially oriented polyethylene terephthalate film and a biaxially oriented polyethylene naphthalate film are more preferable in terms of transparency, heat resistance, ease of handling, strength, and cost.

The glass substrate is not particularly limited and may be an alkali-containing glass substrate such as soda glass, but a non-alkali glass is preferable. The sodium in the glass substrate is diffused into the electronic element in the case of using a non-alkali glass, and thus it is possible to prevent the properties of the electronic element from being deteriorated. It is preferable to form a sodium diffusion barrier layer on the glass substrate to prevent the diffusion of sodium atom in the case of using an alkali-containing glass substrate such as soda glass.

The transparent substrate used in the present invention can be subjected to a surface treatment or provided with an easy adhesion layer in order to secure the wettability and adhesive property of the coating solution. A technique known in the related art can be used for the surface treatment or the easy adhesion layer. Examples of the surface treatment may include a surface activation treatment such as a corona discharge treatment, a flame treatment, an ultraviolet treatment, a high frequency treatment, a glow discharge treatment, an active plasma treatment, and a laser treatment. In addition, examples of the easy adhesion layer may include a polyester, a polyamide, a polyurethane, a vinyl copolymer, a butadiene copolymer, an acrylic copolymer, a vinylidene copolymer, and an epoxy-based copolymer.

In addition, a barrier coat layer may be formed in advance on the transparent substrate or a hard coat layer may be formed in advance on the side opposite to the side on which a transparent conductive layer is transferred for the purpose of suppressing the permeation of oxygen and moisture vapor.

(Other Layers)

The organic photoelectric conversion element of the present embodiment may be further provided with other members (other layers) in addition to the respective members (respective layers) described above in order to improve the photoelectric conversion efficiency and the life span of the element. Examples of the other members may include a hole injection layer, an electron injection layer, an exciton blocking layer, a UV absorbing layer, a light-reflecting layer, and a wavelength conversion layer. In addition, a layer of a silane coupling agent or the like may be provided in order to more stabilize the metal oxide fine particles localized in the upper layer or the like. Moreover, a metal oxide layer may be laminated to be adjacent to the photoelectric conversion layer of the present invention.

In addition, the organic photoelectric conversion element of the present invention may have various kinds of optical functional layers for the purpose of more efficiently receiving sunlight. Examples of the optical functional layer may include an antireflective film, a light-collecting layer such as a microlens array, a light diffusing layer by which the light reflected by the anode can be scattered and incident to the power generation layer again.

As the antireflection layer, it is possible to provide various kinds of known antireflection layers, but it is more preferable to set the refractive index of the easy adhesion layer adjacent to the film to be from 1.57 to 1.63 since the interfacial reflection between the film substrate and the easy adhesion layer decreases and thus the transmittance can be improved, for example, in a case in which the transparent resin film is a biaxially oriented polyethylene terephthalate film. The adjustment of the refractive index can be performed by appropriately adjusting the ratio of the oxide sol having a relatively high refractive index such as tin oxide sol or cerium oxide sol to the binder resin and then coating. The easy adhesion layer may be a single layer, but may be constituted by two or more layers in order to improve the adhesive property.

As the light-collecting layer, for example, the support substrate may be processed so as to be provided with a structure of microlens array on the sunlight receiving side or the so-called light-collecting sheet may be combined, hence, it is possible to increase the quantity of light received from a particular direction or to reduce the incident angle dependence of sunlight in contrast.

As an example of the microlens array, a quadrangular pyramid is two-dimensionally arranged on the light extraction side of the substrate so as to have a side length of 30 μm and an apex angle of 90 degrees. The length of a side is preferably from 10 to 100 μm. The microlens array is colored since a diffraction effect occurs when the side length is shorter than this and the thickness thereof is thick when the side length is too long, therefore it is not preferable.

In addition, examples of the light scattering layer may include various kinds of anti-glare layers and a layer obtained by dispersing a nanoparticle, a nanowire, or the like of a metal, various kinds of inorganic oxides, or the like in a colorless transparent polymer.

[Method of Manufacturing Organic Photoelectric Conversion Element]

(Film Forming Method and Surface Treatment Method)

As the method of forming the photoelectric conversion layer containing a p-type organic semiconductor material and an n-type organic semiconductor material, the intermediate layer, and the electrode, a deposition method, a coating method (including a casting method and a spin coating method), and the like can be exemplified. Among these, as the method of forming the photoelectric conversion layer, a deposition method, a coating method (including a casting method and a spin coating method), and the like can be exemplified. Among these, a coating method is preferable in order to increase the interfacial area where a hole and an electron are charge-separated and to produce an element having high photoelectric conversion efficiency. Moreover, a coating method is also excellent in the production rate. In addition, a coating method is preferable as the method of forming the intermediate layer. A coating method is also excellent in the production rate.

The coating method used at this time is not limited, and examples thereof may include a spin coating method, a method of casting from a solution, a dip coating method, a blade coating method, a wire bar coating method, a gravure coating method, and a spray coating method. Moreover, it can also be patterned by a printing method such as an inkjet method, a screen printing method, a relief printing method, an intaglio printing method, an offset printing method, or a flexographic printing method.

After coating, heating is preferably performed in order to remove the residual solvent, moisture, and gas, to improve the mobility by crystallization of the semiconductor material, and to cause the expansion of the absorption wavelength. The aggregation or crystallization of a part of the photoelectric conversion layer is microscopically promoted and thus a suitably phase-separated structure can be obtained when the annealing treatment at a predetermined temperature is performed during the manufacturing process. As a result, the carrier mobility of the photoelectric conversion layer is improved and thus high efficiency can be obtained.

The photoelectric conversion layer may be constituted as a layer in which a p-type semiconductor and an n-type semiconductor are mixed, but may be a plural-layer having different mixing ratios thereof in a film thickness direction, or may have a gradation constitution in the mixing ratio.

(Patterning)

In the organic photoelectric conversion element according to the present invention, the electrode or the photoelectric conversion layer, a hole transport layer, an electron transport layer, and the like may be patterned if necessary. The technique of patterning these layers is not particularly limited and a known technique can be appropriately applied. For example, in the case of an insoluble material such as the photoelectric conversion layer and the transport layer, the entire surface is coated by die coating, dip coating, or the like and then only an unnecessary portion may be wiped off, or patterning may be directly performed at the time of coating using a method such as an inkjet method or a screen printing method. On the other hand, in the case of an insoluble material such as the electrode material, it is possible to perform the mask deposition at the time of performing the vacuum deposition of the electrode or to pattern by a known method such as etching or lift-off. In addition, a pattern may be formed by transferring a pattern formed on a separate substrate.

(Sealing)

It is preferable to seal not only the organic photoelectric conversion element but also the organic electroluminescence element or the like by a known technique in order to prevent the deterioration of the organic photoelectric conversion element manufactured, by oxygen, moisture, or the like in the environment. Examples of the technique may include a technique of sealing by attaching a cap fabricated by aluminum or glass with an adhesive, a technique of sticking a plastic film having a gas barrier layer of aluminum, silicon oxide, aluminum oxide or the like formed thereon on the organic photoelectric conversion element with an adhesive, a method of spin coating an organic polymer material exhibiting high gas barrier property (polyvinyl alcohol or the like), a method of piling an inorganic thin film exhibiting high gas barrier property (silicon oxide, aluminum oxide, or the like) or an organic film (Parylene or the like) under vacuum, and a method of laminating these layers by combining these methods.

<Organic Photoelectric Conversion Element According to Another Embodiment>

The transparent conductive film according to the present invention is not only applied as the transparent electrode of the heterojunction type organic photoelectric conversion element described above having a photoelectric conversion layer constituted to contain a p-type organic semiconductor material and an n-type organic semiconductor material, but may also be applied as the transparent electrode of a dye-sensitized type photoelectric conversion element. For example, the transparent conductive film according to the present invention may be used as a first electrode 1 or a second electrode 8 as illustrated in FIG. 1 of Japanese Patent Application Laid-Open No. 2012-023266.

[Application of Organic Photoelectric Conversion Element]

According to another aspect of the present invention, a solar cell having the organic photoelectric conversion element according to the present invention is provided. The organic photoelectric conversion element of the present embodiment has excellent photoelectric conversion efficiency and durability (heat resistance, light resistance) and thus may be suitably used in a solar cell adopting this as the power generation element. In particular, by using the transparent conductive film according to the present invention in at least one or both of the first electrode and the second electrode constituting the organic photoelectric conversion element, both the two electrodes can be a transparent electrode, by virtue of this, it is possible to obtain a semi-transparent type (see-through type) solar cell.

In addition, according to still another aspect of the present invention, an optical sensor array is provided in which the organic photoelectric conversion element described above is arranged in an array shape. In other words, the organic photoelectric conversion element of the present aspect can also be used as an optical sensor array to convert an image projected onto the optical sensor array into an electrical signal utilizing the photoelectric conversion function thereof.

EXAMPLES

Hereinafter, the present invention will be specifically explained with reference to Examples, but the present invention is not limited thereto. Meanwhile, the units "part" and "%" used in Examples represent "part by mass" and "% by mass" unless otherwise specified.

Meanwhile, in the following Examples, the evaluation of the refractive index of the protective layer was performed by the following method.

<Evaluation Method of Refractive Index>

A sample provided with only a protective layer was prepared by coating according to the following method. First, a non-alkali glass as the substrate was washed in order of the ultrasonic cleaning with CLEANTHROUGH KS3030 manufactured by Kao Corporation as a surfactant and ultra-pure water and the ultrasonic cleaning with ultrapure water, and then dried by nitrogen blowing, and finally subjected to the ultraviolet ozone cleaning. Subsequently, a protective layer (thickness: 20 nm) used in each Example was formed on the substrate. At this time, the formation of the protective layer was performed in the same manner as described in Examples below.

After the roughening treatment of the back surface of the measurement side of the sample obtained above, the light absorption treatment of each sample was performed with a black spray so as to prevent the reflection of light at the back surface, and the refractive index was determined from the measurement result of the reflectance in the visible light region (400 nm to 700 nm) using a reflectance spectral film thickness meter FE-3000 (manufactured by OTSUKA ELECTRONICS CO., LTD.).

Preparation Example 1: Synthesis of Exemplified Compound 1

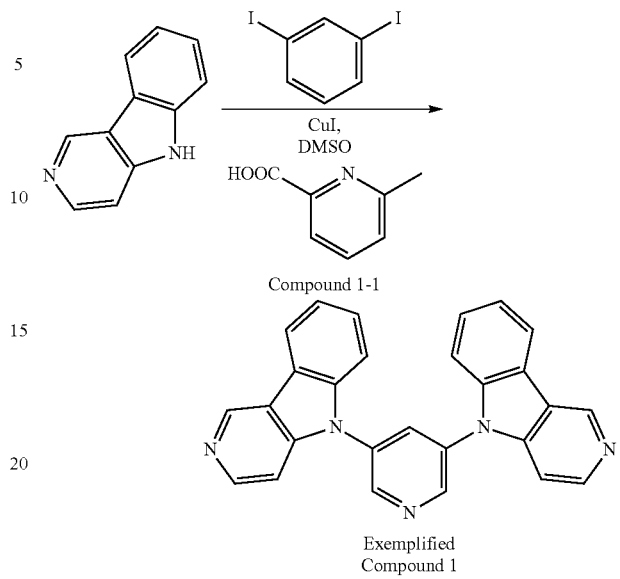

Exemplified Compound 1 above was synthesized by referring to Japanese Patent Application Laid-Open No. 2010-235575.

Under a stream of nitrogen, 460 mg (1.4 mmol) of 1,3-diiodobenzene (manufactured by Sigma-Aldrich Co. LLC.) and 470 mg (2.8 mmol) of Exemplified Compound 1-1 (synthesized by referring to Japanese Patent Application Laid-Open No. 2010-235575) were added to 15 ml of DMSO and 0.89 g (4.2 mmol) of potassium phosphate and stirred for 10 minutes. To the resultant, 53 mg (0.28 mmol) of CuI and 6-methyl picolinic acid (0.56 mmol) were added and heated at 125° C. for 7 hours. Under cooling with water, 5 ml of water was added thereto and stirred for 1 hour. The precipitated crude product was filtered, further subjected to the column purification, and then recrystallized with o-dichlorobenzene/acetonitrile so as to obtain 470 mg (yield of 82%) of Exemplified Compound 1.

Preparation Example 2: Synthesis of Exemplified Compound 10

Exemplified Compound 10 above was synthesized by referring to Japanese Patent Application Laid-Open No. 2008-69122.

Preparation Example 3: Synthesis of Exemplified Compound 13

The following Exemplified Compound 13 was synthesized by referring to paragraphs [0038] to [0040] of Japanese Patent Application Laid-Open No. 2010-235575.

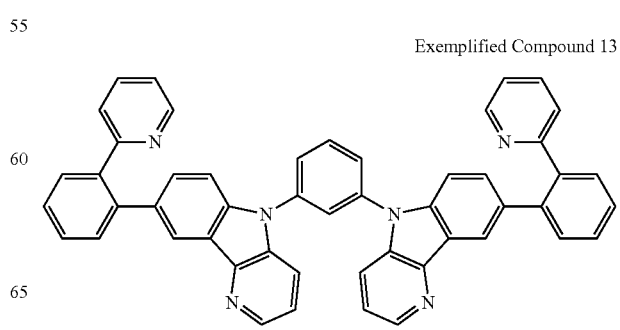

Preparation Example 4: Synthesis of Exemplified Compound 18

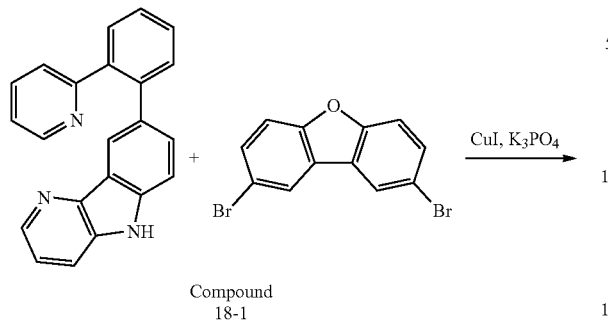

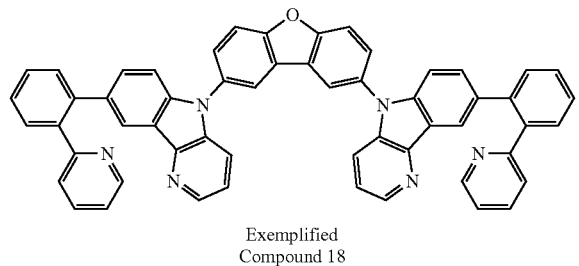

Exemplified Compound 18

Exemplified Compound 18 was synthesized by referring to Japanese Patent Application Laid-Open No. 2010-235575.

Under a stream of nitrogen, 0.46 g (1.4 mmol) of 2,8-dibromodibenzofuran (manufactured by Sigma-Aldrich Co. LLC.) and 0.90 g (2.8 mmol) of Exemplified Compound 18-1 were added to 15 ml of DMSO and 0.89 g (4.2 mmol) of potassium phosphate and stirred for 10 minutes. To the resultant, 53 mg (0.28 mmol) of CuI and 6-methyl picolinic acid (0.56 mmol) were added and heated at 125° C. for 7 hours. Under cooling with water, 5 ml of water was added thereto and stirred for 1 hour. The precipitated crude product was filtered, further subjected to the column purification, and then recrystallized with o-dichlorobenzene/acetonitrile so as to obtain 0.80 g (yield of 71%) of Exemplified Compound 18.

Preparation Example 5: Synthesis of Exemplified Compound 20

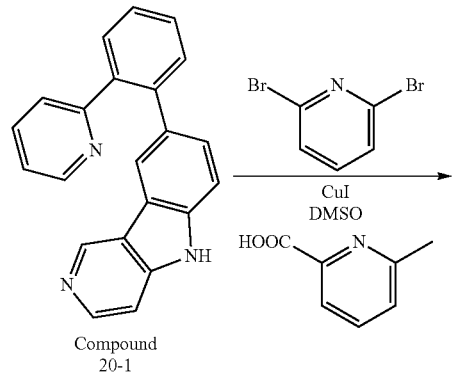

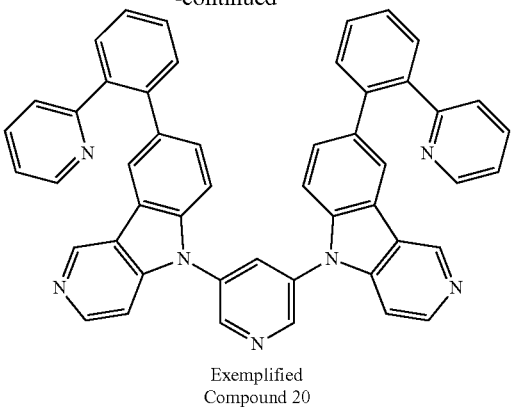

Exemplified Compound 20

Exemplified Compound 20 was synthesized by referring to Japanese Patent Application Laid-Open No. 2010-235575.

Under a stream of nitrogen, 0.33 g (1.4 mmol) of 2,6-dibromopyridine (manufactured by Sigma-Aldrich Co. LLC.) and 0.90 g (2.8 mmol) of Exemplified Compound 20-1 (synthesized by referring to Japanese Patent Application Laid-Open No. 2010-235575) were added to 15 ml of DMSO and 0.89 g (4.2 mmol) of potassium phosphate and stirred for 10 minutes. To the resultant, 53 mg (0.28 mmol) of CuI and 6-methyl picolinic acid (0.56 mmol) were added and heated at about 125° C. for 7 hours. Under cooling with water, 5 ml of water was added thereto and stirred for 1 hour. The precipitated crude product was filtered, further subjected to the column purification, and then recrystallized with o-dichlorobenzene/acetonitrile so as to obtain 0.75 g (yield of 75%) of Exemplified Compound 20.

Preparation Example 6: Synthesis of Exemplified Compound 31

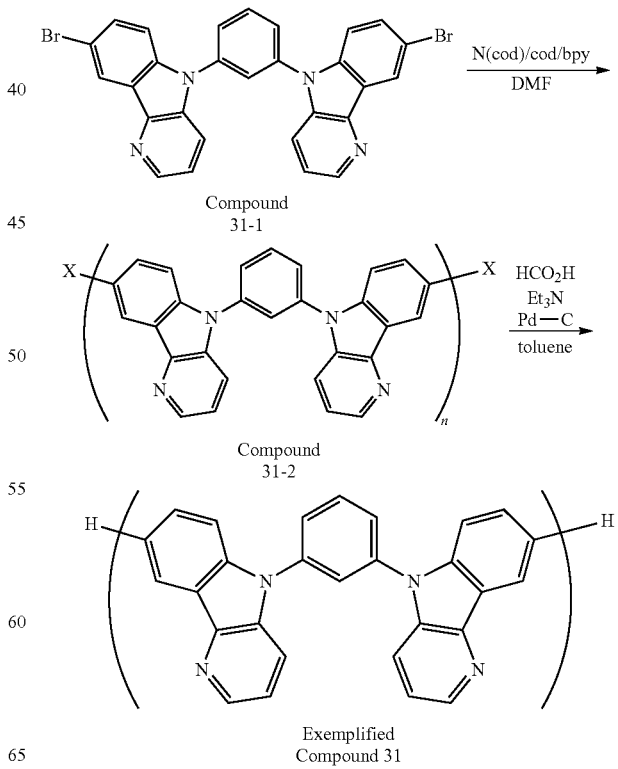

Exemplified Compound 31

Under a stream of nitrogen, Compound 31-1 (1.0 mol), Ni(cod)₂ (1.2 mol), 1,5-cyclooctadiene (1 ml), and bipyridine (1 mol) were dissolved in 200 ml of DMF and stirred at 90° C. for 18 hours. After the reaction, the reaction solution was poured into 400 ml of hydrochloric methanol to purify, and then the precipitate was collected by filtration. The precipitate thus obtained was washed with hydrochloric methanol, ethanol, hot toluene, a hot aqueous solution of ethylenediaminetetraacetic acid, sodium bicarbonate water, distilled water in this order so as to obtain Compound 31-2 in a yield of 50%.

Under the atmosphere, 150 mg of the intermediate, 0.18 ml of formic acid, 0.68 ml of ethylenediamine, and 180 mg of Pd/C were dissolved in 20 ml of toluene and stirred at 90° C. for 4 hours. Thereafter, Pd/C was filtered out, and the filtrate was distilled under reduced pressure so as to be concentrated. The solid thus obtained was washed with sodium bicarbonate water, water, and methanol in this order so as to obtain Exemplified Compound 31 in a yield of 75%.

Preparation Example 7: Synthesis of Exemplified Compound 41

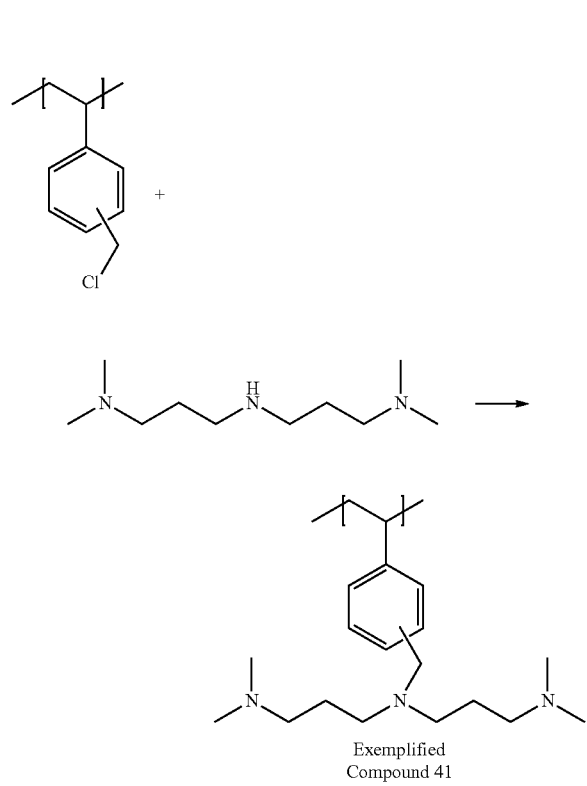

Exemplified Compound 41

In a mixed solvent of 100 ml of tetrahydrofuran and 100 ml of N,N-dimethylformamide, 1.0 g of a 60/40 mixture of 3- and 4-isomers (number average molecular weight of 55000) of poly(vinylbenzyl chloride) (manufactured by Sigma-Aldrich Co. LLC.) and 9.0 g of 3,3'-iminobis(N,N-dimethylpropylamine) (manufactured by Sigma-Aldrich Co. LLC.) were dissolved and stirred at room temperature (25° C.) for 48 hours to perform the reaction. After the reaction was completed, the solvent was removed by distillation under reduced pressure, and the reprecipitation was further performed in water so as to obtain 1.8 g of Exemplified Compound 41 (yield of 95%).

Preparation Example 8: Synthesis of Exemplified Compound 46

Exemplified Compound 46 was synthesized by the following reaction.

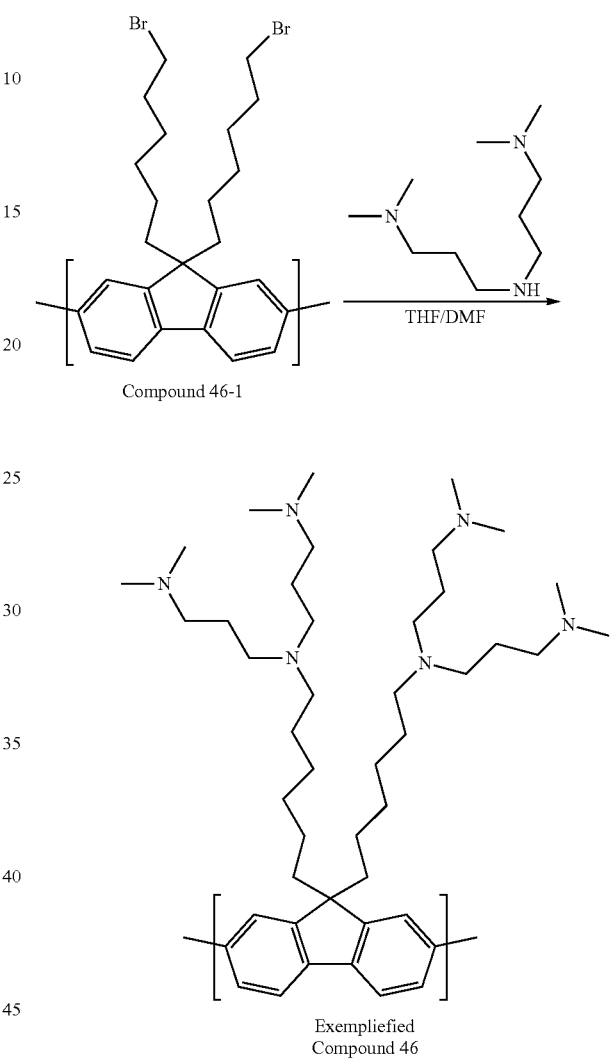

Compound 46-1 was synthesized by referring to Adv. Mater. 2007, 19, 2010. The weight average molecular weight of Compound 46-1 was 4400. In a mixed solvent of 100 ml of tetrahydrofuran and 100 ml of N,N-dimethylformamide, 1.0 g of this Compound 46-1 and 9.0 g of 3,3'-iminobis(N,N-dimethylpropylamine) (manufactured by Sigma-Aldrich Co. LLC.) were dissolved and stirred at room temperature (25° C.) for 48 hours to perform the reaction. After the reaction was completed, the solvent was removed by distillation under reduced pressure, and the reprecipitation was further performed in water so as to obtain 1.3 g of Exemplified Compound 46 (yield of 90%). The structure of the compound thus obtained was identified by H-NMR. The result is presented below. 7.6 to 8.0 ppm (br), 2.88 ppm (br), 2.18 ppm (m), 2.08 ppm (s), 1.50 ppm (m), and 1.05 ppm (br).

Preparation Example 9: Synthesis of Exemplified Compound 52

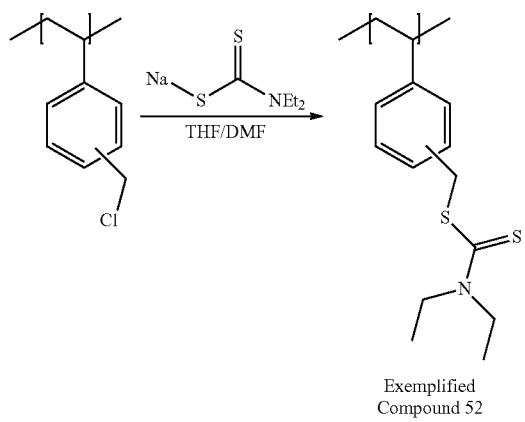

Exemplified Compound 52

Exemplified Compound 52 was synthesized by referring to Macromolecules 2003, vol. 36, p 3505.

In a mixed solvent of 100 ml of tetrahydrofuran and 100 ml of N,N-dimethylformamide, 1.0 g of a 60/40 mixture of 3- and 4-isomers (number average molecular weight of 55000) of poly(vinylbenzyl chloride) (manufactured by Sigma-Aldrich Co. LLC.) and 1.77 g of N,N-diethyldithiocarbamate trihydrate were dissolved and stirred at 40° C. for 48 hours to perform the reaction. After the reaction was completed, the precipitated sodium chloride was filtered out, and the reprecipitation was further performed in water so as to obtain 1.3 g of Exemplified Compound 52 (yield of 83%).

Preparation Example 10: Synthesis of Exemplified Compound 54

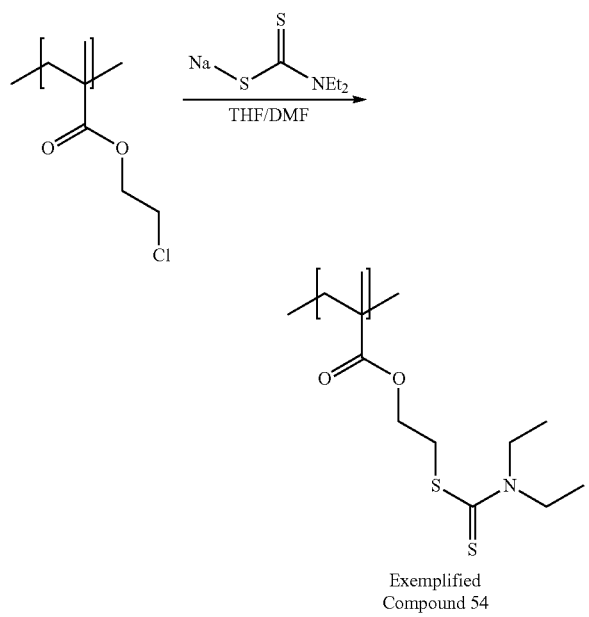

Exemplified Compound 54

Exemplified Compound 54 was synthesized by referring to Macromolecules 2003, vol. 36, p 3505.

In a mixed solvent of 100 ml of tetrahydrofuran and 100 ml of N,N-dimethylformamide, 1.0 g of poly(chloroethyl methacrylate) and 1.8 g of N,N-diethyldithiocarbamate trihydrate were dissolved and stirred at 40° C. for 48 hours to perform the reaction. After the reaction was completed, the precipitated sodium chloride was filtered out, and the reprecipitation was further performed in water so as to obtain 1.25 g of Exemplified Compound 54 (yield of 80%).

Preparation Example 11: Synthesis of Exemplified Compound 57

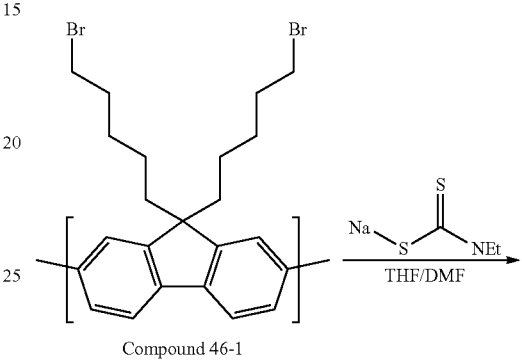

Compound 46-1

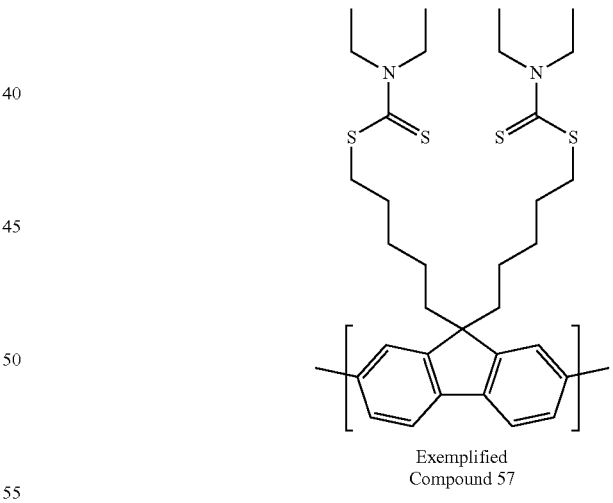

Exemplified Compound 57

Exemplified Compound 57 was synthesized by referring to Macromolecules 2003, vol. 36, p 3505.

In a mixed solvent of 100 ml of tetrahydrofuran and 100 ml of N,N-dimethylformamide, 1.0 g of Compound 46-1 and 0.60 g of N,N-diethyldithiocarbamate trihydrate were dissolved and stirred at 40° C. for 48 hours to perform the reaction. After the reaction was completed, the precipitated sodium chloride was filtered out, and the reprecipitation was further performed in water so as to obtain 1.1 g of Exemplified Compound 57 (yield of 85%).

Preparation Example 12: Synthesis of Exemplified Compound 74

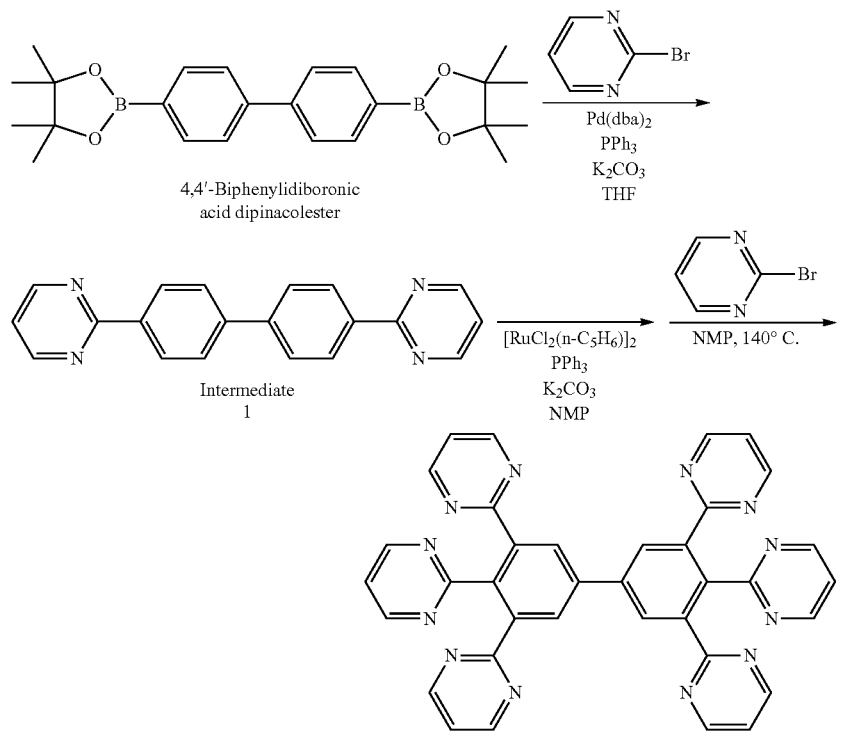

Into a 300 ml round-bottomed flask, a THF solution (200 ml) containing 4,4'-biphenyldiboronic acid dipinacolester (10 g, 0.025 mol), 2-bromopyrimidine (2.5 eq.), Pd(dba)$_2$ (0.2 eq.), PPh$_3$ (0.4 eq.) and K$_2$CO$_3$ (2 eq.) was introduced and refluxed at 80° C. for 10 hours under a nitrogen atmosphere.

Thereafter, the resultant was cooled to room temperature, and then the solution was transferred to a separatory funnel to perform the extraction. Ethyl acetate and saturated saline solution were added to the solution and the solution was separated into an organic phase and an aqueous phase, thereafter, the organic phase was taken out therefrom and distilled off under reduced pressure. The solid thus obtained was purified by silica gel column chromatography so as to obtain a white solid (9.3 g, yield of 82%) of Compound 74-1.

Subsequently, the 300 ml round-bottomed flask was subjected to the nitrogen purge five times under reduced pressure. To this, a dehydrated and degassed NMP (1-methyl-2-pyrrolidone) solution (150 ml) of Compound 74-1 (7.5 g, 0.024 mol), K$_2$CO$_3$ (12 eq.), PPh$_3$ (0.4 eq.) and [RuCl$_2$(η-C$_6$H$_6$)]$_2$ (0.1 eq.) was added and stirred at 140° C. under a nitrogen atmosphere.

Subsequently, a dehydrated and degassed NMP solution (150 ml) of 2-bromopyrimidine (8 eq.) was added to the reaction flask dropwise over 10 hours. After the dropwise addition of the solution was completed, the resultant was stirred at 140° C. for 3 hours.

Thereafter, the resultant was cooled to room temperature, and then 600 ml of pure water was added thereto and the precipitate thus formed was filtered. The precipitate was dissolved in 350 ml of THF, and then the resultant solution was dried over sodium sulfate and distilled off under reduced pressure. The solid thus obtained was purified by silica gel column chromatography so as to obtain a white solid (3.8 g, yield of 25%) of Exemplified Compound 74.

Meanwhile, the synthesis method described above can be carried out by referring to, for example, the method disclosed in Oi, S.; Fukita, S.; Hirata, N.; Watanuki, N.; Miyano, S.; Inoue, Y., Org. Lett., 2001, 3, 2579.

Preparation Example 13: Synthesis of Exemplified Compound 68

[Chem. 41]

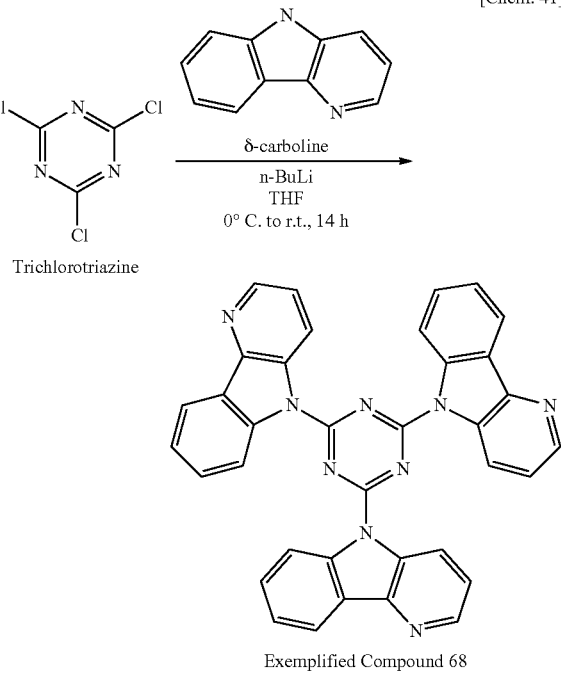

A THF solution (50 ml) of δ-carboline (5.5 g, 33 mmol) in a 100 ml round-bottomed flask was stirred at 0° C. for 1 hour under a nitrogen atmosphere. Thereafter, a 1.6M n-BuLi hexane solution (25 ml, 1.2 eq.) was gradually added thereto dropwise and then stirred until the temperature thereof reached room temperature.

A THF solution (100 ml) of trichlorotriazine (1.0 g, 4.5 mmol) in a 200 ml round-bottomed flask was stirred at room temperature under a nitrogen atmosphere, and the n-BuLi solution of δ-carboline from the 100 ml round-bottomed flask was gradually added to this solution dropwise and stirred at room temperature for 14 hours.

Thereafter, the solution was transferred to a separatory funnel to perform the extraction. Ethyl acetate and saturated saline solution were added to the solution and the solution was separated into an organic phase and an aqueous phase, thereafter, the organic phase was taken out therefrom and distilled off under reduced pressure. The solid thus obtained was purified by silica gel column chromatography so as to obtain a white solid (1.86 g, yield of 71%) of Exemplified Compound (68).

Preparation Example 14: Synthesis of Exemplified Compound 79 after the resultant was dissolved in 60 ml of ethyl acetate, and 130 ml of hexane was gradually added thereto. The precipitated crystal was collected by filtration and dissolved in a methanol/THF mixture, and then the resultant was subjected to flash column and then the solvent was removed. The resultant was heated and refluxed in acetonitrile/methanol, and then the crystal was collected by filtration and dried so as to obtain 13 g of Exemplified Compound 79 (yield of 74%).

Meanwhile, the synthesis method described above can be carried out by referring to, for example, the method disclosed in Japanese Patent Application Laid-Open No. 2008-69122.

<<<Fabrication of Transparent Conductive Film>>>
[Fabrication of Transparent Conductive Films 1 to 25]
(Preparation of Substrate)

A non-alkali glass as the substrate was washed in order of the ultrasonic cleaning with CLEANTHROUGH KS3030 manufactured by Kao Corporation as a surfactant and ultrapure water and the ultrasonic cleaning with ultrapure water, and then dried by nitrogen blowing, and finally subjected to the ultraviolet ozone cleaning.

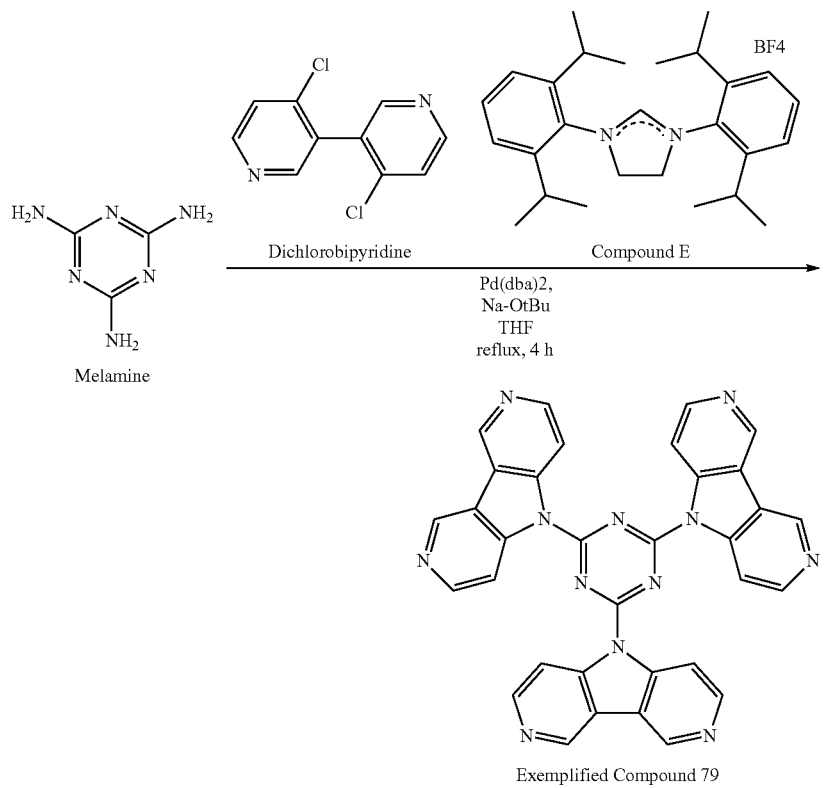

Exemplified Compound 79

Under a nitrogen atmosphere, 2.1 g of Pd(dba)2, 1.7 g of Compound E, and 40 ml of ethylene glycol dimethyl ether were mixed and stirred at about 40° C. for 20 minutes. To this liquid mixture, 27 g (120 mmol) of dichlorobipyridine (synthesized by referring to Japanese Patent Application Laid-Open No. 2008-69123), 3.8 g (30 mmol) of melamine, 30 g of sodium-t-butoxide, and 350 ml of ethylene glycol dimethyl ether were mixed and then heated and refluxed for 4 hours. After the insoluble matter was removed, THF was extracted and washed with water. Subsequently, the solvent was removed by distillation under reduced pressure, there- (Formation of Ground Layer)

Subsequently, the compounds presented in Table 1 and a comparative compound (calcium acetylacetonate [Ca(acac)$_2$], Au, αNPD, or TmPyPB) were respectively dissolved in a mixed solvent of n-butanol:hexafluoroisopropanol=1:1 (volume ratio) so as to be 0.02% by mass, thereby preparing a solution. This solution was coated on the substrate having a temperature adjusted at 65° C. using a blade coater at a coating speed of 10 mm/s, and was subjected to the heat treatment for 2 minutes on a hot plate at 100° C. so as to obtain a ground layer having a dry film thickness of about 5 nm.

Meanwhile, in the transparent conductive film 1, a metal thin film layer was directly formed on the substrate without forming a ground layer.

In addition, in the transparent conductive film 2, a ground layer consisting of gold (Au) was formed by a deposition method under the same conditions as in the following metal thin film layer.

Meanwhile, calcium acetylacetonate (Ca(acac)$_2$) used as a comparative compound was a commercially available product manufactured by Wako Pure Chemical Industries, Ltd. In addition, each of αNPD and TmPyPB is a compound having the following structure.

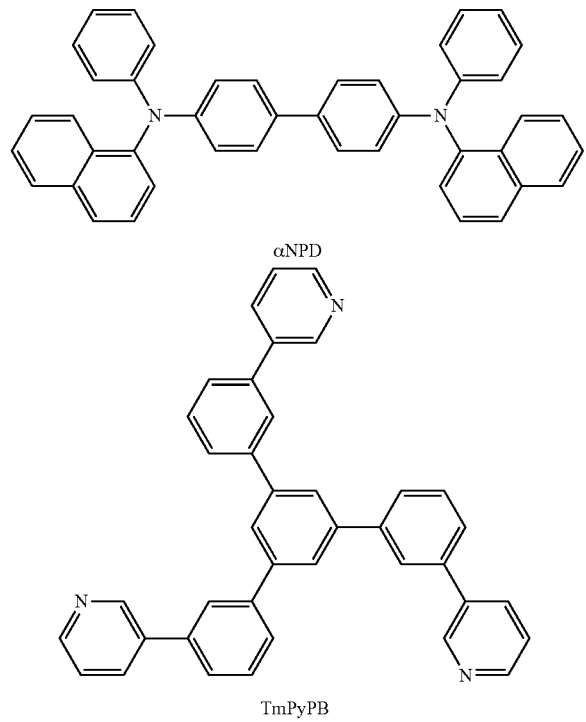

αNPD

TmPyPB (Formation of Metal Thin Film Layer)

Next, the substrate having the above ground layer formed thereon was installed in a vacuum deposition apparatus, the internal pressure of the vacuum deposition apparatus was reduced to $10^{-3}$ Pa or less, and then the electrode materials presented in Table 1 were respectively deposited on the ground layer at a deposition rate of 2 nm/sec according to the film thickness presented in Table 1 so as to form a metal thin film layer.

<Evaluation of Conductivity of Transparent Conductive Film>

The sheet resistance value was measured with regard to each of the transparent electrodes of sample Nos. 1 to 25 fabricated above. The measurement of the sheet resistance value was performed by a 4-terminal 4-probe statutory current application method using a resistivity meter (MCP-T610 manufactured by Mitsubishi Chemical Corporation).

(Formation of Protective Layer)

Next, a protective layer consisting of the Parylene HT (refractive index of 1.55) was formed at 20 nm on the transparent electrode above using PDS2010 manufactured by Specialty Coating Systems, Inc.

<Evaluation of Transmittance of Transparent Conductive Film>

The light transmittance was measured with regard to each of the transparent electrodes of sample Nos. 1 to 25 fabricated above after the protective layer was formed. The measurement of light transmittance was performed using a spectrophotometer (U-3300 manufactured by Hitachi Ltd.) and the same substrate as that of the sample for a baseline.

Meanwhile, the transmittance is measured after the formation of the protective layer in order to use a material equivalent to the constitution of an actual organic thin film solar cell and to enable the influence of reflection at the outermost layer (metal thin film) to be reduced.

The results obtained above are presented in Table 1.

From Table 1, it can be seen that the transparent conductive film, formed by laminating a ground layer formed using the nitrogen-containing organic compound according to the present invention and a metal thin film layer which contains a metal element of Group 11 of the periodic table and has a thickness of from 2 to 10 nm, is equipped with both high transmittance and conductivity. Meanwhile, it can be seen that a more preferable transparent conductive film can be obtained as a ground layer contains a larger number of nitrogen when the organic photoelectric conversion elements 6 to 13 are compared to one another.

<<<Fabrication of Forwardly Layered Bulk Heterojunction Type Organic Photoelectric Conversion Element>>>

[Fabrication of Organic Photoelectric Conversion Elements 1 to 25 (Using Transparent Conductive Film as Second Electrode)]

(Formation of Transparent Electrode)

A first electrode was formed by piling an indium tin oxide (ITO) transparent conductive film on a non-alkali glass substrate at 150 nm (sheet resistance 12 Ω/square) and patterning at a width of 10 mm using a common photolithography technology and wet etching. The patterned first electrode was washed in order of the ultrasonic cleaning with a surfactant and ultrapure water and the ultrasonic cleaning with ultrapure water, and then dried by nitrogen blowing, and finally subjected to the ultraviolet ozone cleaning.

(Formation of Hole Transport Layer)

Subsequently, as a hole transport layer, an isopropanol solution containing PEDOT-PSS (CLEVIOS (registered trademark) P VP AI 4083 manufactured by Heraeus Materials Technology, conductivity of $1 \times 10^{-3}$ S/cm) consisting of a conductive polymer and a polyanion at 2.0% by mass was prepared and coated on the substrate having a temperature adjusted at 65° C. using a blade coater and dried so as to have a dry film thickness of about 30 nm. Thereafter, the resultant was heat treated for 20 seconds with hot air at 120° C., whereby a hole transport layer was formed on the first electrode above.

The substrate was then brought into a glove box and the following operations were performed under a nitrogen atmosphere.

First, the substrate was heat treated at 120° C. for 3 minutes under a nitrogen atmosphere.

(Formation of Photoelectric Conversion Layer)

Subsequently, an organic photoelectric conversion material composition solution was prepared by mixing 1.0% by mass of P3HT (Sepiolid P200 manufactured by BASF) as a p-type organic semiconductor material and 0.8% by mass of PC61BM (nanom spectra E100H manufactured by Frontier Carbon Corporation) as an n-type organic semiconductor material in o-dichlorobenzene and completely dissolved by stirring (for 60 minutes) while heating at 80° C. on a hot plate, and then the solution was coated on the substrate having a temperature adjusted at 80° C. using a blade coater so as to have a dry film thickness of about 170 nm and dried for 2 minutes, whereby a photoelectric conversion layer was formed on the hole transport layer above.

(Ground Layer of Second Electrode)

Subsequently, the compound and the comparative compound presented in Table 1 were respectively dissolved in a mixed solvent of n-butanol:hexafluoroisopropanol=1:1 (volume ratio) so as to be 0.02% by mass, thereby preparing a solution. This solution was coated on the substrate having a temperature adjusted at 65° C. using a blade coater and dried so as to have a dry film thickness of about 5 nm. Thereafter, the resultant was heat treated for 2 minutes with hot air at 100° C., whereby a ground layer was formed on the photoelectric conversion layer above.

(Formation of Second Electrode)

Next, the substrate having the above ground layer formed thereon was installed in a vacuum deposition apparatus. Then, the element was set such that the shadow mask with a 10 mm width was perpendicular to the transparent electrode, the internal pressure of the vacuum deposition apparatus was reduced to $10^{-3}$ Pa or less, and then the second electrode materials presented in Table 1 were respectively deposited at a deposition rate of 2 nm/sec according to the film thickness presented in Table 1 so as to form a metal thin film layer on the ground layer above.

(Formation of Protective Layer)

The organic photoelectric conversion element thus obtained was conveyed to PDS2010 manufactured by Specialty Coating Systems Inc. in a state of not contacting with the atmosphere, and a protective layer consisting of the Parylene HT (refractive index of 1.55) was formed at 20 nm.

(Sealing of Organic Photoelectric Conversion Element)

Moreover, the organic photoelectric conversion element was conveyed into a glove box and then interposed between two pieces of Ultra Barrier Solar Film UBL-9L manufactured by 3M (moisture vapor transmission rate of $<5\times10^{-4}$ g/m²/d), sealing thereof was performed using a UV curing resin (XNR5570-B1 UV RESIN manufactured by Nagase ChemTex Corporation), and then the resultant element was taken out under the atmosphere to fabricate organic photoelectric conversion elements 1 to 25 having a light receiving portion size of about 10×10 mm.

<Evaluation of Organic Photoelectric Conversion Element>

(Evaluation of Photoelectric Conversion Efficiency)

The photoelectric conversion element fabricated above was irradiated with light of a solar simulator (AM 1.5G filter) having an intensity of 100 mW/cm², a mask having an effective area of 1 cm² was superimposed on the light receiving portion, the short circuit current density $J_{sc}$ [mA/cm²], the open circuit voltage $V_{oc}$ [V], and the fill factor FF were measured with regard to each of the light receiving portions at four positions formed on the same element, and the average value thereof was determined. In addition, the photoelectric conversion efficiency η (%) was determined from the short circuit current density $J_{sc}$, the open circuit voltage $V_{oc}$, and the fill factor FF thus obtained according to Equation (1). Here, it indicates that the energy conversion efficiency (photoelectric conversion efficiency) is more favorable as the numerical value of the photoelectric conversion efficiency η (%) is greater.

$$\eta[\%]=J_{sc}\text{ [mA/cm}^2]\times V_{OC}\text{ [V]}\times\text{FF [\%]/Intensity of incident light [mW/cm}^2]\quad\text{Equation (1)}$$

(Evaluation of Durability of Photoelectric Conversion Efficiency)

While the organic photoelectric conversion element subjected to the evaluation of the photoelectric conversion efficiency above was connected to the resistance between the cathode and the anode, the organic photoelectric conversion element was heated at 80° C. and continuously exposed to the light of a solar simulator (AM 1.5G filter) having an intensity of 100 mW/cm for 1000 hours, and then the organic photoelectric conversion element was cooled to room temperature, and the photoelectric conversion efficiency η (%) was determined according to Equation (1) above with regard to each of the light receiving portions at four positions formed on the organic photoelectric conversion element in the same manner as in the evaluation of the photoelectric conversion efficiency above. Subsequently, the relative efficiency of the conversion efficiency was calculated by the following Equation (2) and the average value thereof was determined, and this was taken as a measure of the durability of the photoelectric conversion efficiency.

Relative efficiency of conversion efficiency (%)=
[(Conversion efficiency after exposure)/(Conversion efficiency before exposure)]×100    Equation (2)

Here, it indicates that the durability of the energy conversion efficiency (durability of the photoelectric conversion efficiency) is excellent as the relative efficiency of the conversion efficiency (%) is high. The time at which the falling rate of this relative efficiency was 80% was taken as LT80 and used for the evaluation of the durability of the element.

The results obtained above are presented in Table 1. From Table 1, it can be seen that the organic photoelectric conversion elements 6 to 25 of the present invention using the transparent conductive film formed by laminating a ground layer formed using the nitrogen-containing organic compound according to the present invention and a metal thin film layer which contains a metal element of Group 11 of the periodic table and has a thickness of from 2 to 10 nm as the anode (second electrode) is a see-through type organic thin film solar cell exhibiting high photoelectric conversion efficiency and excellent in durability.

Moreover, it can be seen that the ground layer containing a nitrogen-containing organic compound can exhibit a function as an electron transport layer in the case of using a transparent conductive film according to the present invention as the second electrode and thus high efficiency and durability can be obtained even the electron transport layer is not separately provided.

In addition, it has been confirmed that the photoelectric conversion efficiency and the durability were superior in the case of using a polymer type nitrogen-containing organic compound (Nos. 14 to 19) compared to the case of using a low molecular weight compound type nitrogen-containing organic compound (Nos. 6 to 13 and Nos. 20 to 25).

It can be seen that the cases are preferable particularly in which a polymer having a dithiocarbamate group (No. 16, No. 17, and No. 19) are used as the nitrogen-containing organic compound.

[Fabrication of Organic Photoelectric Conversion Element 26 (Using Transparent Conductive Film in First Electrode and Second Electrode)]

(Preparation of Substrate)

A non-alkali glass as the substrate was washed in order of the ultrasonic cleaning with CLEANTHROUGH KS3030 manufactured by Kao Corporation as a surfactant and ultrapure water and the ultrasonic cleaning with ultrapure water, and then dried by nitrogen blowing, and finally subjected to the ultraviolet ozone cleaning.

(Formation of Ground Layer)

Subsequently, a ground layer using Exemplified Compound 13 was formed by coating. In this case, a coating solution obtained by dissolving 7.5 mg of Exemplified Compound 13 in 1.0 g of 2,2,3,3-tetrafluoro-1-propanol was coated on the substrate by a spin coater under the condition of at 1500 rpm for 30 seconds and heated at a substrate surface temperature of 120° C. for 5 minutes so as to obtain a ground layer consisting of Compound 13.

Meanwhile, a ground layer consisting of Exemplified Compound 13 was formed on a separately prepared substrate by coating under the same condition as above and the film thickness thereof was measured. As a result, the film thickness was 25 nm.

(Formation of First Electrode)

Next, the substrate having the above ground layer formed thereon was installed in a vacuum deposition apparatus, the internal pressure of the vacuum deposition apparatus was reduced to $10^{-3}$ Pa or less, and then silver (Ag) was deposited at a film thickness of 8 nm and a deposition rate of 2 nm/sec so as to form a metal thin film layer on the ground layer above.

(Formation of Hole Transport Layer)

Subsequently, as a hole transport layer, an isopropanol solution containing PEDOT-PSS (CLEVIOS (registered trademark) P VP AI 4083 manufactured by Heraeus Materials Technology, conductivity of $1\times10^{-3}$ S/cm) consisting of a conductive polymer and a polyanion at 2.0% by mass was prepared and coated on the substrate having a temperature adjusted at 65° C. using a blade coater and dried so as to have a dry film thickness of about 30 nm. Thereafter, the resultant was heat treated for 20 seconds with hot air at 120° C., whereby a hole transport layer was formed on the first electrode above.

The substrate was then brought into a glove box and the following operations were performed under a nitrogen atmosphere.

First, the substrate was heat treated at 120° C. for 3 minutes under a nitrogen atmosphere.

(Formation of Photoelectric Conversion Layer)

Subsequently, an organic photoelectric conversion material composition solution was prepared by mixing 1.0% by mass of P3HT (Sepiolid P200 manufactured by BASF) as a p-type organic semiconductor material and 0.8% by mass of PC61BM (nanom spectra E100H manufactured by Frontier Carbon Corporation) as an n-type organic semiconductor material in o-dichlorobenzene and completely dissolved by stirring (for 60 minutes) while heating at 80° C. on a hot plate, and then the solution was coated on the substrate having a temperature adjusted at 80° C. using a blade coater so as to have a dry film thickness of about 170 nm and dried for 2 minutes, whereby a photoelectric conversion layer was formed on the hole transport layer above.

(Ground Layer of Second Electrode)

Subsequently, Exemplified Compound 13 was dissolved in a mixed solvent of n-butanol:hexafluoroisopropanol=1:1 (volume ratio) so as to be 0.02% by mass, respectively, thereby preparing a solution. This solution was coated on the substrate having a temperature adjusted at 65° C. using a blade coater and dried so as to have a dry film thickness of about 5 nm. Thereafter, the resultant was heat treated for 2 minutes with hot air at 100° C., whereby a ground layer was formed on the photoelectric conversion layer above.

(Formation of Second Electrode)

Next, the substrate having the above electron transport layer formed thereon was installed in a vacuum deposition apparatus. Then, the element was set such that the shadow mask with a 10 mm width was perpendicular to the transparent electrode, the internal pressure of the vacuum deposition apparatus was reduced to $10^{-3}$ Pa or less, and then silver (Ag) was deposited at a film thickness of 8 nm and a deposition rate of 2 nm/sec so as to forma second electrode on the ground layer above.

(Formation of Protective Layer)

The organic photoelectric conversion element thus obtained was conveyed to PDS2010 manufactured by Specialty Coating Systems Inc. in a state of not contacting with the atmosphere, and a protective layer consisting of the Parylene HT (refractive index of 1.55) was formed at 20 nm.

(Sealing of Organic Photoelectric Conversion Element)

Moreover, the organic photoelectric conversion element was conveyed into a glove box and then interposed between two pieces of the Ultra Barrier Solar Film UBL-9L manufactured by 3M (moisture vapor transmission rate of $<5\times10^{-4}$ g/m²/d), sealing thereof was performed using a UV curing resin (XNR5570-B1 UV RESIN manufactured by Nagase ChemTex Corporation), and then the resultant element was taken out under the atmosphere to fabricate an organic photoelectric conversion element 26 having a light receiving unit size of about 10×10 mm.

The organic photoelectric conversion element thus obtained was evaluated in the same manner as the above method, as a result, it has been confirmed that the element thus obtained is a see-through type organic photoelectric conversion element having a photoelectric conversion efficiency of 2.5% and an LT80 of 135 hours.

From this fact, it has been indicated that the transparent conductive film of the present invention can be applied not only as a second electrode but also as a first electrode.

TABLE 1

| Organic photoelectric conversion element No. | Transparent conductive film No. | Ground layer | | | Metal thin film layer | | Properties of transparent conductive film single body | | Properties of photoelectric conversion element | | Remarks |
|---|---|---|---|---|---|---|---|---|---|---|---|
| | | Material | N atom number in molecule | Film thickness | Material | Film thickness | Transmittance at 550 nm | Sheet resistance | Conversion efficiency | LT80 | |
| 1 | 1 | Nil | 0 | — | Ag | 8 nm | 38% | >10000 | 0.0% | — | Comparative Example |
| 2 | 2 | Ca(acac)₂ | 0 | 5 nm | Ag | 8 nm | 55% | 220 | 1.7% | <1 h | Comparative Example |
| 3 | 3 | Au | 0 | 5 nm | Ag | 8 nm | 58% | 135 | 1.6% | 5 h | Comparative Example |

TABLE 1-continued

| Organic photoelectric conversion element No. | Transparent conductive film No. | Ground layer | | Metal thin film layer | | Properties of transparent conductive film single body | | Properties of photoelectric conversion element | | Remarks |
|---|---|---|---|---|---|---|---|---|---|---|
| | | Material | N atom number in molecule | Film thickness | Material | Film thickness | Transmittance at 550 nm | Sheet resistance | Conversion efficiency | LT80 | |
| 4 | 4 | αNPD | 2 | 5 nm | Ag | 8 nm | 57% | 85 | 1.1% | <1 h | Comparative Example |
| 5 | 5 | TmPyPB | 3 | 5 nm | Ag | 8 nm | 64% | 63 | 1.8% | 3 h | Comparative Example |
| 6 | 6 | Exemplified Compound 1 | 4 | 5 nm | Ag | 8 nm | 80% | 30 | 2.2% | 80 h | Example |
| 7 | 7 | Exemplified Compound 10 | 6 | 5 nm | Ag | 8 nm | 83% | 21 | 2.1% | 95 h | Example |
| 8 | 8 | Exemplified Compound 13 | 6 | 5 nm | Ag | 8 nm | 88% | 11 | 2.5% | 150 h | Example |
| 9 | 9 | Exemplified Compound 18 | 6 | 5 nm | Ag | 8 nm | 83% | 18 | 2.4% | 110 h | Example |
| 10 | 10 | Exemplified Compound 20 | 7 | 5 nm | Ag | 8 nm | 88% | 8 | 2.5% | 175 h | Example |
| 11 | 11 | Exemplified Compound 68 | 9 | 5 nm | Ag | 8 nm | 88% | 8 | 2.6% | 190 h | Example |
| 12 | 12 | Exemplified Compound 74 | 12 | 5 nm | Ag | 8 nm | 88% | 7 | 2.6% | 200 h | Example |
| 13 | 13 | Exemplified Compound 79 | 12 | 5 nm | Ag | 8 nm | 90% | 7 | 2.7% | 220 h | Example |
| 14 | 14 | Exemplified Compound 31 | (polymer) | 5 nm | Ag | 8 nm | 88% | 11 | 2.4% | 260 h | Example |
| 15 | 15 | Exemplified Compound 41 | (polymer) | 5 nm | Ag | 8 nm | 88% | 25 | 2.8% | 310 h | Example |
| 16 | 16 | Exemplified Compound 52 | (polymer) | 5 nm | Ag | 8 nm | 88% | 18 | 2.9% | 350 h | Example |
| 17 | 17 | Exemplified Compound 54 | (polymer) | 5 nm | Ag | 8 nm | 88% | 16 | 2.8% | 280 h | Example |
| 18 | 18 | Exemplified Compound 46 | (polymer) | 5 nm | Ag | 8 nm | 88% | 18 | 2.9% | 320 h | Example |
| 19 | 19 | Exemplified Compound 57 | (polymer) | 5 nm | Ag | 8 nm | 88% | 10 | 2.9% | 430 h | Example |
| 20 | 20 | Exemplified Compound 13 | 6 | 5 nm | Ag | 1 nm | 93% | >10000 | 0.0% | — | Comparative Example |
| 21 | 21 | Exemplified Compound 13 | 6 | 5 nm | Ag | 2 nm | 93% | 20 | 2.2% | 75 h | Example |
| 22 | 22 | Exemplified Compound 13 | 6 | 5 nm | Ag | 10 nm | 80% | 5 | 2.7% | 220 h | Example |
| 23 | 23 | Exemplified Compound 13 | 6 | 5 nm | Ag | 15 nm | 46% | 3.3 | 1.5% | 220 h | Comparative Example |
| 24 | 24 | Exemplified Compound 13 | 6 | 5 nm | Ag | 8 nm | 84% | 18 | 2.5% | 200 h | Example |
| 25 | 25 | Exemplified Compound 13 | 6 | 5 nm | Cu | 8 nm | 80% | 15 | 2.5% | 185 h | Example |
| 26[1)] | — | Exemplified Compound 13 | 6 | 25 nm | Ag | 8 nm | — | — | 2.6% | 150 h | Example |
| | | Exemplified Compound 13 | 6 | 5 nm | Ag | 8 nm | | | | | |

[Fabrication of Organic Photoelectric Conversion Elements 31 to 35 (Change in Transmittance and Refractive Index Depending on Protective Layer)]

<Fabrication of Organic Photoelectric Conversion Element 31>

An organic photoelectric conversion element 31 was obtained in the same manner as the fabrication of the organic photoelectric conversion element 7 above except using a protective layer consisting of poly(trifluoroethyl acrylate) which was formed by spin coating a 0.2 wt % toluene solution of poly(trifluoroethyl acrylate) (manufactured by Sigma-Aldrich Co. LLC., refractive index of 1.41) and had a film thickness of 20 nm instead of the Parylene HT (refractive index of 1.55) as a protective layer on the metal thin film layer.

<Fabrication of Organic Photoelectric Conversion Element 32>

An organic photoelectric conversion element 32 was obtained in the same manner as the fabrication of the organic photoelectric conversion element 7 above except using a protective layer consisting of Parylene C which was formed using Parylene C and had a film thickness of 20 nm instead of the Parylene HT (refractive index of 1.55) as a protective layer on the metal thin film layer.

<Fabrication of Organic Photoelectric Conversion Element 33>

An organic photoelectric conversion element 33 was obtained in the same manner as the fabrication of the organic photoelectric conversion element 7 above except using a protective layer consisting of Alq3 which was formed by depositing tris(8-quinolinolato)aluminum (Alq3) (manufactured by Sigma-Aldrich Co. LLC., refractive index of 1.73) and had a film thickness of 20 nm instead of the Parylene HT (refractive index of 1.55) as a protective layer on the metal thin film layer.

<Fabrication of Organic Photoelectric Conversion Element 34>

The organic photoelectric conversion element 34 was obtained in the same manner as the fabrication of the organic photoelectric conversion element 7 above except using a protective layer consisting of Exemplified Compound 13 which was formed by depositing Exemplified Compound 13 (refractive index of 1.79) and had a film thickness of 20 nm instead of the Parylene HT (refractive index of 1.55) as a protective layer on the metal thin film layer.

<Fabrication of Organic Photoelectric Conversion Element 35>

An organic photoelectric conversion element 35 was obtained in the same manner as the fabrication of the organic photoelectric conversion element 7 above except using a protective layer consisting of titanium oxide obtained by spin coating a methanol diluent of tetraisopropoxy titanium (manufactured by Tokyo Chemical Industry Co., Ltd.) and then leaving to stand for 1 hour in the air instead of the Parylene HT (refractive index of 1.55) as a protective layer on the metal thin film layer.

The organic photoelectric conversion elements thus obtained were evaluated in the same manner as the above method. The results are presented in Table 2 below.

14b Second photoelectric conversion layer,
25 Substrate,
26 Hole transport layer,
26a Inorganic material layer,
26b Organic material layer,
27 Electron transport layer,
38 Charge recombination layer,
38a Second electron transport layer, and
38b Second hole transport layer.

What is claimed is:

1. An organic photoelectric conversion element comprising;
a first electrode,
a second electrode, and
a photoelectric conversion layer present between the first electrode and the second electrode, wherein
at least one of the first electrode and the second electrode is a transparent conductive film formed by laminating a ground layer comprising a nitrogen-containing organic compound and a metal thin film layer comprising a metal element of Group 11 of the periodic table and having a thickness of from 2 to 10 nm, and
the nitrogen-containing organic compound comprises a compound represented by the following Formula (1), or a polymer compound having a partial structure repre-

TABLE 2

| Organic photoelectric conversion element No. | Ground layer | | Metal thin film layer | | Protective layer | | Properties of transparent conductive film single body | | | Properties of photoelectric conversion element | | Remarks |
|---|---|---|---|---|---|---|---|---|---|---|---|---|
| | Material | Film thickness | Material | Film thickness | Material | Refractive index | Transmittance at 550 nm | Sheet resistance | | Conversion efficiency | LT80 | |
| 5 | Exemplified Compound 13 | 5 nm | Ag | 8 nm | Parylene HT | 1.55 | 88% | 11 | | 2.5% | 150 h | Example |
| 31 | Exemplified Compound 13 | 5 nm | Ag | 8 nm | Poly(trifluoroethyl acrylate) | 1.41 | 75% | 11 | | 2.4% | 85 h | Example |
| 32 | Exemplified Compound 13 | 5 nm | Ag | 8 nm | Parylene C | 1.63 | 86% | 11 | | 2.5% | 120 h | Example |
| 33 | Exemplified Compound 13 | 5 nm | Ag | 8 nm | Alq3 | 1.73 | 80% | 11 | | 2.4% | 110 h | Example |
| 34 | Exemplified Compound 13 | 5 nm | Ag | 8 nm | Exemplified Compound 10 | 1.79 | 88% | 11 | | 2.7% | 115 h | Example |
| 35 | Exemplified Compound 13 | 5 nm | Ag | 8 nm | Titanium oxide | 1.90 | 71% | 11 | | 2.1% | 25 h | Example |

From the results above, it has been confirmed that the transmittance is 80% or more in a case in which the refractive index of the protective layer is from 1.5 to 1.8. In addition, it has been confirmed that a decrease in photoelectric conversion efficiency can be suppressed by setting the refractive index of the protective layer to be 1.8 or less.

EXPLANATIONS OF LETTERS OR NUMERALS 1A and 1B Transparent conductive film,
2 Ground layer,
3 Metal thin film layer,
4 Protective layer,
10, 20, and 30 Organic photoelectric conversion element,
11 Cathode,
12 Anode,
14 Photoelectric conversion layer,
14a First photoelectric conversion layer, sented by the following Formula (2), or a polymer compound having a partial structure represented by the following Formula (3), $$(A^1)_{n1}\text{-}Y^1 \quad \text{Formula (1)}$$

in Formula (1), $A^1$ represents a monovalent nitrogen atom-containing group,
n1 represents an integer of 2 or more, and
$Y^1$ includes a group derived from a structure represented by the following Formula (4)

Formula (4)

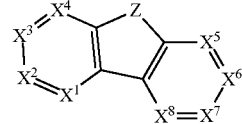

in Formula (4), Z represents —CR$^1$R$^2$—, —NR$^3$—, —O—, —S—, or —SiR$^4$R$^5$—, X$^1$ to X$^8$ each independently represent —CR$^6$= or —N=, R$^1$, R$^2$, R$^4$, R$^5$ and R$^6$ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms, and R$^3$ represents a single bond (—), a hydrogen atom, a substituted or unsubstituted alkyl group having from 1 to 20 carbon atoms, a substituted or unsubstituted cycloalkyl group having from, 3 to 20 carbon atoms, a substituted or unsubstituted aryl group having from 6 to 30 carbon atoms, or a substituted or unsubstituted alkyloxy group having from 1 to 20 carbon atoms, $-\!\!\!+\!\!A^2\text{-}Y^2\!\!+\!\!\!-$  Formula (2)

in Formula (2), A$^2$ represents a divalent group derived from a structure formed by two monovalent nitrogen atom-containing groups represented by any of the following structures N-1 to N-11 and N-39 to N-45 which are linked via a divalent linking group selected from the group consisting of a substituted or unsubstituted arylene group having from 6 to 18 carbon atoms, a substituted unsubstituted heteroarylene group having from 6 to 18 carbon atoms and amino group:

-continued

N-42
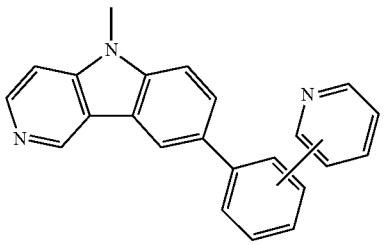

N-43
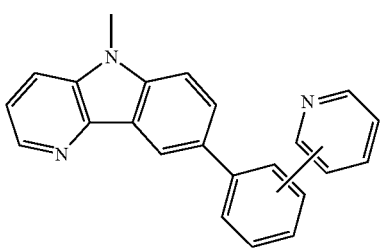

N-44
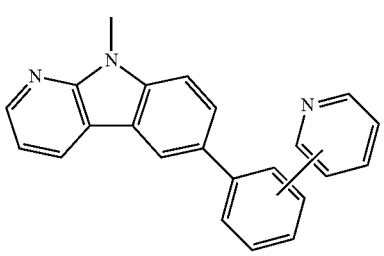

N-45
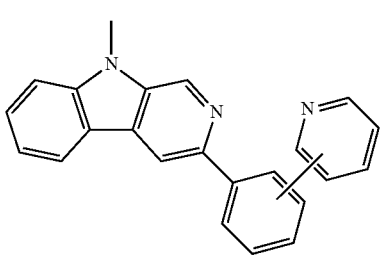

and

Y² represents a single bond (—),

Formula (3)

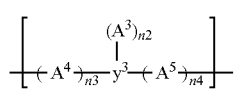

in Formula (3), A³ represents a monovalent nitrogen atom-containing group,

A⁴ and A⁵ each independently represent a divalent nitrogen atom-containing group, n2 represents an integer of 1 or more, n3 and n4 each independently represent an integer of 0 or 1, and Y³ represents an (n2+2)-valent organic group.

2. The organic photoelectric conversion element according to claim 1, wherein A¹ or A³ above comprises a dithiocarbamate group or an amino group.

3. The organic photoelectric conversion element according to claim 1, wherein A¹, A², A³, A⁴ or A⁵ above comprises a pyridine ring-containing group.

4. The organic photoelectric conversion element according to claim 1, wherein Y³ above includes a group derived from a structure represented by the following Formula (4):

Formula (4)

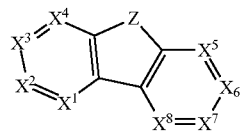

in Formula (4), Z represents —CR¹R²—, —NR³—, —O—, —S—, or —SiR⁴R⁵—,

X¹ to X⁸ each independently represent —CR⁶═ or —N═, and

R¹ to R⁶ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms.

5. The organic photoelectric conversion element according to claim 1, wherein the nitrogen-containing organic compound comprises a compound represented by the Formula (1) and comprising 5 or more nitrogen atoms.

6. The organic photoelectric conversion element according to claim 1, wherein the metal thin film layer consists of silver.

7. The organic photoelectric conversion element according to claim 1, wherein the nitrogen compound has a weight average molecular weight of 3,000 or more.

8. The organic photoelectric conversion element according to claim 1, wherein the ground layer is formed by a manufacturing method comprising a coating process using a solvent comprising a fluorine-containing alcohol.

9. The organic photoelectric conversion element according to claim 1, wherein the second electrode is the transparent conductive film.

10. The organic photoelectric conversion element according to claim 1, wherein a thickness of the ground layer is from 5 to 30 nm.

11. The organic photoelectric conversion element according to claim 1, wherein the transparent conductive film further comprises a protective layer having a refractive index of from 1.5 to 1.8 on the metal thin film layer.

12. A solar cell comprising the organic photoelectric conversion element according to claim 1.

13. A transparent conductive film comprising a ground layer comprising a nitrogen-containing organic compound and a metal thin film layer formed on the ground layer, the metal thin film layer comprising a transition metal element of Group 11 of the periodic table and having a thickness of from 2 to 10 nm, wherein the nitrogen-containing organic compound comprises a polymer compound having a partial structure represented by the following Formula (2) or a polymer compound having a partial structure represented by the following Formula (3),

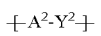 Formula (2)

in Formula (2), A² represents a divalent group derived from a structure formed by two monovalent nitrogen atom-containing groups represented by any of the following structures N-1 to N-11 and N-39 to N-45 which are linked via a divalent linking group selected from the group consisting of a substituted or unsubstituted arylene group having from 6 to 18 carbon atoms, a substituted or unsubstituted heteroarylene group having from 6 to 18 carbon atoms and imino group:
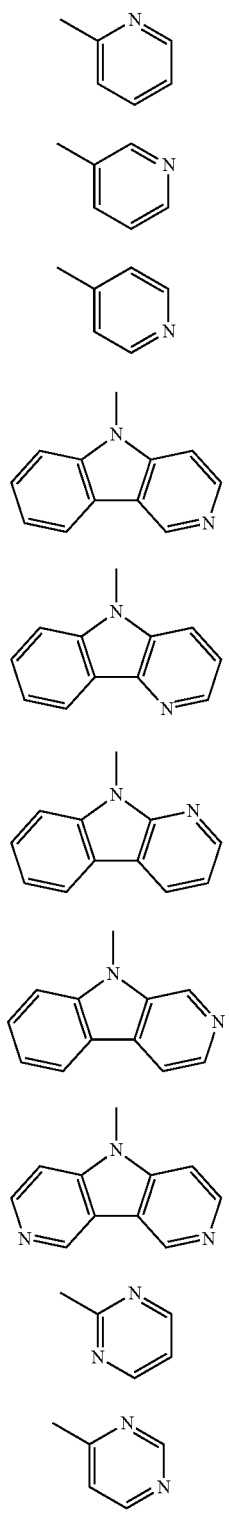
N-1
N-2
N-3
N-4
N-5
N-6
N-7
N-8
N-9
N-10
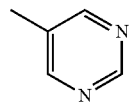
N-11
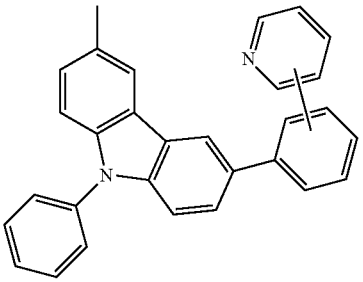
N-39
N-40
N-41
N-42
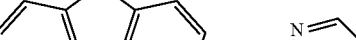
N-43

-continued

N-44

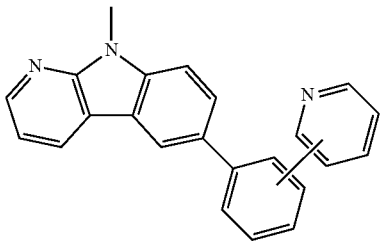

N-45

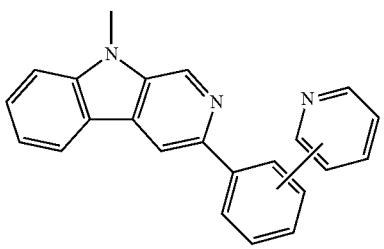

and Y² represents a single bond (—),

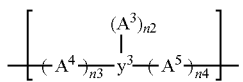 Formula (3)

in Formula (3), A³ represents a monovalent nitrogen atom-containing group,
A⁴ and A⁵ each independently represent a divalent nitrogen atom-containing group,
n2 represents an integer of 1 or more,
n3 and n4 each independently represent an integer of 0 or 1, and
Y³ represents an (n2+2)-valent organic group.

14. A transparent conductive film comprising a ground layer comprising a nitrogen-containing organic compound and a metal thin film layer formed on the ground layer, the metal thin film layer comprising a transition metal element of Group 11 of the periodic table and having a thickness of from 2 to 10 nm, wherein
the nitrogen-containing organic compound comprises a compound comprising 5 or more nitrogen atoms and represented by the following Formula (1):

 Formula (1)

in Formula (1), A¹ represents a monovalent nitrogen atom-containing group,
n1 represents an integer of 2 or more, and
Y¹ includes a group derived from a structure represented by the following Formula (4)

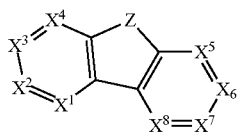 Formula (4)

in Formula (4), Z represents —CR¹R²—, —NR³—, —O—, —S—, or —SiR⁴R⁵—,

X¹ to X⁸ each independently represent —CR⁶= or —N=,
R¹, R², R⁴, R⁵ and R⁶ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms, and
R³ represents a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted alkyloxy group having from 1 to 20 carbon atoms.

15. A transparent conductive film comprising a ground layer comprising a nitrogen-containing organic compound and a metal thin film layer formed on the ground layer, the metal thin film layer comprising a transition metal element of Group 11 of the periodic table and having a thickness of from 10 to 30 nm, wherein
the nitrogen-containing organic compound comprises a compound comprising 5 or more nitrogen atoms and represented by the following Formula (1), or a polymer compound having a partial structure represented by the following Formula or a polymer compound having a partial structure represented by the following Formula (3),

 Formula (1)

in Formula (1), A¹ represents a monovalent nitrogen atom-containing group,
n1 represents an integer of 2 or more, and
Y¹ includes a group derived from a structure represented by the following Formula (4)

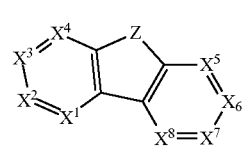 Formula (4)

in Formula (4), Z represents —CR¹R²—, —NR³—, —O—, —S—, or —SiR⁴R⁵—,
X¹ to X⁸ each independently represent —CR⁶= or —N=,
R¹, R², R⁴, R⁵ and R⁶ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms, and
R³ represents a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted alkyloxy group having from 1 to 20 carbon atoms,

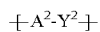 Formula (2)

in Formula (2), $A^2$ represents a divalent group derived from a structure formed by two monovalent nitrogen atom-containing groups represented by any of the following structures N-1 to N-11 and N-39 to N-45 which are linked via a divalent linking group selected from the group consisting of a substituted or unsubstituted arylene group having from 6 to 18 carbon atoms, a substituted or unsubstituted heteroarylene group having from 6 to 13 carbon atoms and imino group:

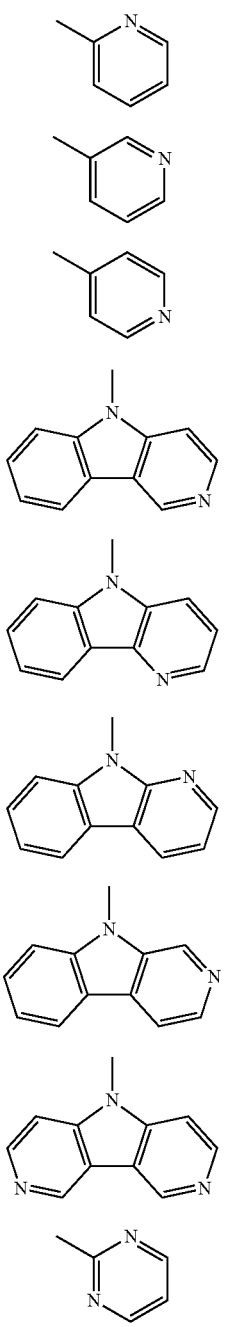

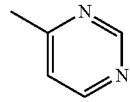
N-10

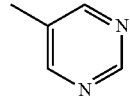
N-11

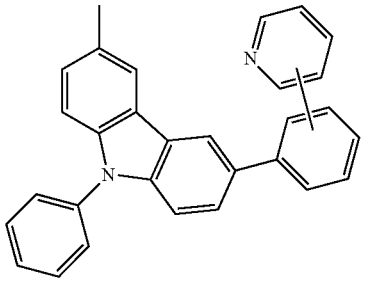
N-39

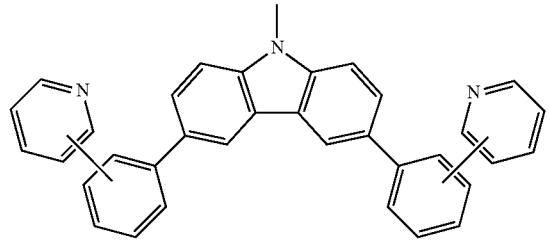
N-40

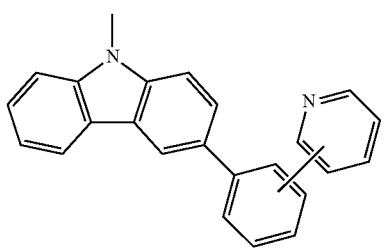
N-41

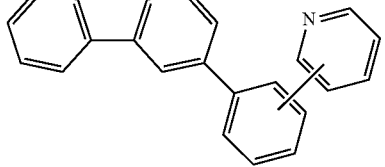
N-42

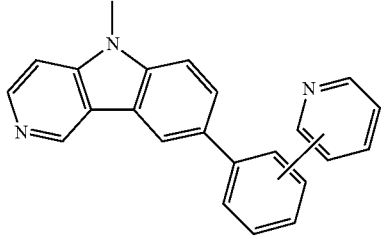
N-43

-continued

N-44

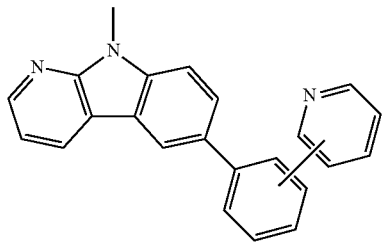

N-45

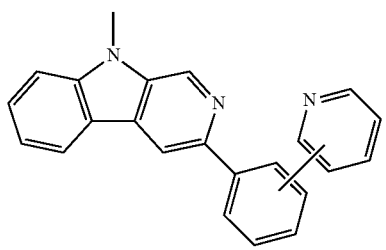

and

Y² represents a single bond (—),

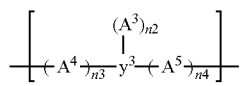  Formula (3)

in Formula (3), A³ represents a monovalent nitrogen atom-containing group,

A⁴ and A⁵ each independently represent a divalent nitrogen atom-containing group, n2 represents an integer of 1 or more, n3 and n4 each independently represent an integer of 0 or 1, and Y³ represents an (n2+2)-valent organic group.

16. A method of manufacturing a transparent conductive film comprising;

forming a ground layer by forming a film of a nitrogen-containing organic compound, and forming a metal thin film layer comprising a transition metal element of Group 11 of the periodic table and having a thickness of from 2 to 10 nm or from 10 to 30 nm on the ground layer, wherein the nitrogen-containing organic compound comprises a compound represented by the following Formula (1), or a polymer compound having a partial structure represented by the following Formula (2), or a polymer compound having a partial structure represented by the following Formula (3), $(A^1)_{n1}\text{-}Y^1$  Formula (1)

in Formula (1), A¹ represents a monovalent nitrogen atom-containing group, n1 represents an integer of 2 or more, and Y¹ includes a group derived from a structure represented by the following Formula (4)

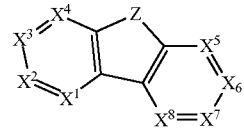  Formula (4)

in Formula (4), Z represents —CR¹R²—, —NR³—, —O—, —S—, or —SiR⁴R⁵—,

X¹ to X⁸ each independently represent —CR⁶= or —N=,

R¹, R², R⁴, R⁵ and R⁶ each independently represent a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, a substituted or unsubstituted heteroaryl group having from 1 to 30 carbon atoms, or a substituted or unsubstituted alkyloxy group having from 1 to 20 carbon atoms, and R³ represents a single bond (—), a hydrogen atom, a substituted or unsubstituted alkyl group having from 1 to 20 carbon atoms, a substituted or unsubstituted cycloalkyl group having from 3 to 20 carbon atoms, a substituted or unsubstituted aryl group having from 6 to 30 carbon atoms, or a substituted or unsubstituted alkyloxy group having from 1 to 20 carbon atoms, $\text{\textlbrackdbl}A^2\text{-}Y^2\text{\textrbrackdbl}$  Formula (2)

in Formula (2), A² represents a divalent group derived from a structure formed by two monovalent nitrogen atom-containing groups represented by any of the following structures N-1 to N-11 and N-39 to N-45 which are linked via a divalent linking group selected from the group consisting of a substituted or unsubstituted arylene group having from 6 to 18 carbon atoms, a substituted unsubstituted heteroarylene group having from 6 to 18 carbon atoms and imino group:

N-1

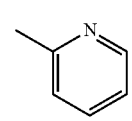

N-2

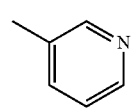

N-3

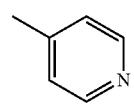

N-4

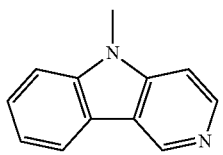

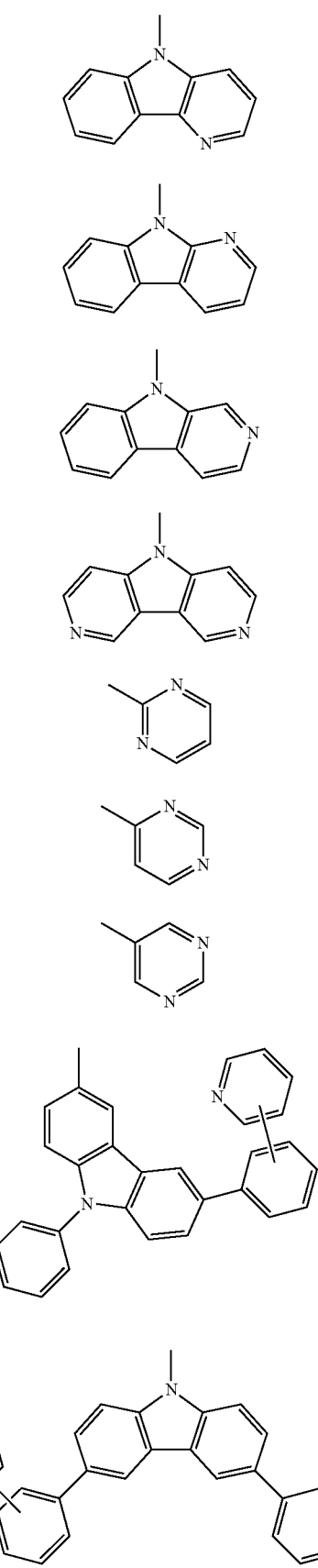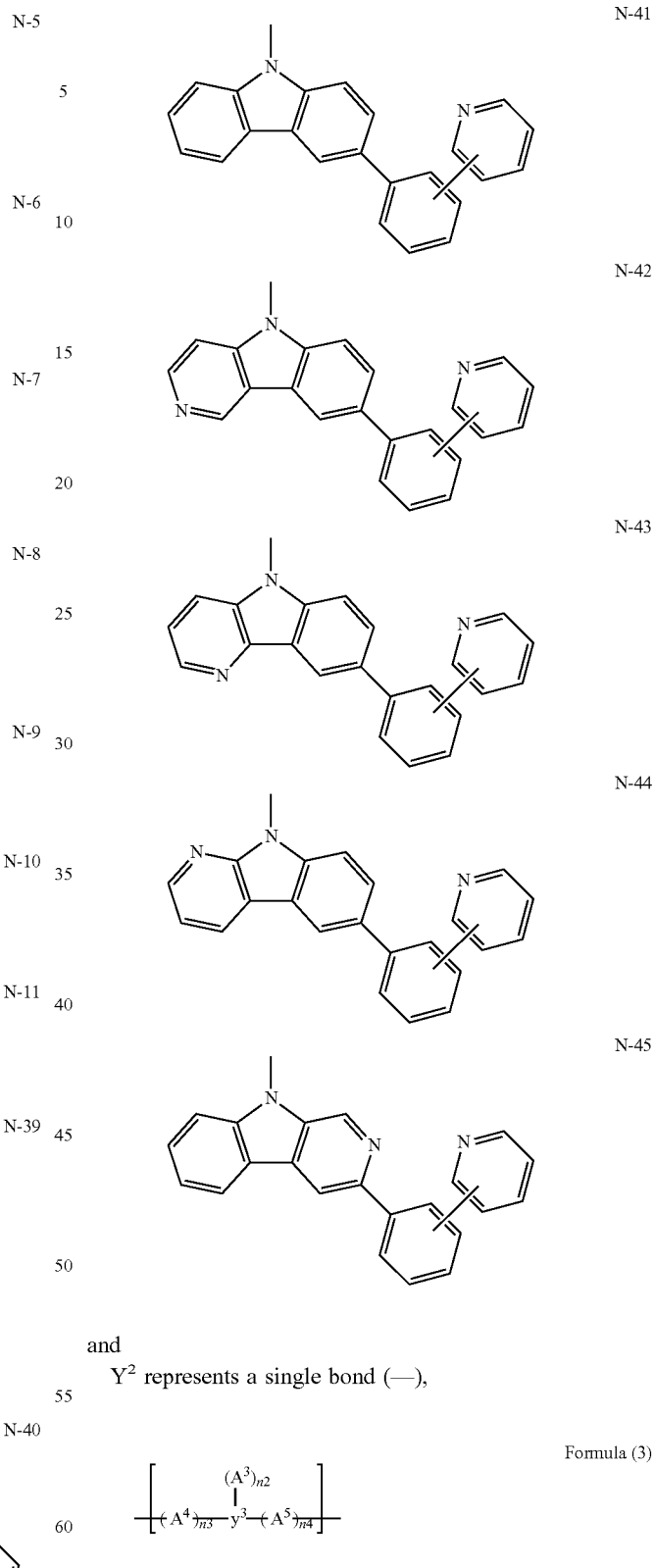
and
$Y^2$ represents a single bond (—),
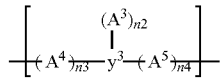
Formula (3)
in Formula (3), $A^3$ represents a monovalent nitrogen atom-containing group,
$A^4$ and $A^5$ each independently represent a divalent nitrogen atom-containing group,
n2 represents an integer of 1 or more, n3 and n4 each independently represent an integer of 0 or 1, and $Y^3$ represents an (n2+2)-valent organic group.

\* \* \* \* \*